US012207825B2

(12) United States Patent
Rankins, III et al.

(10) Patent No.: US 12,207,825 B2
(45) Date of Patent: *Jan. 28, 2025

(54) TWISTING ASSEMBLY FOR TIGHTENING AN ELONGATED FLEXIBLE MATERIAL

(71) Applicant: RCR Medical Products LLC, Melissa, TX (US)

(72) Inventors: Robert C. Rankins, III, McKinney, TX (US); Adam Cole Ewing, McKinney, TX (US)

(*) Notice: Subject to any disclaimer, the term of this patent is extended or adjusted under 35 U.S.C. 154(b) by 439 days.

This patent is subject to a terminal disclaimer.

(21) Appl. No.: 17/613,462

(22) PCT Filed: May 23, 2020

(86) PCT No.: PCT/US2020/034425
§ 371 (c)(1),
(2) Date: Nov. 22, 2021

(87) PCT Pub. No.: WO2020/237229
PCT Pub. Date: Nov. 26, 2020

(65) Prior Publication Data
US 2022/0313276 A1    Oct. 6, 2022

Related U.S. Application Data

(60) Provisional application No. 62/852,173, filed on May 23, 2019, provisional application No. 62/862,641, (Continued)

(51) Int. Cl.
*A61B 17/132* (2006.01)

(52) U.S. Cl.
CPC ................ *A61B 17/1327* (2013.01)

(58) Field of Classification Search
CPC .................................. A61B 17/1327
See application file for complete search history.

(56) References Cited

U.S. PATENT DOCUMENTS 7,842,067 B2 * 11/2010 Esposito ............ A61B 17/1322
606/203
11,406,394 B2 * 8/2022 Strattner ................ B43K 29/00
(Continued)

FOREIGN PATENT DOCUMENTS

DE   102018201019 A1   8/2018

OTHER PUBLICATIONS

Notice of Allowance, dated Sep. 29, 2022, U.S. Appl. No. 16/882,611, issued as U.S. Pat. No. 11,504,136 on Nov. 22, 2022, 36 pages.
(Continued)

*Primary Examiner* — Julian W Woo
(74) *Attorney, Agent, or Firm* — Todd E. Albanesi; Booth Albanesi Schroeder PLLC

(57) ABSTRACT

A twisting assembly (600, 900, 1000, or 1100) for tightening an elongated flexible material (100) including a base part (610, 910, 1010, or 1110) having a plurality of teeth (640, 940, 1040, or 1140) arranged in a circle; and a twisting part (650, 950, 1050, or 1150) adapted for rotating relative to the base part and the twisting part having a windlass portion (680, 980, 1080, or 1180). A portion of the elongated flexible material can be operatively connected to the windlass portion such that when the windlass portion is rotated, the portion of the material is twisted. The twisting assembly is adapted to allow movement of the twisting part away from close engagement with the teeth of the base part to allow rotation of the twisting part in one rotational direction relative to the base part. The twisting assembly is adapted to cooperatively allow movement of the twisting part into close engagement with the teeth of the base part to prevent rotation of the twisting part in the opposite rotational direction.

25 Claims, 26 Drawing Sheets

Related U.S. Application Data filed on Jun. 17, 2019, provisional application No. 62/873,958, filed on Jul. 14, 2019, provisional application No. 62/892,463, filed on Aug. 27, 2019, provisional application No. 62/892,479, filed on Aug. 27, 2019.

(56) References Cited

U.S. PATENT DOCUMENTS

| | | |
|---|---|---|
| 11,504,136 B2 * | 11/2022 | Rankins, III ....... A61B 17/1327 |
| 2005/0113866 A1 | 5/2005 | Heinz et al. |
| 2009/0062842 A1 | 3/2009 | Esposito et al. |
| 2010/0057120 A1 | 3/2010 | Kirkham |
| 2015/0094756 A1 | 4/2015 | Kosiorek et al. |
| 2015/0190262 A1 | 7/2015 | Capra et al. |
| 2018/0042616 A1 | 2/2018 | Demas et al. |

OTHER PUBLICATIONS

PCT/US2020/34425, International Search Report and Written Opinion, issued Sep. 15, 2020, 20 pages.

* cited by examiner

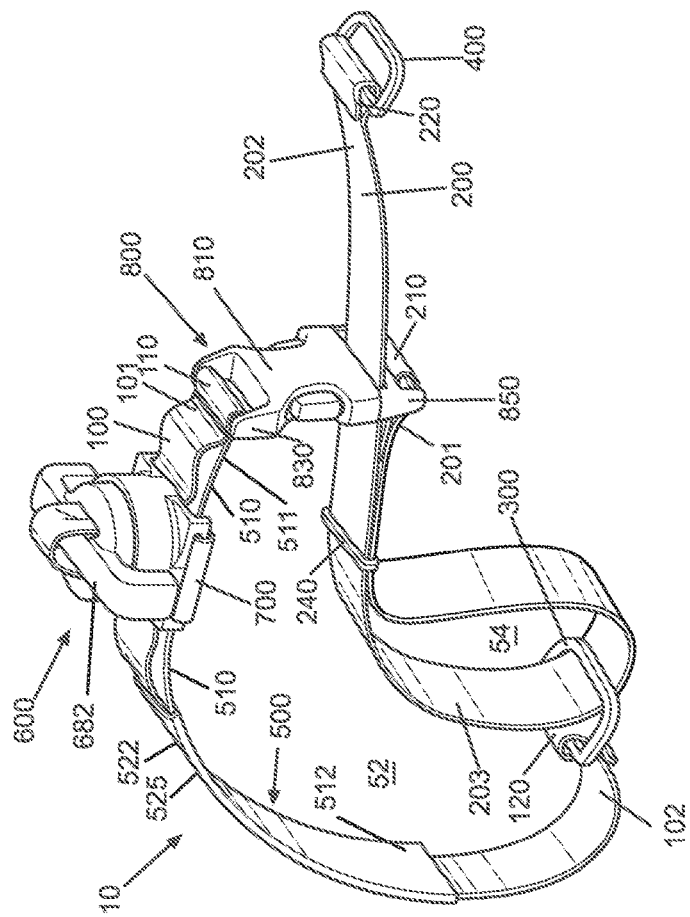
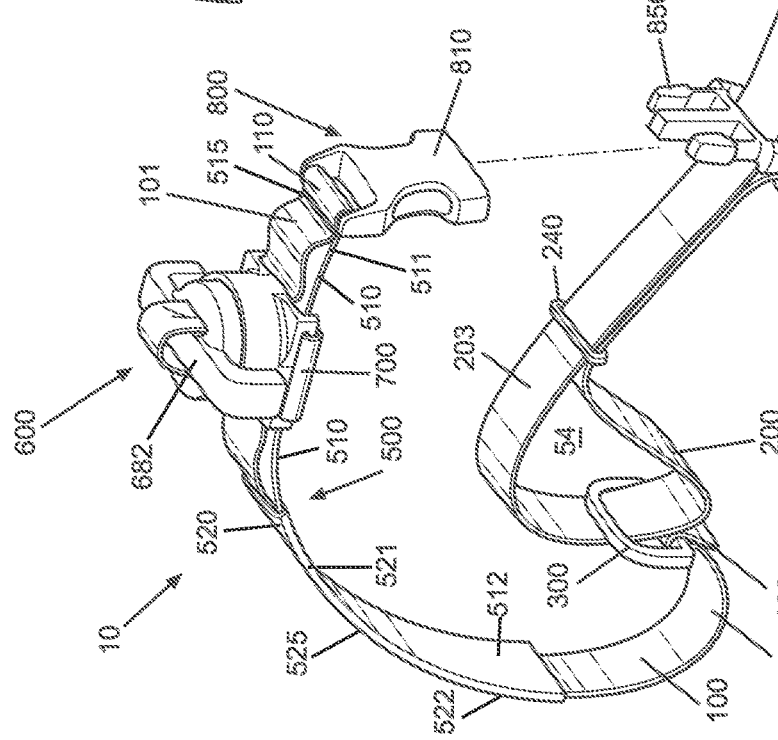
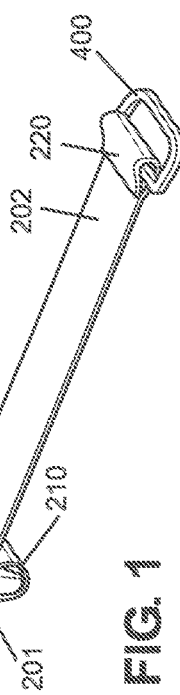

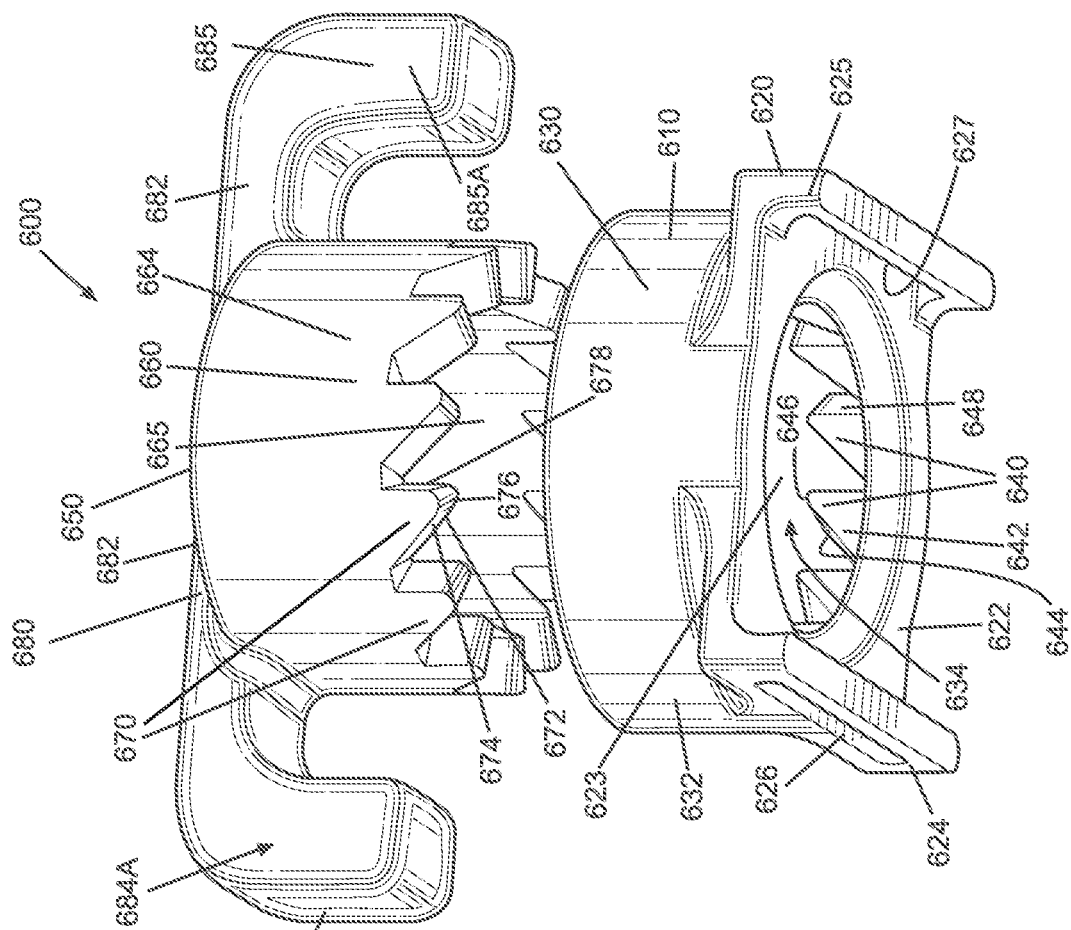
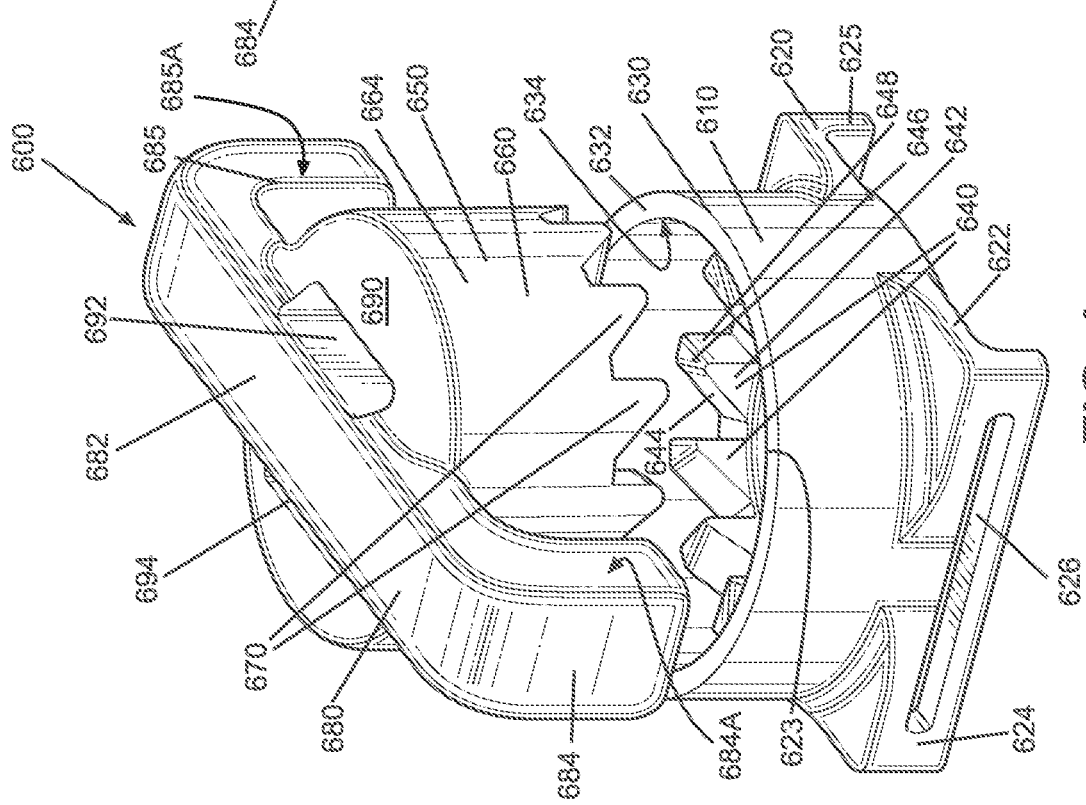
FIG. 5
FIG. 4

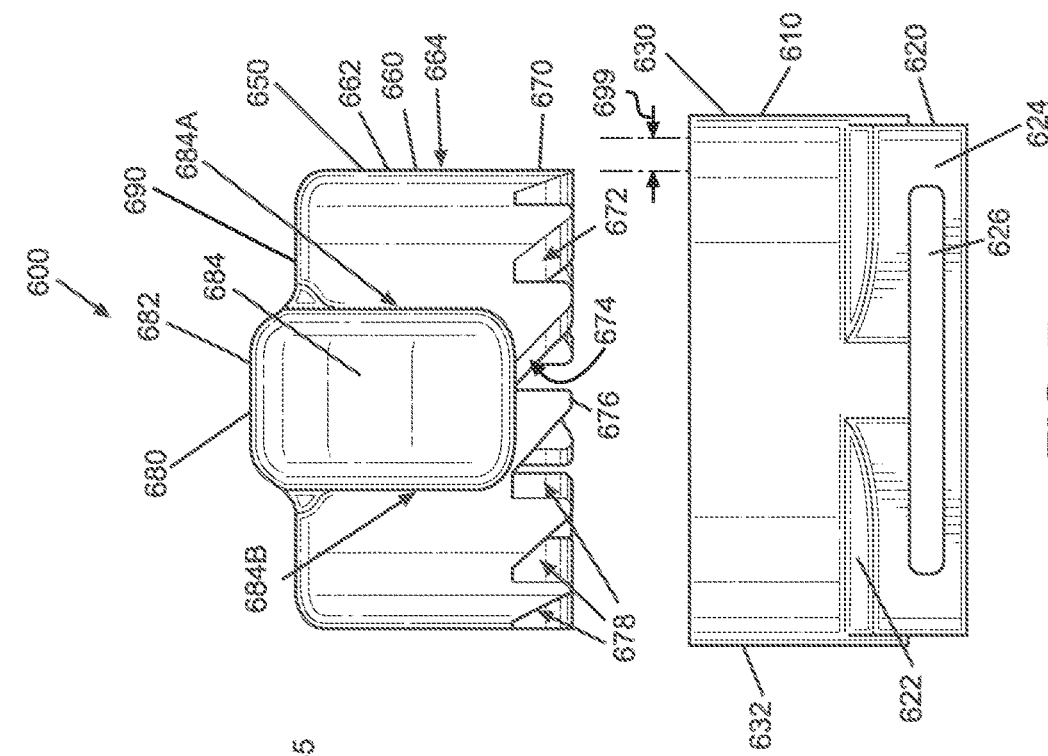
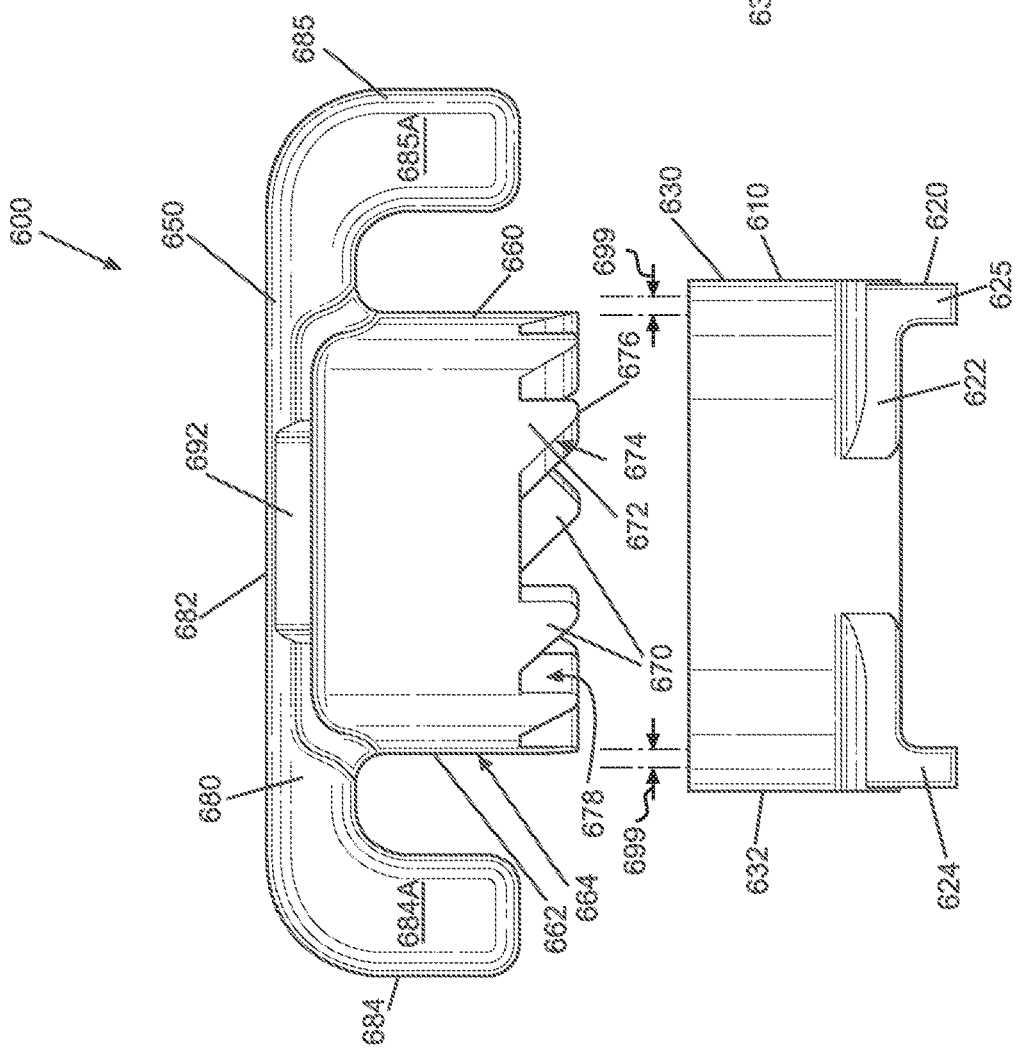

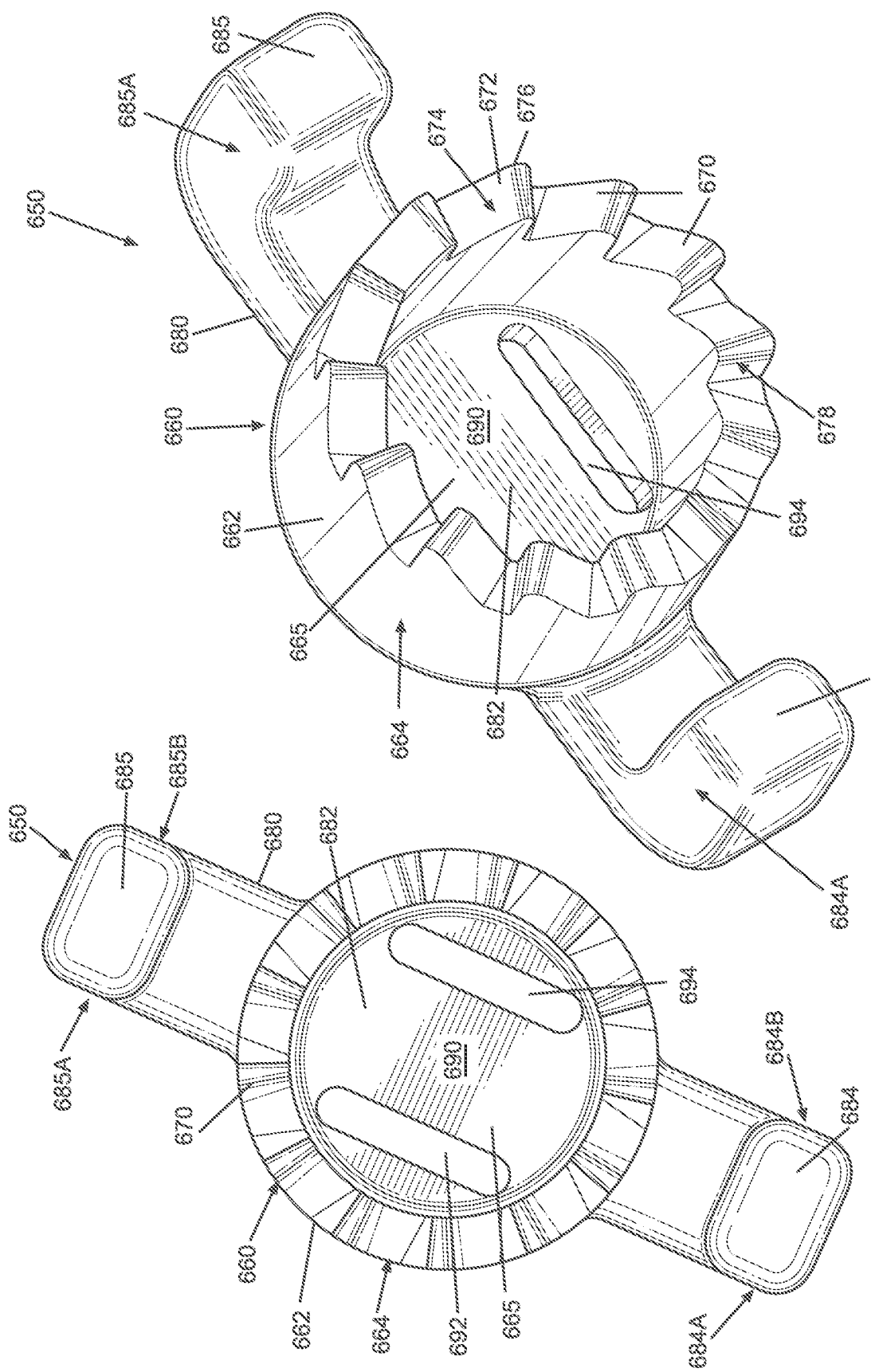

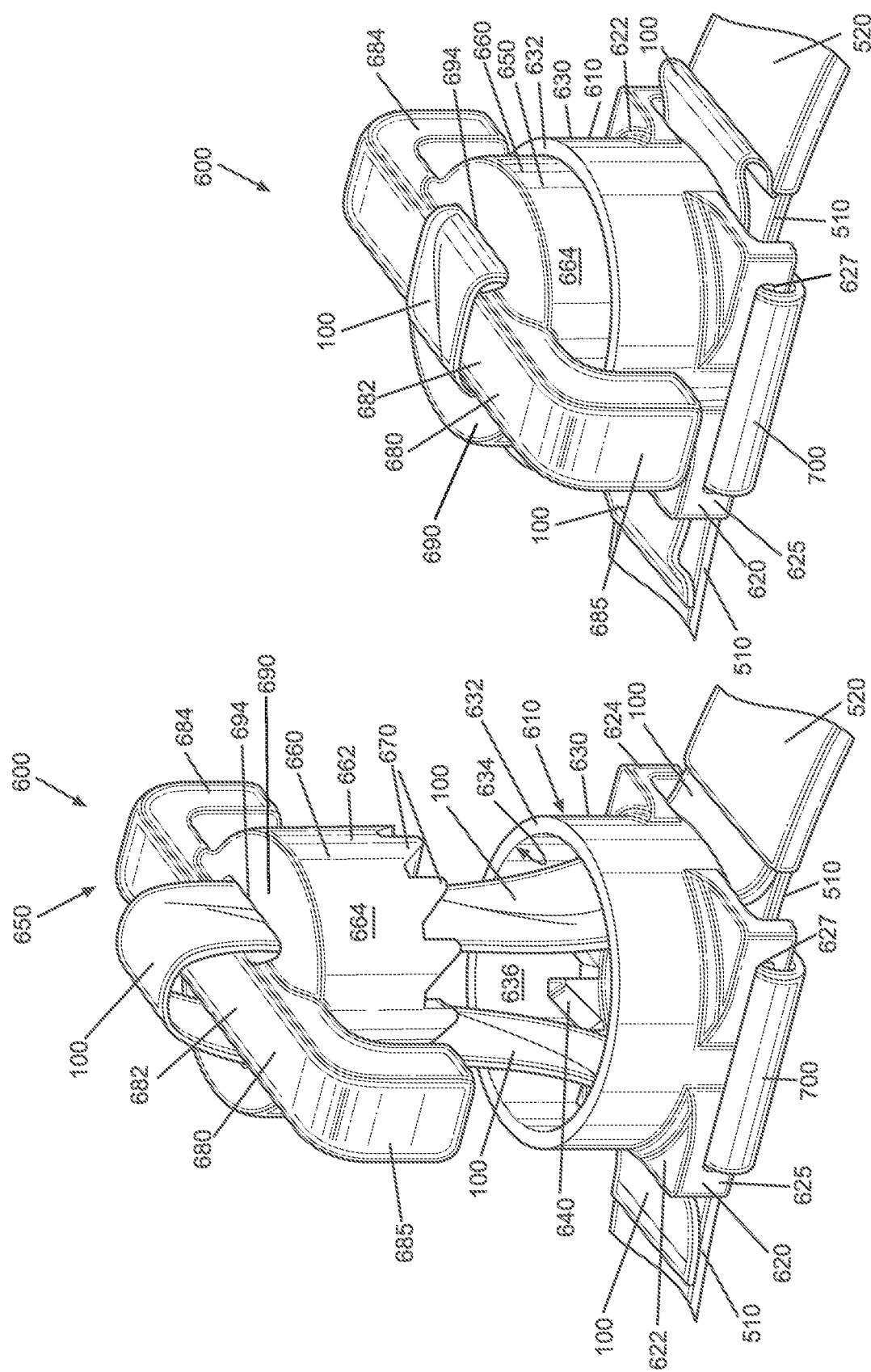

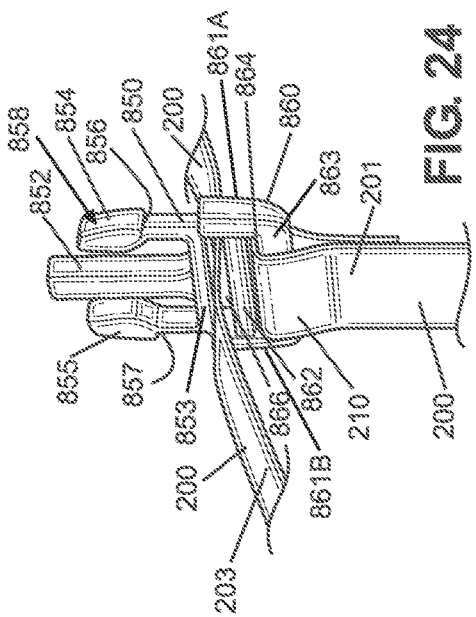
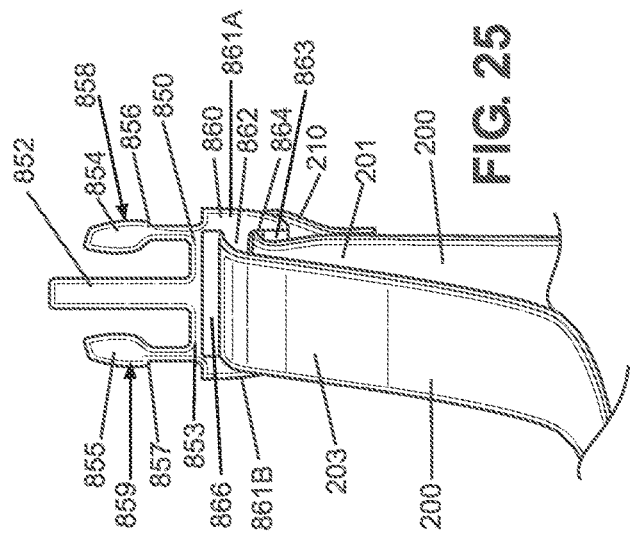
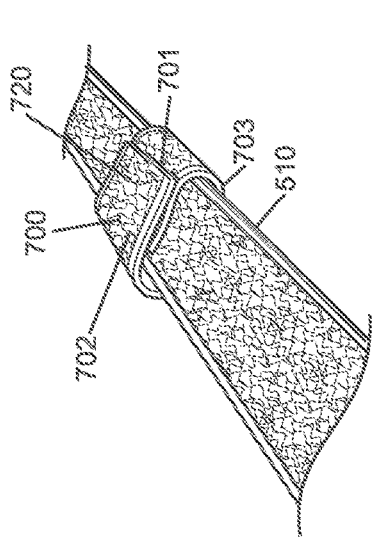
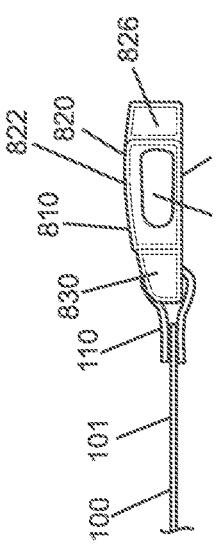
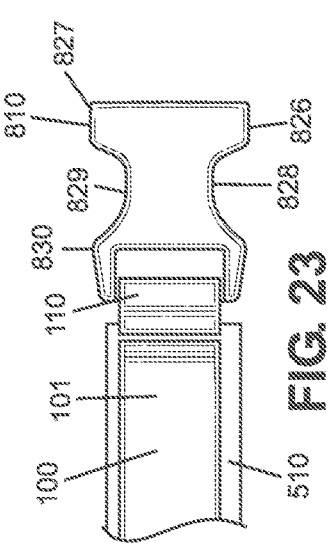

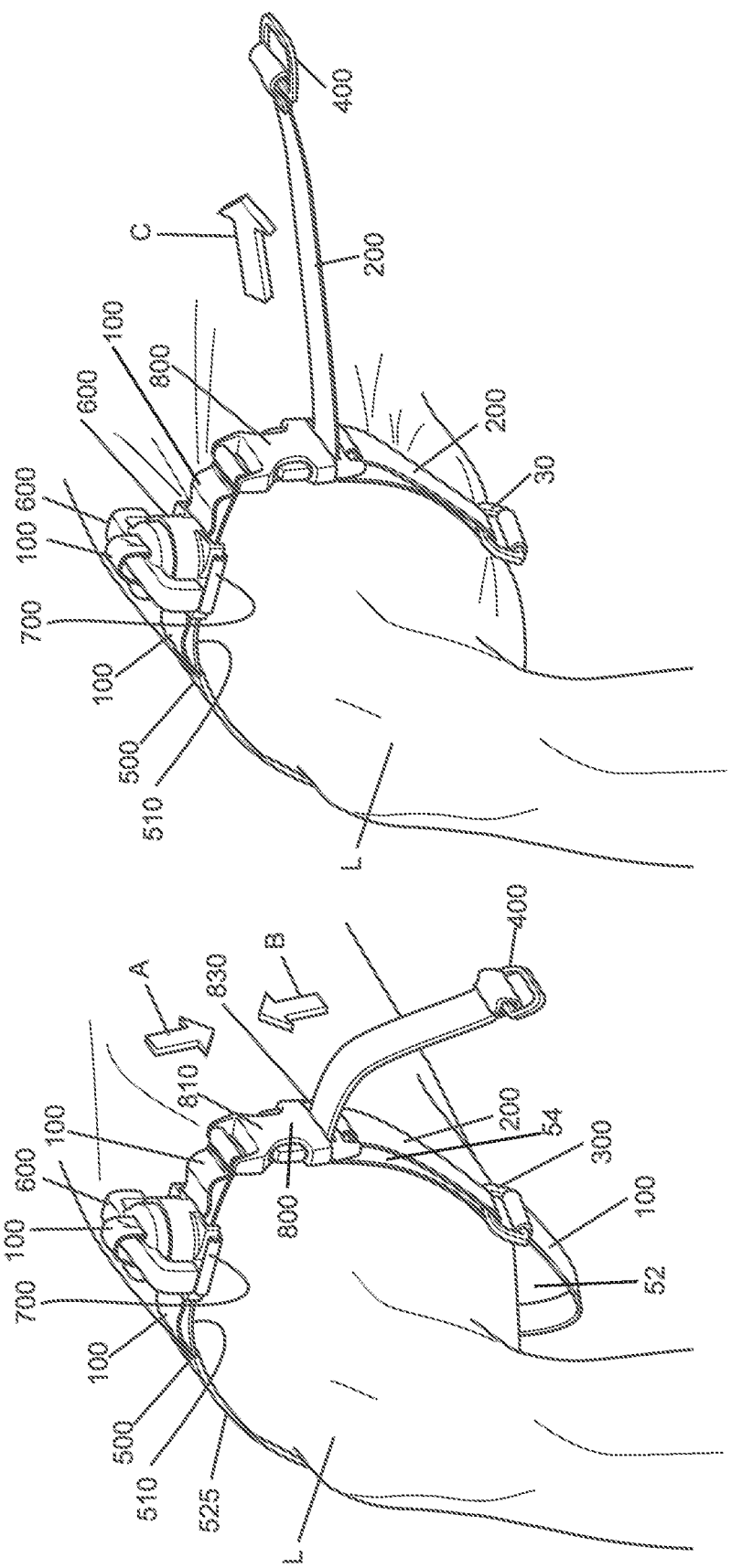

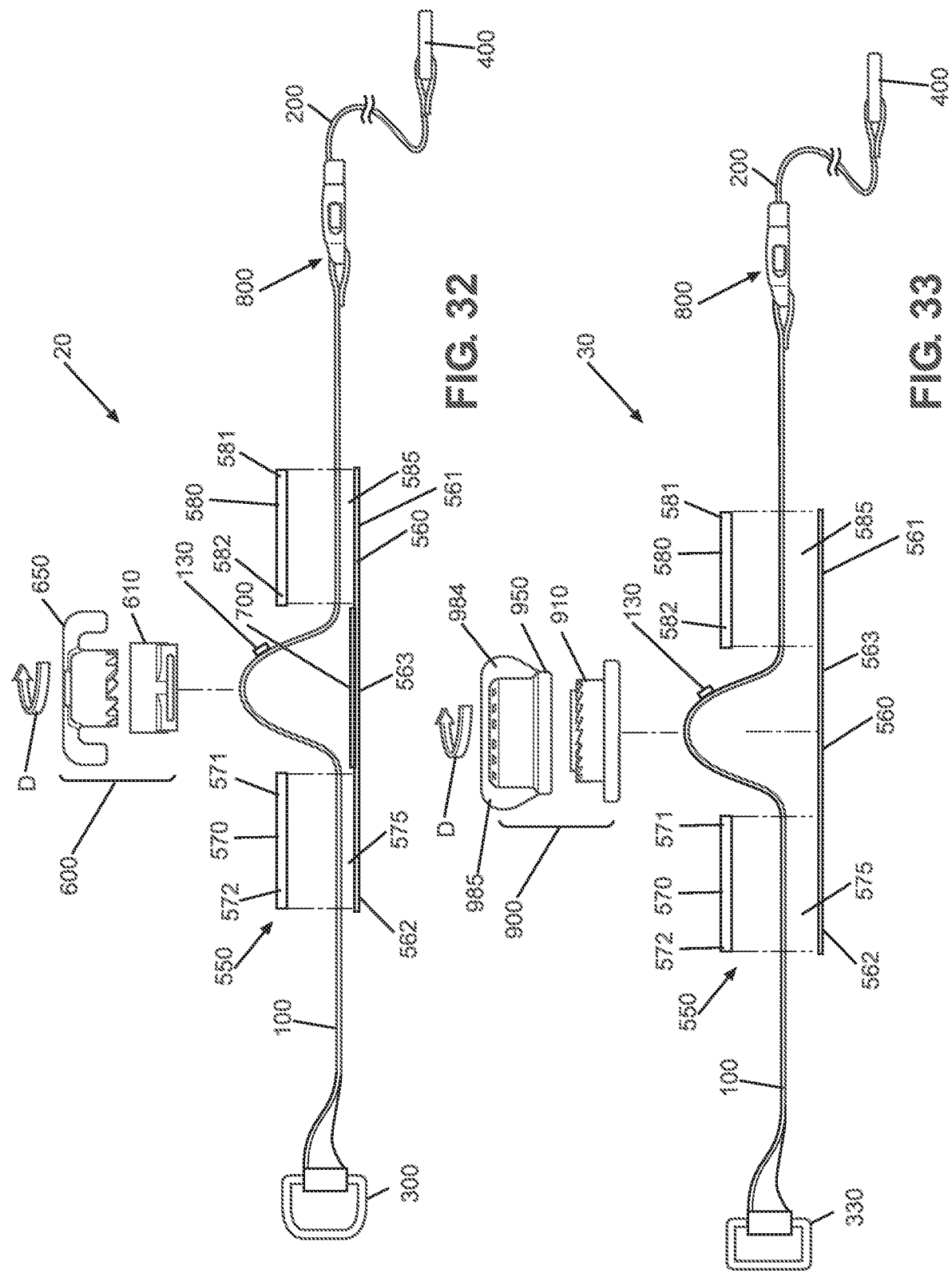

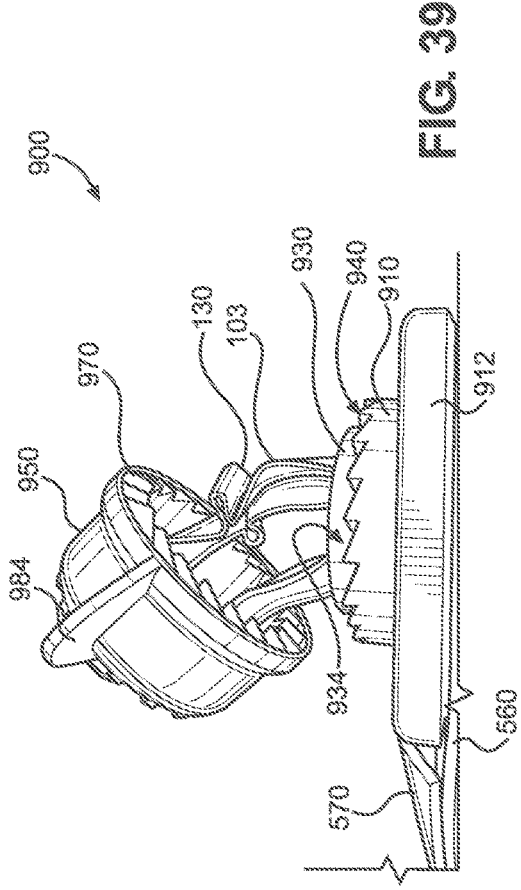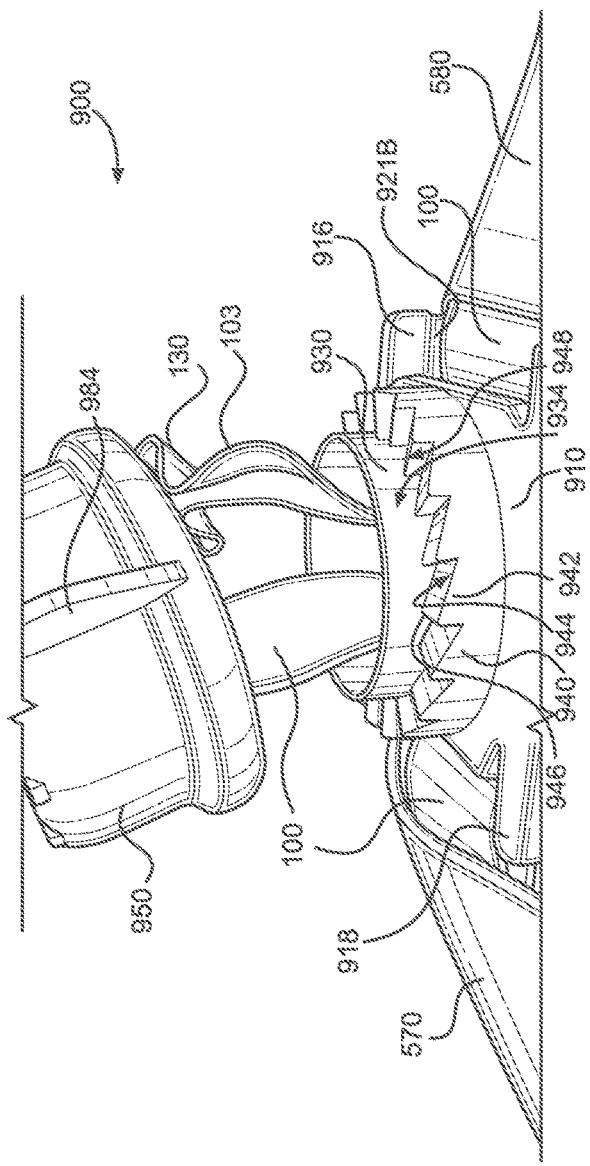

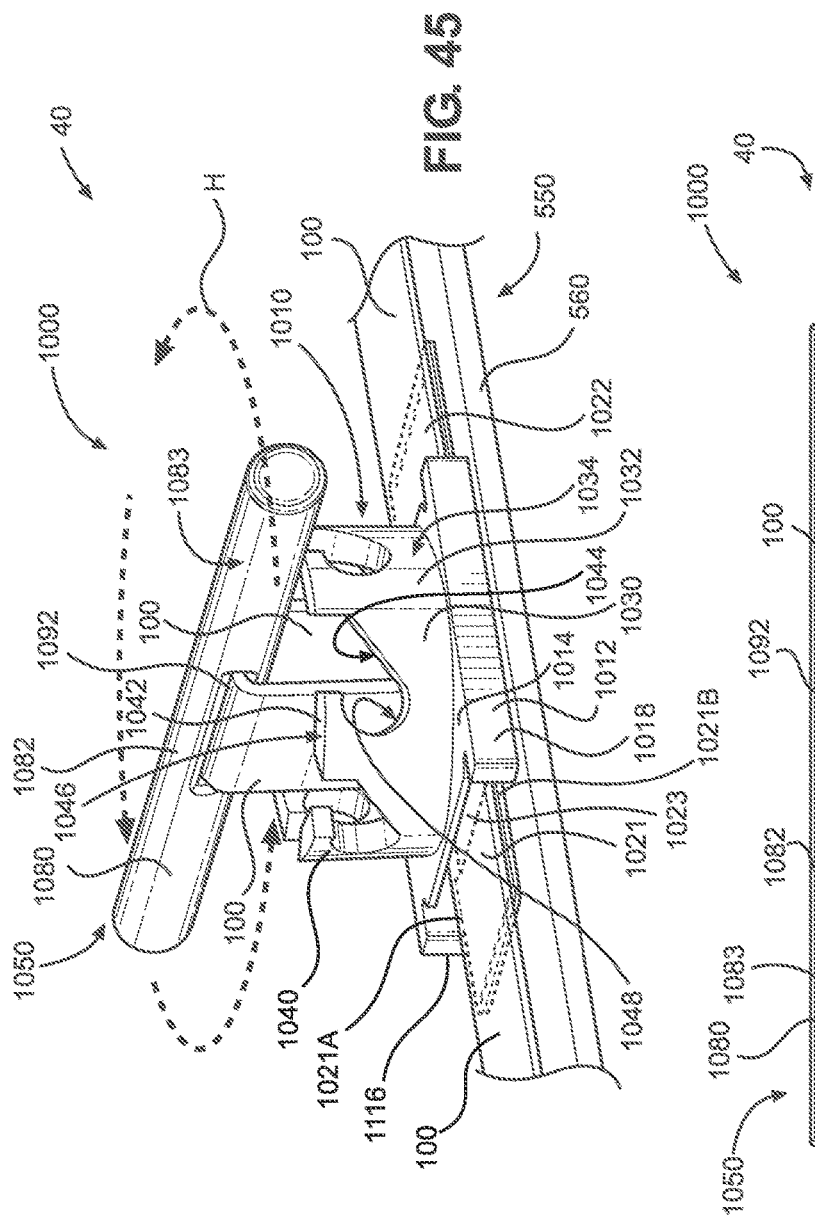
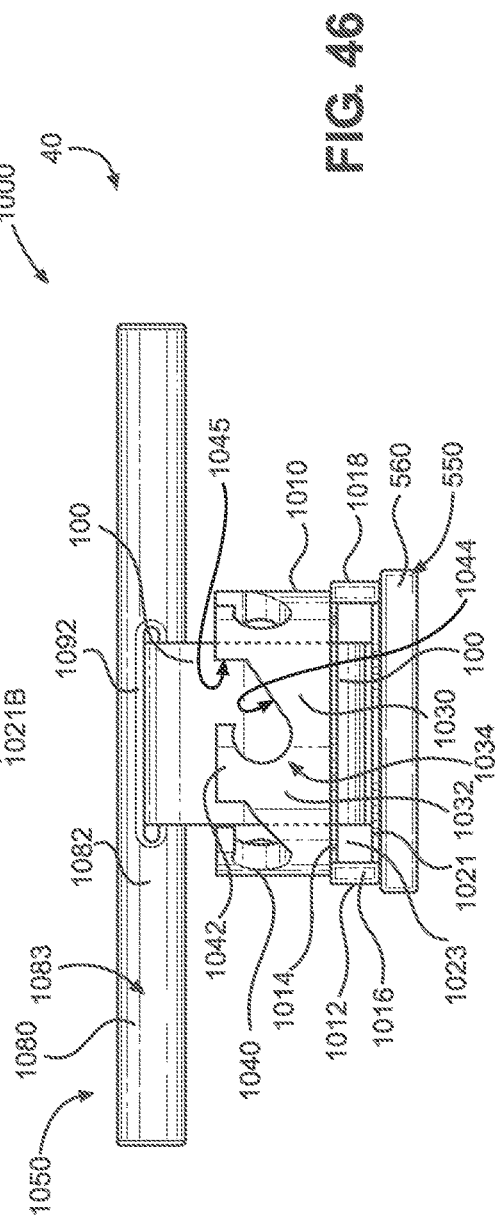
FIG. 45
FIG. 46

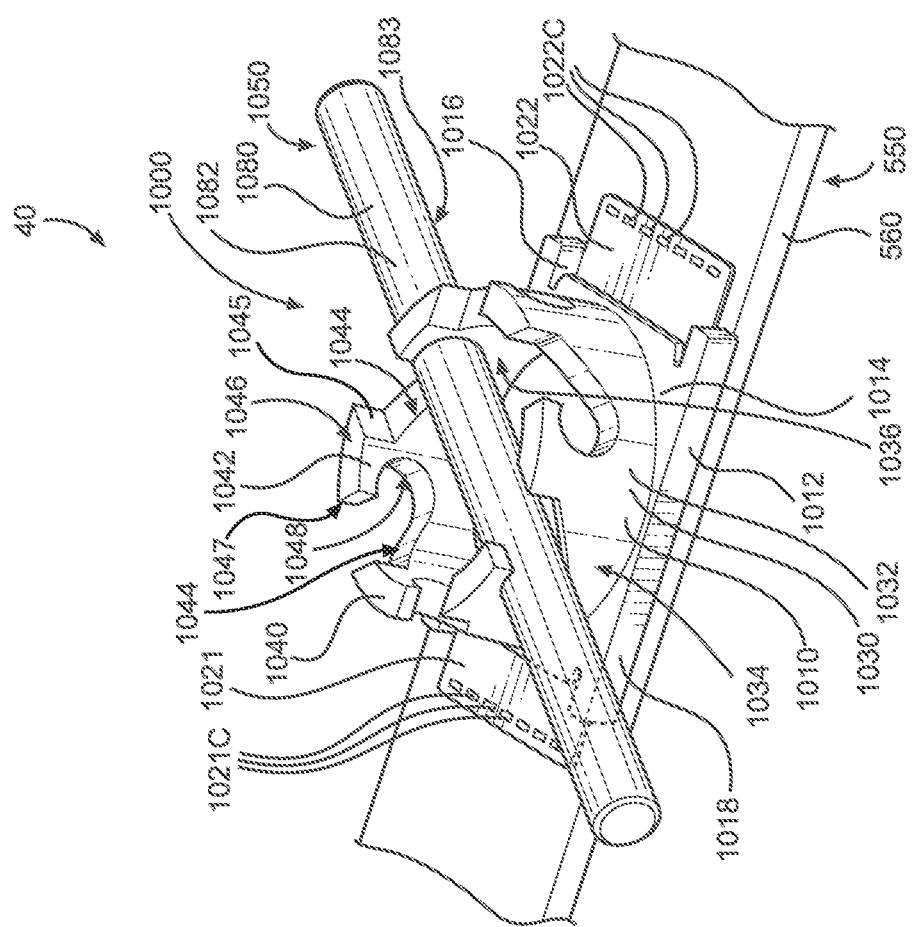
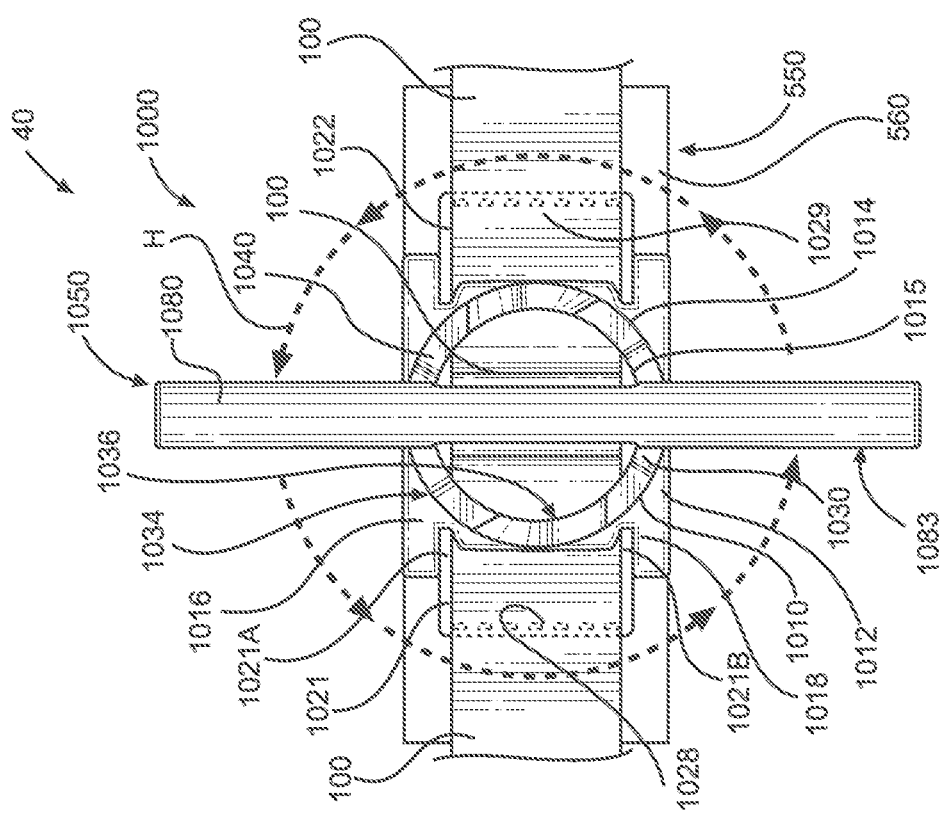
FIG. 48
FIG. 47

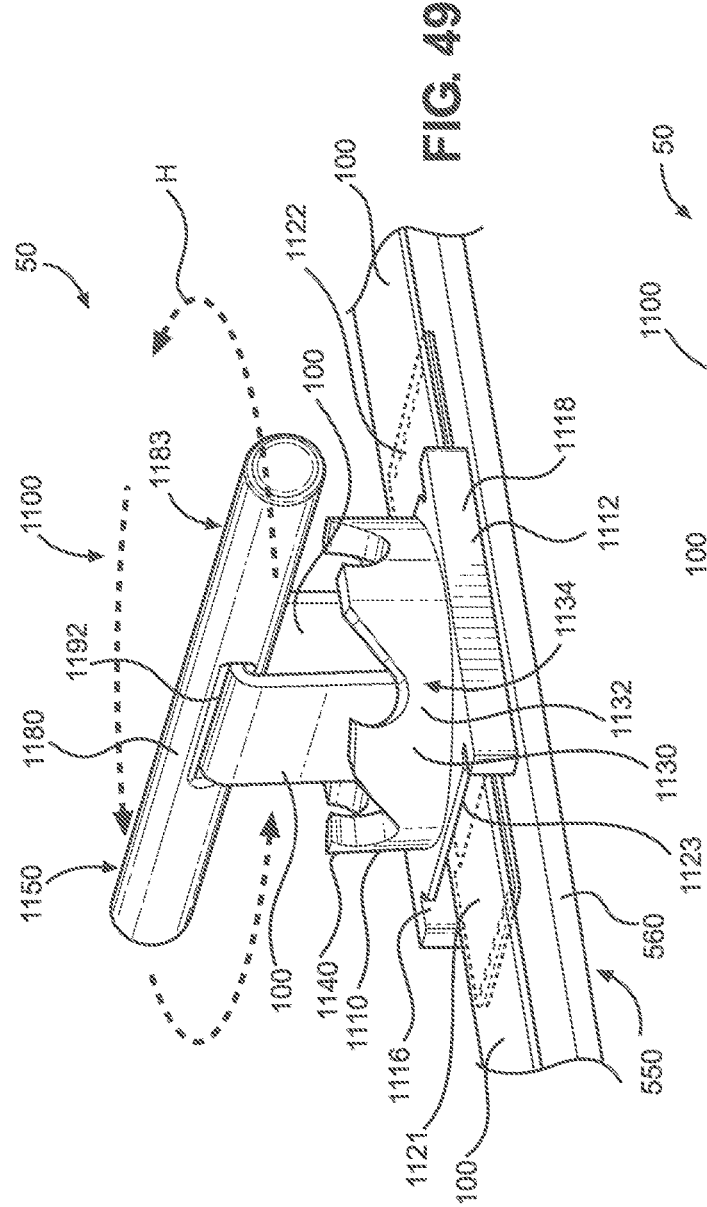
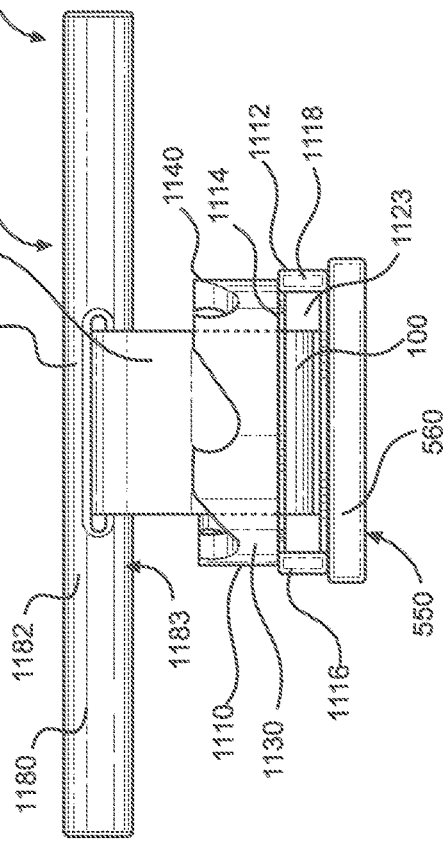
FIG. 49
FIG. 50

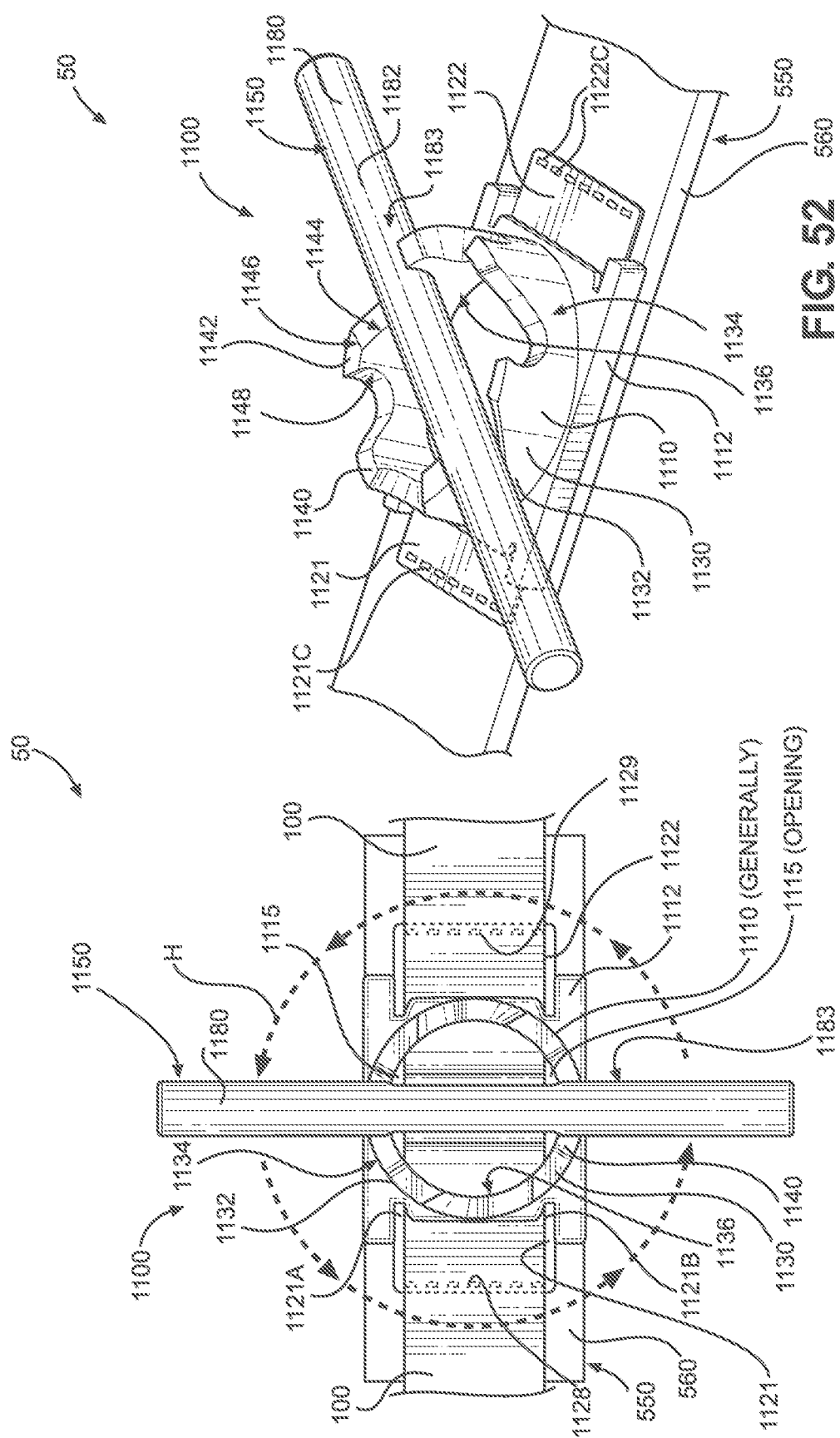

TWISTING ASSEMBLY FOR TIGHTENING AN ELONGATED FLEXIBLE MATERIAL

CROSS-REFERENCE TO RELATED APPLICATIONS

This application claims the priority of each of these prior applications:
- (a) U.S. provisional application No. 62/892,479 filed Aug. 27, 2019 entitled Twisting Assembly for Tightening a Strap;
- (b) U.S. provisional application No. 62/892,463 filed Aug. 27, 2019 entitled Tourniquet with Twisting Assembly;
- (c) U.S. provisional application No. 62/873,958 filed Jul. 14, 2019 entitled Tourniquet with Twisting Assembly;
- (d) U.S. provisional application No. 62/862,641 filed Jun. 17, 2019 entitled Tourniquet with Twisting Assembly; and
- (e) U.S. provisional application No. 62/852,173 filed May 23, 2019 entitled Tourniquet with Twisting Assembly;

each having for inventors Robert C. Rankins, III and Adam Cole Ewing.

TECHNICAL FIELD

This disclosure is in the field of devices and methods for tightening a strap, cord, chain, rope, or other elongated flexible material.

BACKGROUND

There are many examples of applications for tightening of a strap, cord, chain, rope, or other elongated flexible material. An example of an application for tightening of a strap is in tourniquets. Tourniquets are medical devices used to restrict, slow, or stop blood flow, usually to a limb but they can be used to slow or stop the flow of blood to a wound on another portion of the body. A tourniquet can be used in an emergency to save a person from life-threatening blood loss. In a situation of uncontrolled bleeding, especially from a large artery or multiple blood vessels, an injured person can bleed out in as little as sixty seconds after a traumatic injury.

One of the uses of a tourniquet is in military or paramilitary combat situations.

For example, tourniquets have become a part of basic medical training in the United States Army and tourniquets are integrated into the "Soldier as a System" (SaaS) program. The "SaaS" is everything worn, carried, or consumed by a soldier. Specific requirements for Army tourniquets have included that the device must be adequate for either upper or lower extremity application and it must include a windlass.

Preferably, the length of a tourniquet should accommodate the 99th percentile of the anthropometric size range to accommodate the increasing sizes of some patients. An effective circumferential length of about 28 inches (about 71 cm) is sufficient to accommodate most persons. More preferably, the length of a tourniquet should accommodate up to a circumference of about 37.5 inches (about 95.3 cm) to accommodate the thighs of very large persons.

Preferably, the length of a tourniquet for adults should accommodate the upper arm of a thin person. More preferably, the length of a tourniquet should accommodate down to a circumference of about 7 inches (about 18 cm). Of course, tourniquet applications for children would sometimes require even smaller sizes.

The width of a tourniquet is a factor in tourniquet design. The torque required for pressure applied by a tourniquet changes in direct relation to the width of the tourniquet. The wider the tourniquet, the less pressure is required to occlude the artery, but the wider the tourniquet the more torque must be applied to the device to achieve that occluding pressure. Research shows the best median point at this time is about 1.5 inches (about 3.8 cm) for the width of a tourniquet. In addition, narrow devices have breakage and inefficacy issues, while wider ones, if used improperly, can exacerbate nerve injury. About one inch (about 2.5 cm) is a preferred minimum width and about two inches (about 5.1 cm) is a preferred maximum width. Preferably, the width of a tourniquet should be at least about 1.5 inches (about 3.8 cm).

Placement of a tourniquet can make a big difference to the effectiveness of a tourniquet. Despite having more underlying bone, the lower portions of limbs tend to be easier to occlude than the upper portions.

It is known that that limb blood occlusion pressure varies based on both limb circumference and tourniquet width. An applied pressure of 300-500 mmHg has reportedly been shown as an excellent range of safety for the tourniquets used in some tourniquet studies.

It is known that nerve palsy does not occur until 500 mmHg of pressure is applied, which is a high pressure difficult to achieve with most tourniquets. Preferably, tourniquet breakage can be adapted to occur at 500 mmHg of pressure, with significant deformation, if not outright breakage, occurring at that pressure.

Additional factors, especially for military purposes, are weight and compactness. As a tourniquet (or two) are part of the equipment carried by a soldier, weight is a factor. However, given that the weight of a tourniquet is not great, a more compact design can be more important than a small weight difference between two competing devices.

While one-handed operation (self-application) of a tourniquet is desirable in certain emergencies, especially for pilots of aircraft or special forces operations, as of 2011 the one-handed requirement was anticipated to likely be phased out from the U.S. Tactical Combat Casualty Care ("TCCC") Guidelines. There has been a decreased percentage of self-application of tourniquets, down to close to 1% of applications. In addition, trapped-limb scenarios comprise a tiny proportion of the injured population. Nevertheless, the possibility for one-handed operation is desirable, even if not usually needed.

Clear packaging is preferred so that the user can see what is in the package. However, ultraviolet light is known to degrade a variety of materials, so packaging and component materials should be considered accordingly.

Preferably, a tourniquet for military or paramilitary application should be suitable for long-term storage in a realistic temperature extremes in the range of −60° F. (−51° C.) to +150° F. (+66° C.) and suitable for operational use in the range of −60° F. (−51° C.) to +130 F. (+54° C.).

Preferably, the manufacture date and lot number should appear on the tourniquet to aid in life-cycle determination when stored for long term.

Usually only one tourniquet is issued to military or paramilitary personnel, although issuing a second tourniquet would probably be valuable and useful in some situations. For example, it has been recently reported that for the US military, "there are approximately one and a half [tourniquets] per casualty, with a max of five."

Preferably, tourniquets should be clean, and more preferably substantially sterile for medical applications. It is desirable to minimize pathogens that are applied to the skin, especially if near a severe wound.

Tourniquets are usually considered a one-time use item, however, if a tourniquet is ineffective because of improper placement, it would be desirable if it could be removed and re-applied. A one-time use (also known as a "single-use") tourniquet can be re-positioned for continued use on a single patient.

Preferably, simple instructions for use should be included with the tourniquet or on the packaging for the tourniquet, although often additional training will be employed for military personnel, paramilitary personnel, or first-responders.

A major problem with the use of tourniquets is difficulty staging a tourniquet for use in an emergency. It is desirable that a tourniquet be simple and quick to operate under stressful conditions. Preferably, a tourniquet should be able to be applied in less than 60 seconds. Of course, some advance training may be required to apply a tourniquet quickly.

Another major problem with some prior art tourniquets is breakages during use. A tourniquet needs to be operable and withstand breakage in actual use, otherwise it is ineffective.

With recent wars and police actions, it has become increasingly desirable to modernize and improve tourniquets.

At least as of 2019, the FDA has no specific standards for tourniquets. As of Jul. 11, 2019, a nonpneumatic tourniquet device is exempt from the premarket notification procedures in subpart E of part 807 of 21 C.F.R. Chapter 1, subject to the limitations in § 878.9. 21 C.F.R. § 878.5900(b).

Additional background information regarding tourniquets is available in the minutes of a "Tourniquet Working Group" of Mar. 23, 2010, by the U.S. Department of Defense, Defense Medical Materiel Program Office, 693 Neiman Street, 2nd Floor, Fort Detrick, Maryland 21702, Memorandum dated May 2, 2011.

Numerous efforts have been made to improve on tourniquet design. Nevertheless, prior tourniquets can be difficult to apply, especially as speed of application is often required.

There has been a long-felt need for an improved nonpneumatic tourniquet, especially for use in an emergency. Such a device and method can be used for other applications of tightening a strap, cord, chain, rope, or other elongated flexible material.

SUMMARY

Assemblies, devices, apparatuses, and methods are provided for use in tightening of a strap or other elongated flexible material.

In various embodiments, a twisting assembly is provided, the twisting assembly including:
(A) a base part, wherein:
  the base part has a plurality of teeth arranged in a circle; and
(B) a twisting part, wherein:
  (1) the twisting part is adapted for rotating adjacent to and relative to the base part; and
  (2) the twisting part has a windlass portion, wherein a portion of an elongated flexible material can be operatively connected to the windlass portion such that when the windlass portion is rotated, the portion of the elongated flexible material is twisted;
wherein the twisting part is adapted to cooperatively allow movement of the twisting part away from close engagement with the teeth of the base part to allow rotation of the twisting part in one rotational direction relative to the base part; and
wherein the twisting part is adapted to cooperatively allow movement of the twisting part into close engagement with the teeth of the base part to prevent rotation of the twisting part in the opposite rotational direction relative to the base part.

In various embodiments, a twisting assembly is provided, the twisting assembly including:
(A) a base part, wherein:
  the base part has a plurality of teeth arranged in a circle; and
(B) a twisting part, wherein:
  (1) the twisting part is adapted for rotating adjacent to and relative to the base part;
  (2) the twisting part has at least a windlass portion, wherein a portion of an elongated flexible material can be operatively connected to the windlass portion such that when the windlass portion is rotated, the portion of the elongated flexible material is twisted; and
  (3) the twisting part has a plurality of teeth arranged in a circle;
wherein the twisting part is adapted to cooperatively allow movement of the teeth of the twisting part away from close engagement with the teeth of the base part to allow rotation of the twisting part in one rotational direction relative to the base part; and
wherein the twisting part is adapted to cooperatively allow movement of the teeth of the twisting part into close engagement with the teeth of the base part to prevent rotation of the twisting part in the opposite rotational direction relative to the base part.

A twisting assembly according to this disclosure can be used in a variety of applications. An example of an application of a twisting assembly according to this disclosure is in a tourniquet. As can be seen from the operation in the embodiments for tourniquet applications, such a twisting assembly shortens the length of a strap or cord or other elongated material by rotating between two fixed or predetermined points and either shortening that distance or creating more tension between the points as the strap or cord or other elongated flexible material is twisted. Other uses could include anything that requires the need to tighten a strap or cord or other elongated flexible material between two points, such as between two anchor points. In various embodiments, one or both ends of the elongated flexible material can have an attachment device, such as a hook or buckle, which can be used, for example, for attaching an end to an anchoring point or for attaching the ends to each other. The device needs to be a simple mechanism that has few moving parts and few parts to break or malfunction. The device is also inexpensive and impervious to most weather conditions. Unlike rachets with pawls and other devices that require metal parts or that have more complex designs and multiple areas for potential failure, a twisting assembly according to this disclosure is two parts currently made of nylon, but could be any suitable structural material depending on the need of the intended application. In addition to an application for tightening of a tourniquet, example applications include, without limitation:
(a) Securing items such as cargo or equipment for transport, for example, as in to be restrained in the bed of a vehicle;
(b) Securing something to be held together, for example, as in a bunch of cloth or other flexible material;

(c) Securing multiple items together, for example, as in a bundle;
(d) Winching to move or load cargo, such as moving material or cargo from one level to a another, e.g., helping to move something from first floor to the second floor;
(e) Tightening back packs or supply packs for adjusting the fit on a person or animal; and
(f) Tightening the tension on straps, cords, chains, or ropes.

In addition to an application in a tourniquet, other example devices or systems include, without limitation:
(a) Tie-downs or cinches for holding cargo or equipment;
(b) Bag closing straps (for example, similar to elastic cinches);
(c) Strapping systems for securing items together, as in a bundle;
(d) Pulley systems for moving cargo, equipment, or other items from one level to a another (such as moving something from a first floor to a second floor of a building);
(e) Harness restraint systems, such as seat belts; and
(f) Temporarily adjustable tensioners on straps, cords, chains, or ropes, such as for use with tents or other temporary structures.

These and other aspects, embodiments, and advantages of the disclosed inventions will be apparent to one skilled in the art upon reading the following detailed description. While the disclosure is susceptible to various modifications and alternative forms, specific embodiments thereof will be described in detail and shown by way of example. It should be understood, however, that the detailed description is not intended to limit the disclosure to the particular forms disclosed.

Detailed embodiments and examples according to the principles of the inventions are disclosed herein. However, specific portions or functional details disclosed herein are merely representative for purposes of describing example embodiments. Example embodiments can be embodied in many alternate forms and should not be construed as limited to only the embodiments set forth herein. Example embodiments are capable of various modifications, equivalents, and alternatives.

BRIEF DESCRIPTION OF THE DRAWING

The accompanying figures of the drawing are incorporated into the specification to help illustrate examples according to various embodiments of the disclosure. Like references are used for like elements or features throughout the figures of the drawing. It should be understood that the figures of the drawing are not necessarily to scale.

These figures together with the description serve to explain the general principles of the disclosure. The figures are only for the purpose of illustrating preferred and alternative examples of how the various aspects of the claimed inventions can be made and used and are not to be construed as limiting the claimed inventions to only the illustrated and described examples. Various advantages and features of the various aspects of the present inventions will be apparent from a consideration of the drawing.

Figure 3:
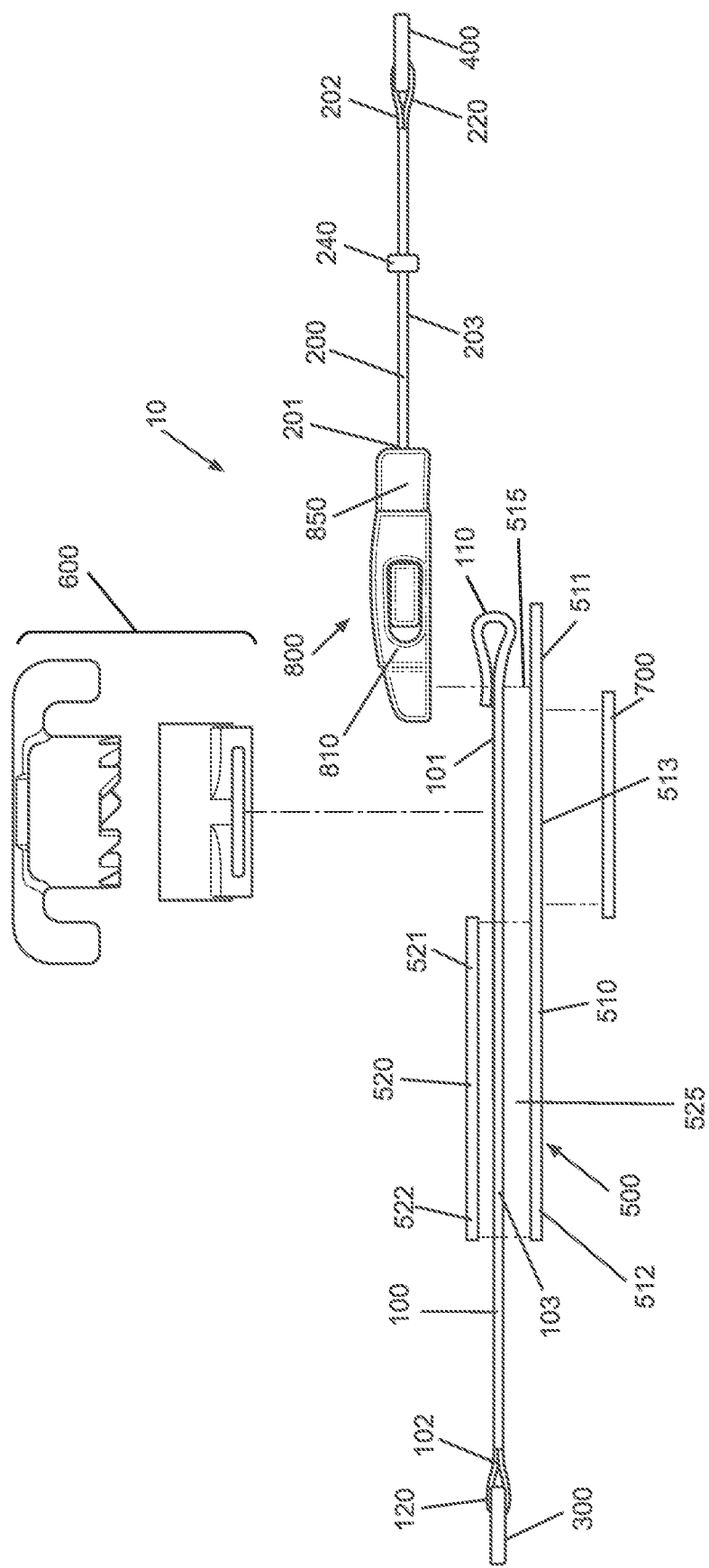

In some alternative embodiments, the functions or acts can occur out of the order noted in the figures. For example, two figures of the drawing shown in succession can in fact be executed substantially concurrently or can sometimes be executed in the reverse or order, depending upon the functionality or acts involved.

FIG. 1 is a right side perspective view of a tourniquet 10 according to an embodiment of the disclosure, wherein the tourniquet 10 is shown in an unbuckled condition. As will hereinafter be described in detail, the tourniquet 10 includes a tightening strap 100 having a first end 101 and a second end 102, a cinch strap 200 having a first end 201 and a second end 202, a strap keeper 240, a first D-ring 300 attached to the second end 102 of the tightening strap 100, a second D-ring 400 attached to the second end 202 of the cinch strap 200, a pad assembly 500 positioned with a portion of the tightening strap 100, a twisting assembly 600 for twisting the tightening strap 100, a holding strap 700 for holding the twisting assembly 600 in a fixed position on the pad assembly 500, and a buckle 800 having a female part 810 connected to the pad assembly 500 and a male part 830, wherein the male part has a strap adjuster 850 operatively connected to the cinch strap 200.

FIG. 2 is a right side perspective of the tourniquet 10 substantially as illustrated in FIG. 1, but wherein the tourniquet 10 is shown in a buckled condition, whereby the tourniquet 10 forms a loop, referred to as tourniquet loop 52, which tourniquet loop 52 can be positioned to encircle a limb as hereinafter described in detail regarding FIGS. 28-31.

FIG. 3 is an exploded right side view diagram of the general arrangement of parts in the tourniquet 10 illustrated in FIGS. 1 and 2 (but not to the scale of FIGS. 1 and 2), except in a linear position and wherein the holding strap 700 is in an open, unfolded position (as will hereinafter be described in detail).

FIG. 4 is an oblique upper side perspective view of the twisting assembly 600, showing a base part 610 and a twisting part 650.

FIG. 5 is an oblique under side perspective view of the twisting assembly 600, showing the base part 610 and the twisting part 650.

FIG. 6 is an exploded end elevation view of the twisting assembly 600, showing the base part 610 and the twisting part 650.

FIG. 7 is an exploded side elevation view of the twisting assembly 600, showing the base part 610 and the twisting part 650.

Figure 8:
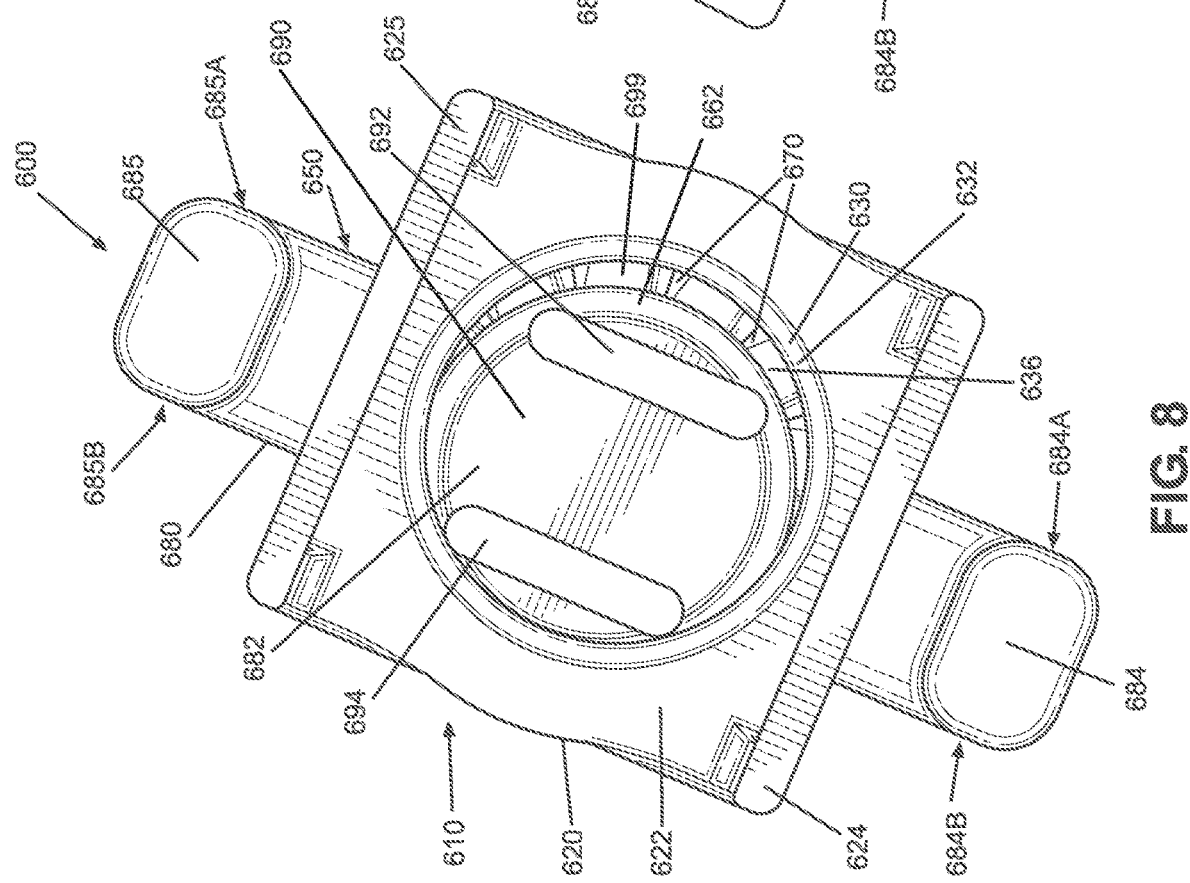

FIG. 8 is a bottom top plan view of the twisting assembly 600, showing the base part 610 and the twisting part 650.

Figure 9:
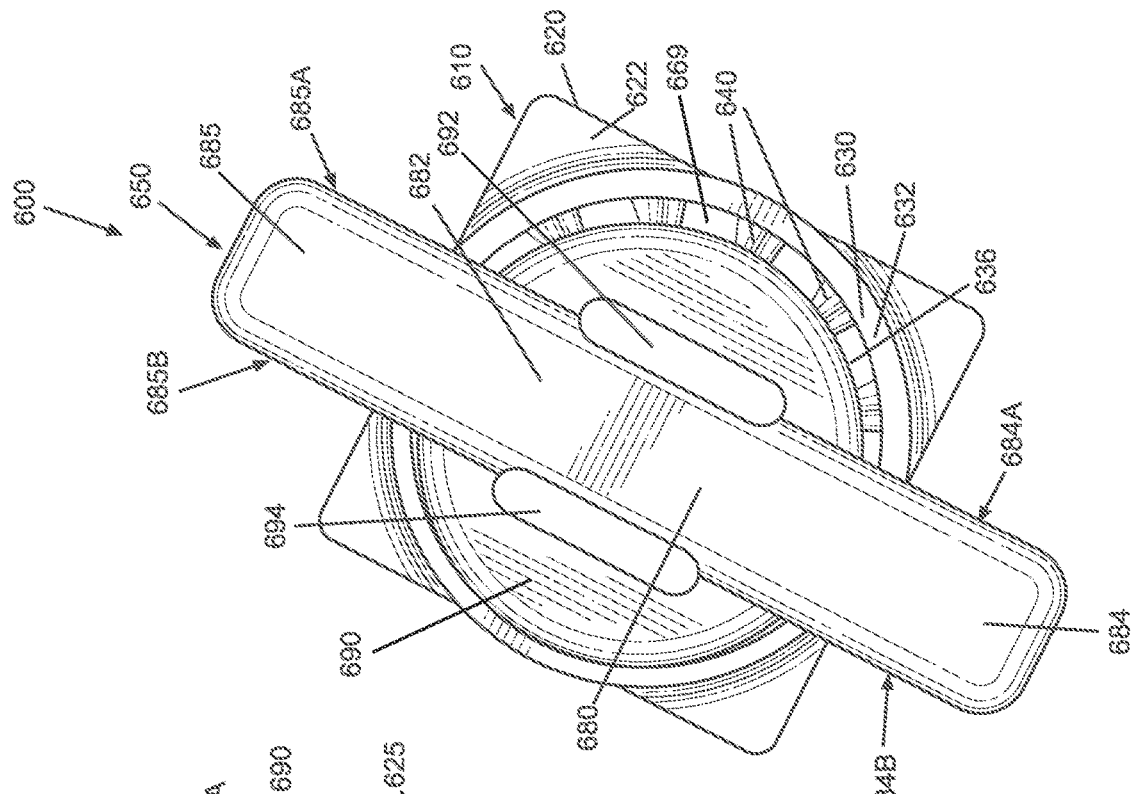

FIG. 9 is a top plan view of the twisting assembly 600, showing the base part 610 and the twisting part 650.

FIG. 10 is a bottom plan view of the twisting part 650.

FIG. 11 is an oblique under side perspective view of the twisting part 650.

Figure 12:
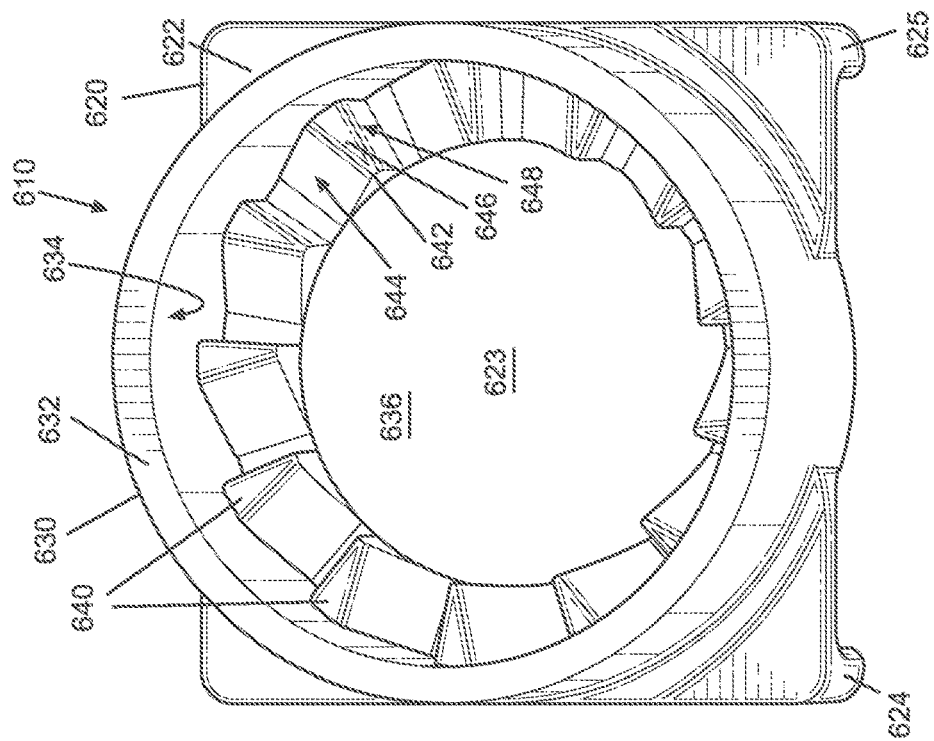

FIG. 12 is an oblique upper side perspective view of the base part 610.

Figure 13:
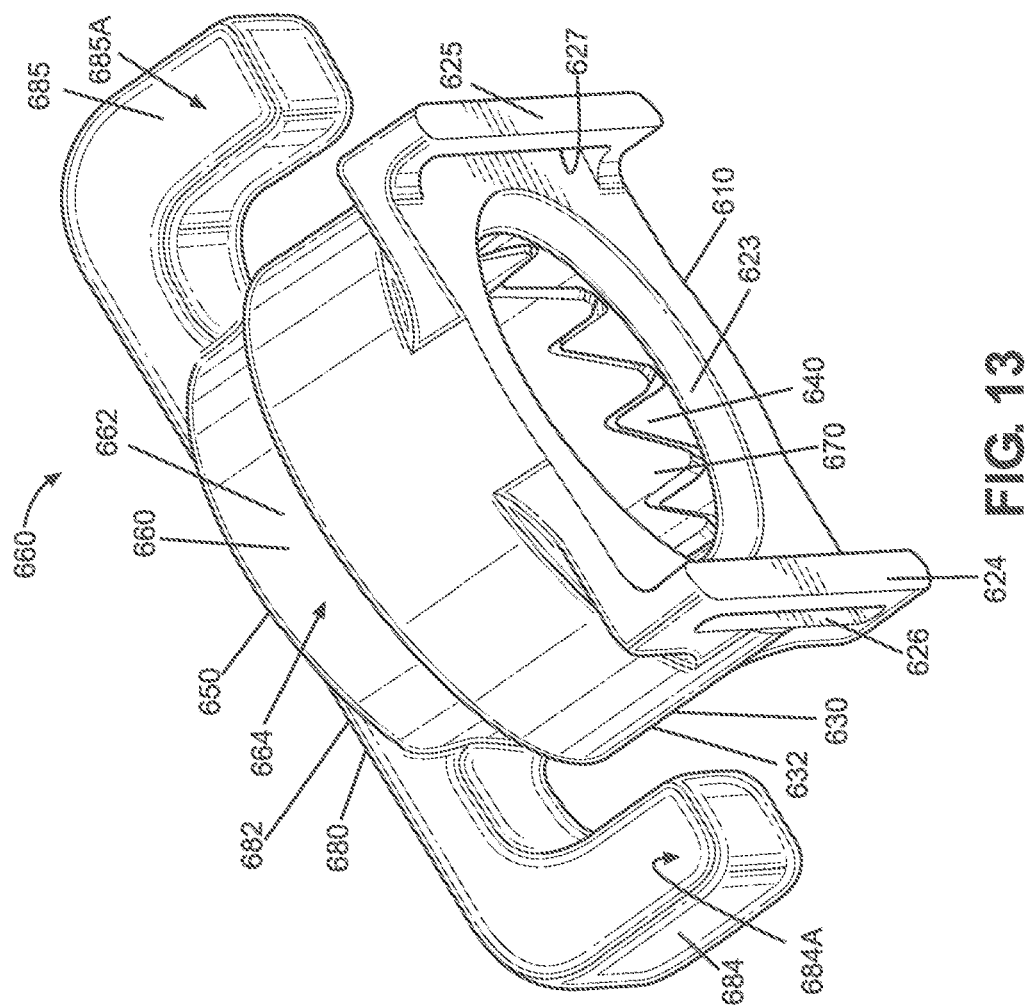

FIG. 13 is an oblique under side perspective view of the twisting assembly 600, illustrating the base part 610 and the twisting part 650 in a fully engaged condition.

FIG. 14 is an exploded left side perspective view showing the threading of a portion of the tightening strap 100 through the base part 610 and the twisting part 650 of the twisting assembly 600, wherein the base part 610 is shown attached to the pad 510 with the holding strap 700 for holding the base part 610 of the twisting assembly 600 onto the pad 510 and preventing the base part 610 from twisting relative to the pad 510.

FIG. 15 is a left side perspective view similar to FIG. 14, but not exploded.

Figure 16:
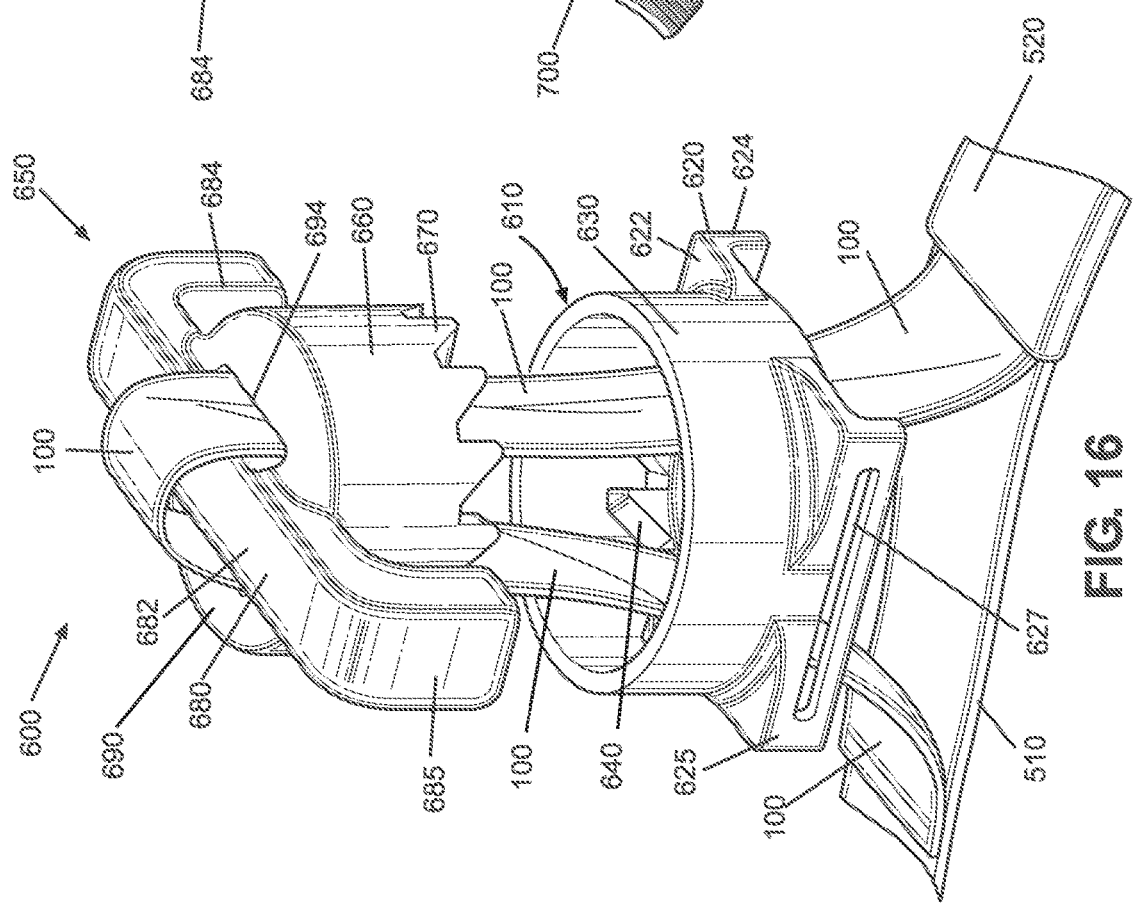

FIG. 16 is an exploded left side perspective view similar to FIG. 15 showing the threading of the tightening strap 100 through the base part 610 and the twisting part 650 of the twisting assembly 600, but without the holding strap 700 to better view the left side holding strap slot 627 in the saddle portion 620 of the base part 610.

Figure 17:
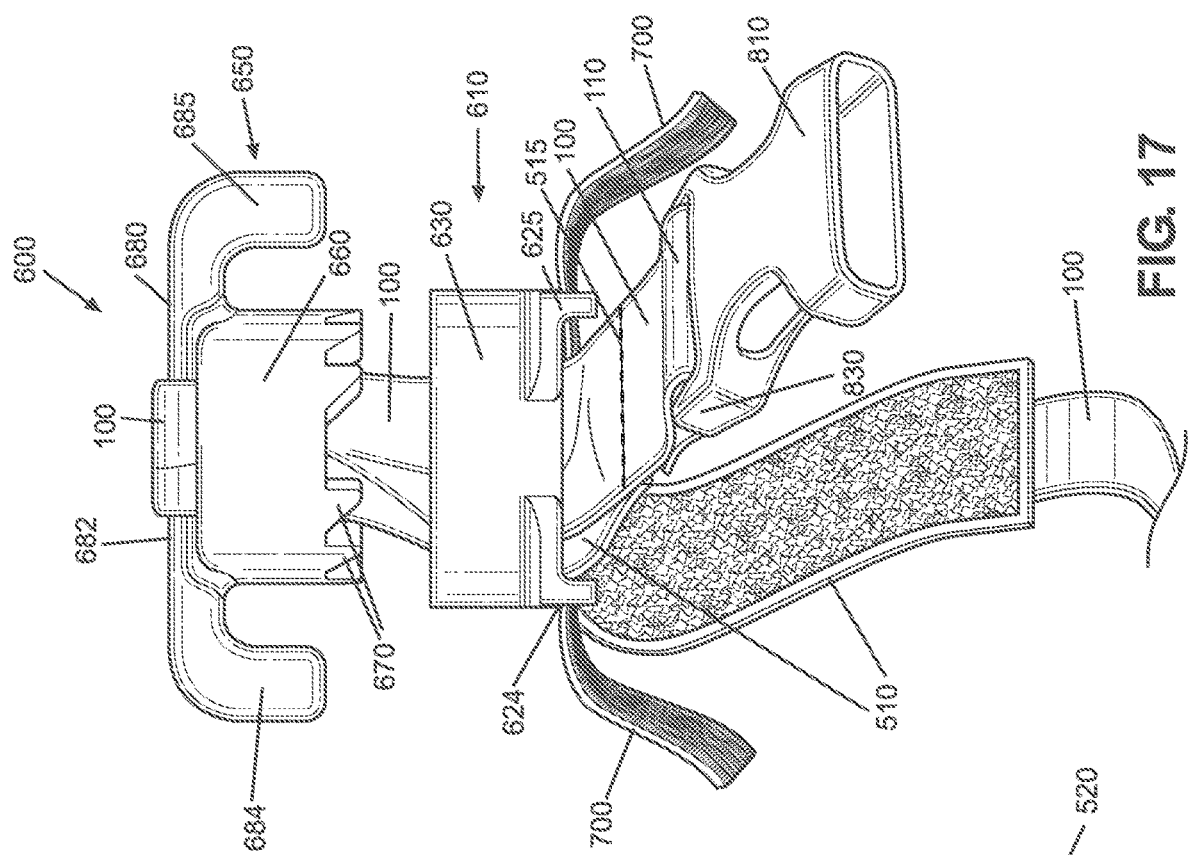

FIG. 17 is an exploded right-end perspective view similar to FIG. 16 illustrating the holding strap 700 threaded through the slots 626 and 627 (not visible in this figure) of the right side and left side walls 624 and 625 of the saddle portion 620 of the base part 610 of the twisting assembly 600.

Figure 18:
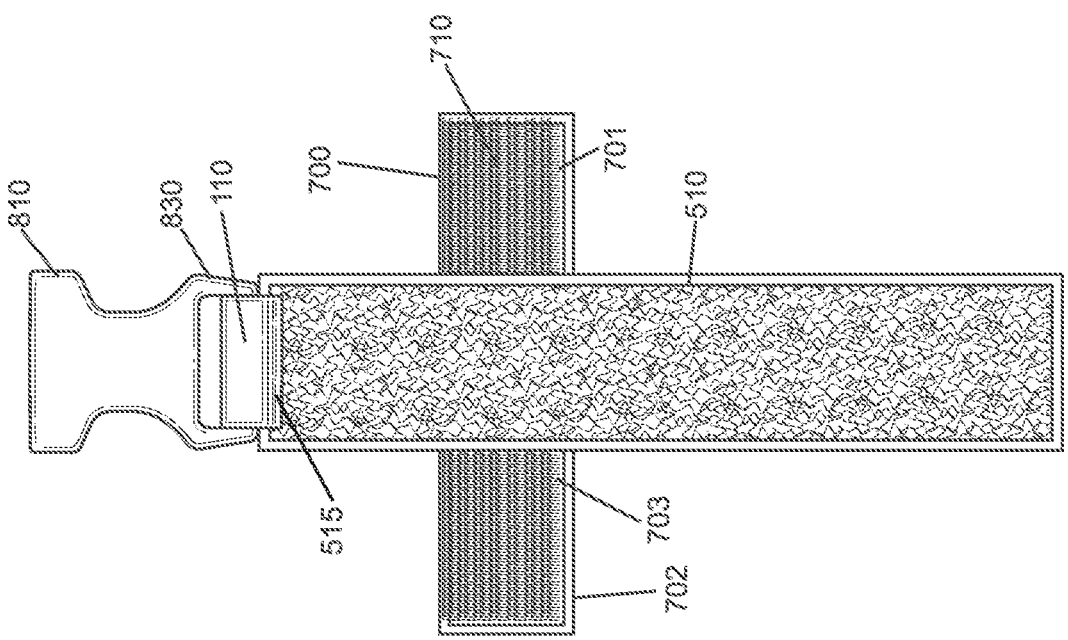

FIG. 18 is an under side perspective view illustrating the holding strap 700 over the pad assembly 500, wherein a first end 701 and a second end 702 of the holding strap 700 are shown in an open, unfolded position, and wherein a middle portion 703 of the holding strap is underneath the pad 510, as in a step in attaching the holding strap 700 to the pad 510.

Figure 19:
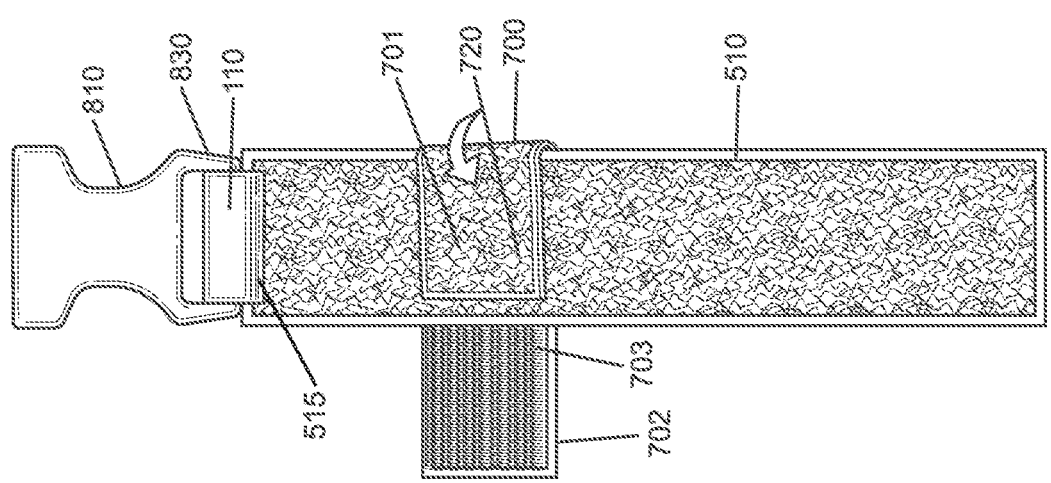

FIG. 19 is an under side perspective view illustrating the holding strap 700 over the pad assembly 500, similar to FIG. 18 but wherein the first end 701 of the holding strap 700 is shown in a closed, folded portion around a portion of the pad assembly 500 and wherein the second end 702 of the holding strap 700 is shown in an open, unfolded position, as in a further step in attaching the holding strap 700 to the pad 510.

Figure 20:
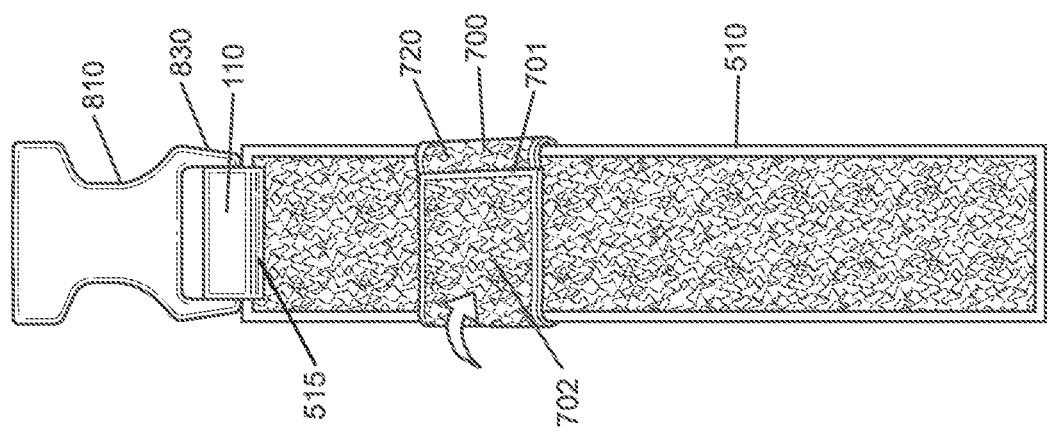

FIG. 20 is an under side perspective view illustrating the holding strap 700 over the pad assembly 500, similar to FIGS. 18 and 19 but wherein the first end 701 of the holding strap 700 is shown in a folded portion around a portion of the pad assembly 500 and wherein the second end 702 of the holding strap 700 is shown in a closed, folded position, as in a further step in attaching the holding strap 700 to the pad 510.

FIG. 21 is a under end perspective view illustrating the holding strap 700 (with hook-and-loop fastener, for example, VELCRO brand) and with both the first end 701 and the second end 702 shown folded under the pad 510, in a position similar to that of FIG. 20.

FIG. 22 is a right side elevation view of the female part 810 (of buckle 800 not shown as a whole in this figure) attached to the first end 101 of tightening strap 100.

FIG. 23 is a top plan view of the female part 810 (of buckle 800 not shown as a whole in this figure) attached to the first end 101 of tightening strap 100.

FIG. 24 is a under right side perspective view of the male part 850 (of buckle 800 not shown as a whole in this figure). In the illustrated embodiment of the male part 850, the one-way strap adjuster 860 is integrally formed with the male part 850.

FIG. 25 is a bottom perspective view of the male part 850 (of buckle 800 not shown as a whole in this figure) attached to a first end 201 of the cinch strap 200.

Figure 26:
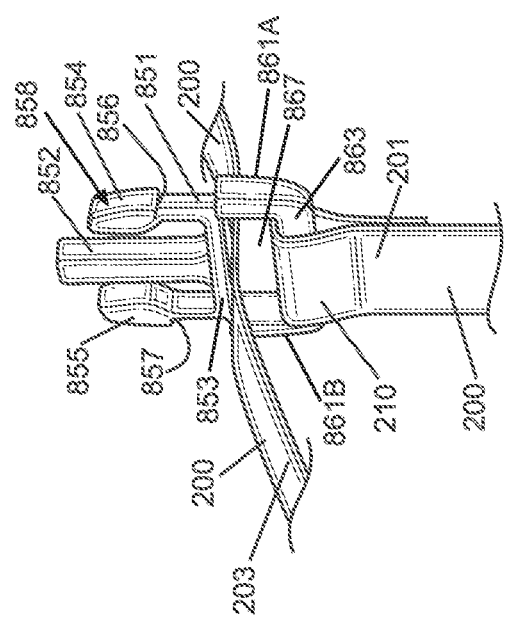

FIG. 26 is a under right side perspective view of a male part 851 (of a buckle 800 not shown as a whole in this figure). In the illustrated embodiment of the male part 851 illustrated in FIG. 26, the male part 851 is similar to the male part 850 illustrated in FIGS. 24-24, except the one-way strap adjuster 860 is not included.

Figure 27:
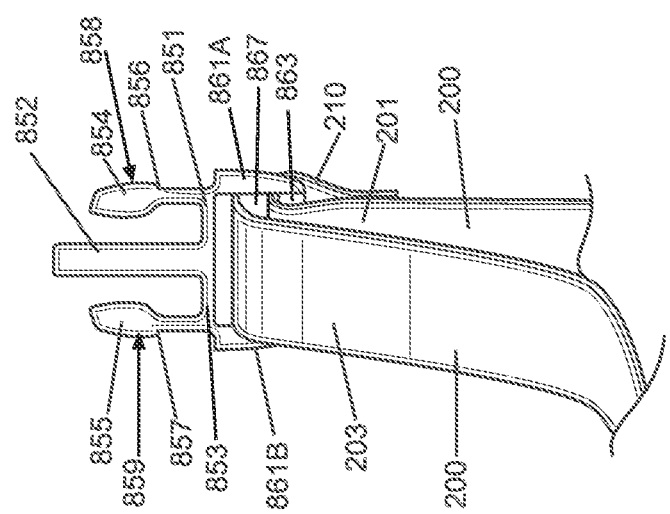

FIG. 27 is a bottom perspective view of the male part 851 (of buckle 800 not shown as a whole in this figure) attached to a first end 201 of the cinch strap 200.

FIG. 28 is an oblique right side perspective view of the tourniquet 10 in a condition of being positioned and buckled but loose around the thigh of a human leg L. The buckle 800 of the tourniquet 10 is connected by holding or pushing the female part 810 in the direction of arrow A and holding or pushing the male part 850 in the direction of arrow B so that the female part 810 and male part 850 engage together to form a buckled connection with the tourniquet 10 around the limb L.

FIG. 29 is an oblique right side perspective view of the tourniquet 10 in a condition of having been buckled and the second end 202 of the cinch strap 200 being pulled in the direction of arrow C to cinch the tourniquet around the thigh of a human leg L. The taut condition of tourniquet 10 caused by a cinching with the cinch strap 200 is usually not sufficiently tight, however, to substantially restrict blood flow to the limb L past the position of the tourniquet 10.

Figure 30:
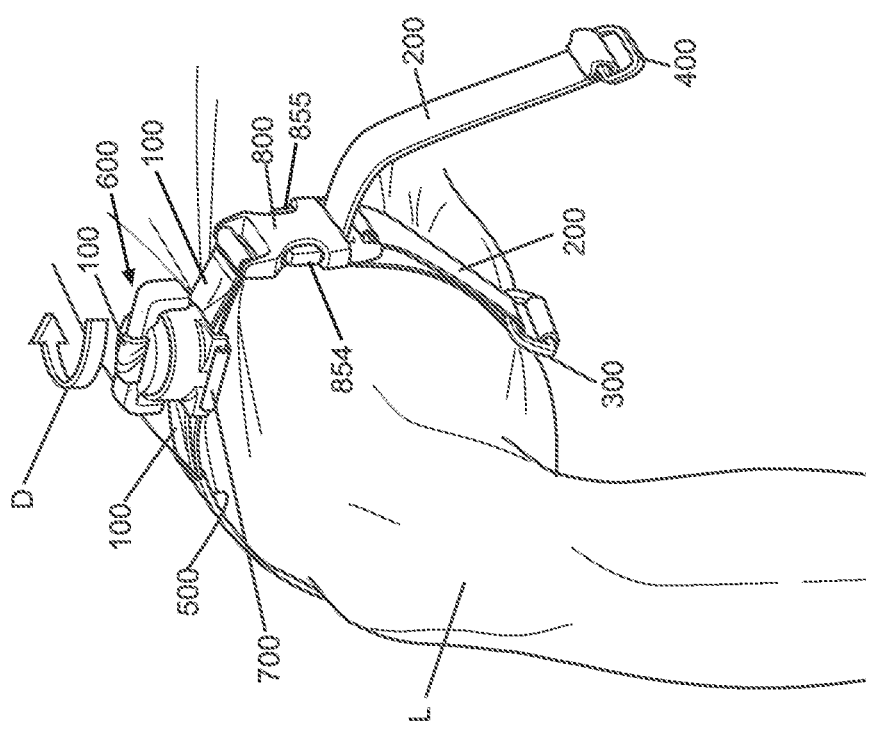

FIG. 30 is an oblique right side perspective view of the tourniquet 10 in a condition of being buckled and fully cinched taut around the thigh of a human leg L and further in a process of being tightened by turning of the twisting part 650 of the twisting assembly 600 in the clockwise direction of arrow D. The twisting assembly 600 can be used to tighten the tourniquet 10 until blood flow to the limb L is adequately restricted or stopped.

Figure 31:
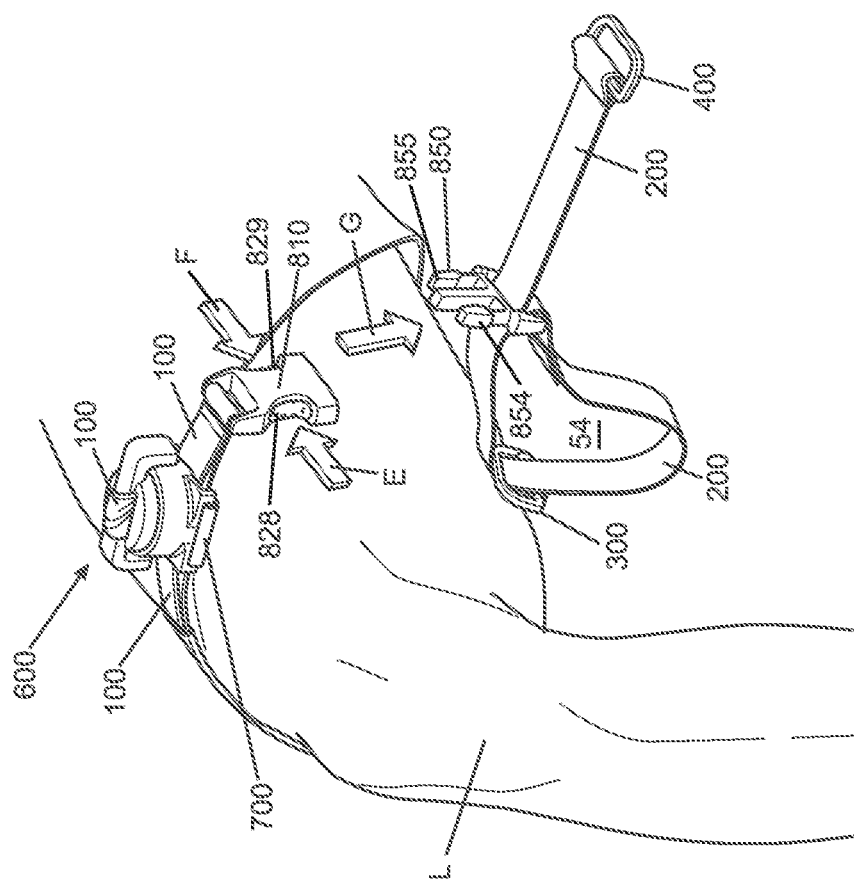

FIG. 31 is an oblique right side perspective view of the tourniquet 10 in a condition of being unbuckled and released from previously being tightly applied around the thigh of a human leg L. To unbuckle and release the tourniquet 10, the releasing finger surfaces 858 and 859 of the buckle 800 are manually pushed toward each other in the directions of arrows E and F with the thumb and finger of a hand, whereby when the buckle is released, the male part 850 of the buckle 800 is released in the direction of arrow G from the female part 810 of the buckle, thereby releasing the tourniquet 10 from around the limb L.

FIG. 32 is an exploded right side view diagram of the general arrangement of parts in a second embodiment of a tourniquet 20 according to the disclosure, similar to the first embodiment illustrated in FIG. 3 with an embodiment of a pad assembly 550 (which is different from the embodiment of the pad assembly 500 in FIGS. 1-25), wherein the tourniquet 20 is shown in a substantially open, unbuckled linear position and wherein the holding strap 700 is in an open, unfolded position. In this embodiment of the tourniquet 20, the tightening strap 100 additionally includes a stop 130, which helps in the initial positioning of a middle portion of the tightening strap 100 through the twisting assembly 600.

FIG. 33 is an exploded right side view diagram of the general arrangement of parts in a third embodiment of a tourniquet 30 according to the disclosure, similar to the second embodiment illustrated in FIG. 32, wherein the tourniquet 30 is shown in a substantially open, unbuckled linear position and having a square loop 330 instead of a D-ring 300 as in the second embodiment and having a different embodiment of a twisting assembly 900 instead of the twisting assembly 600 as in the second embodiment illustrated in FIG. 32.

Figure 34:
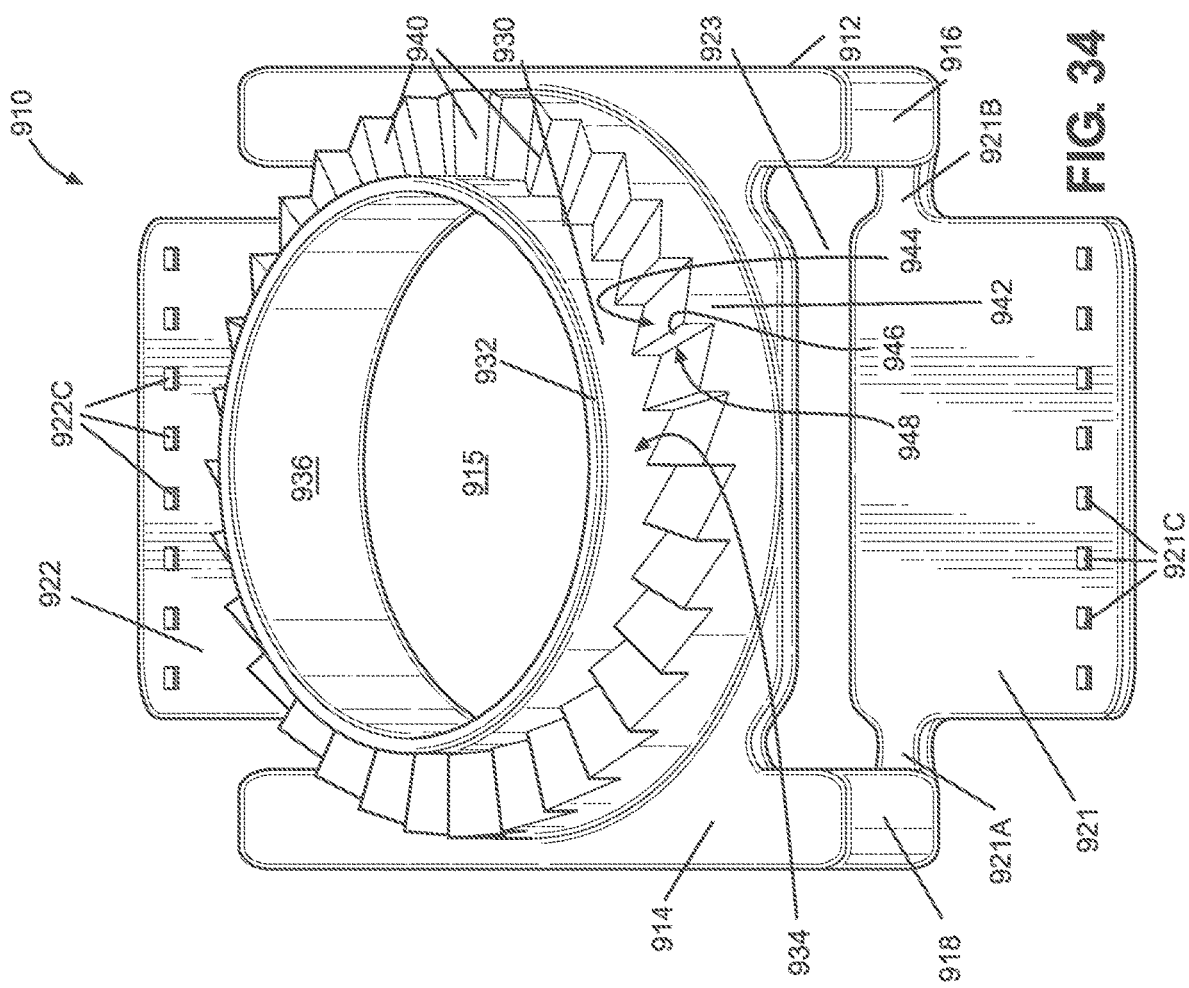

FIG. 34 is an oblique upper side and end perspective view of the base part 910.

Figure 35:
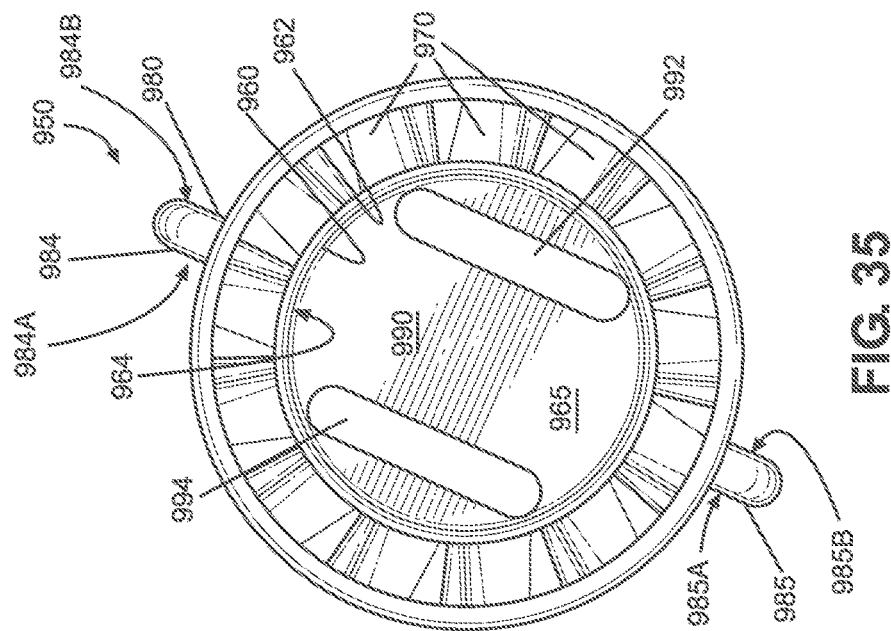

FIG. 35 is a bottom plan view of the twisting part 950.

Figure 36:
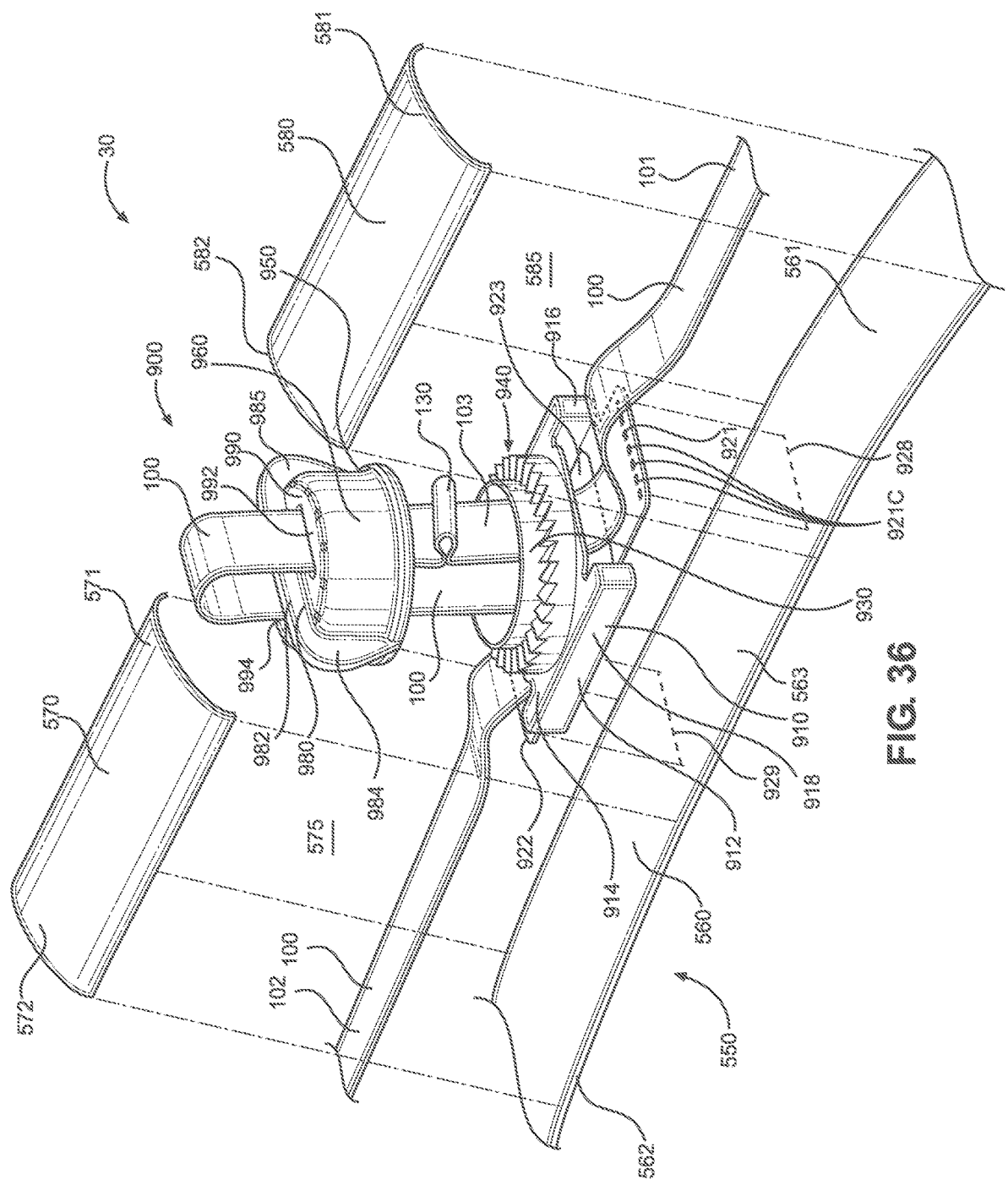

FIG. 36 is an exploded left side perspective view of a portion of the tourniquet 30 showing an exploded view of the pad assembly 550, an exploded view of the twisting assembly 900 positioned to be attached to the pad 560 of the pad assembly 550, and showing the twisting strap 100 threaded through the sleeves 575 and 585 of the pad assembly 550 and through the twisting assembly 900.

Figure 37:
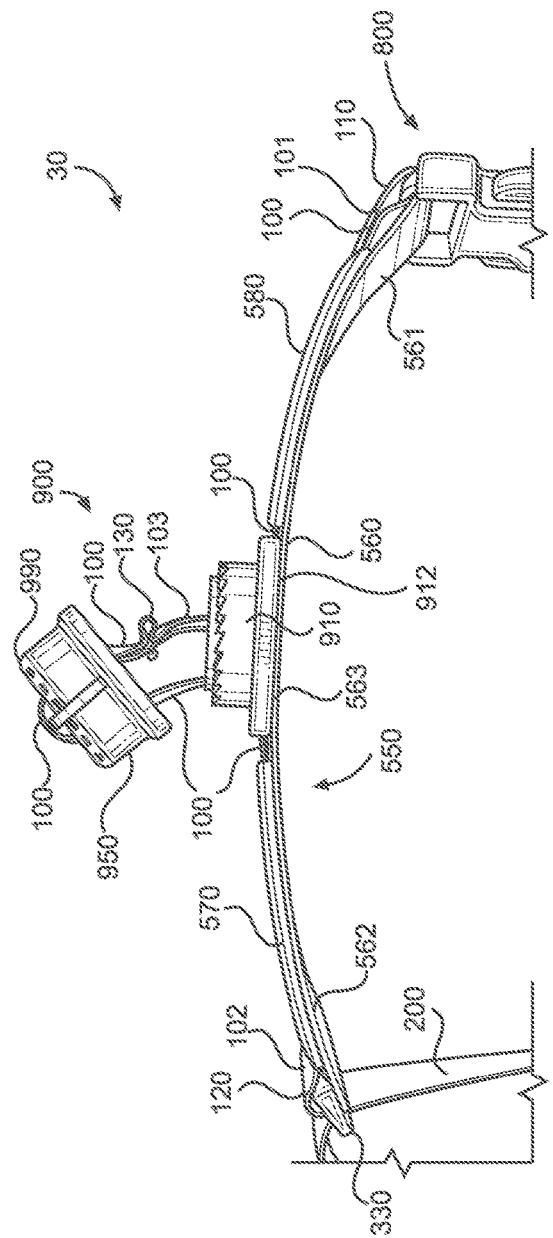

FIG. 37 is a left side perspective view of a portion of the tourniquet 30 showing the pad assembly 550 and twisting assembly 900 operatively connected between the buckle 800 and the square loop 330, wherein the twisting part 950 is separated or pulled away from the base part 910.

Figure 38:
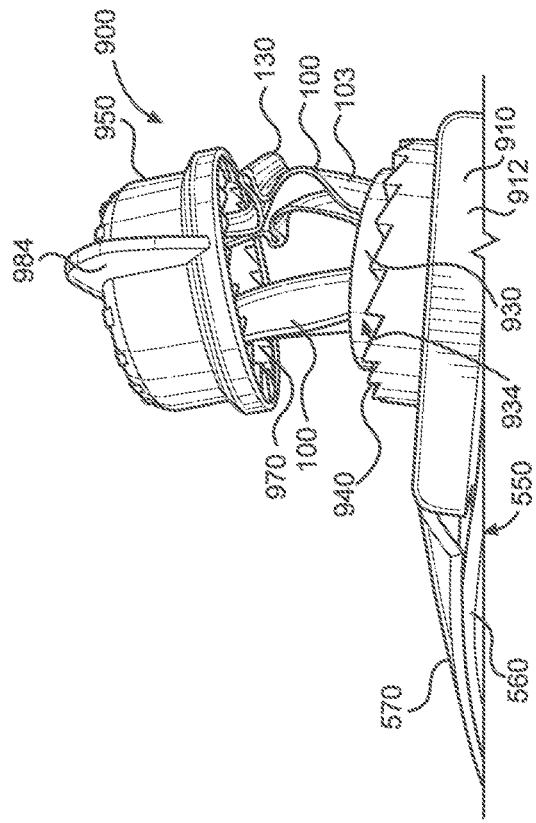

FIG. 38 is a left side and obliquely upward perspective view of a detail portion of the twisting assembly 900, wherein the twisting part 950 is separated or pulled away from the base part 910 such that the interior and under side of the twisting part 950 is partially visible.

FIG. 39 is another is a left side and obliquely upward perspective view of a detail portion of the twisting assembly 900, wherein the twisting part 950 is separated or pulled away from the base part 910 such that the interior and under side of the twisting part 950 is partially visible.

FIG. 40 is a left side and downward perspective view of a detail portion of the twisting assembly 900, wherein the twisting part 950 is separated or pulled away from the base part 910 such that the interior and upper side of the base part 910 is partially visible.

Figure 41:
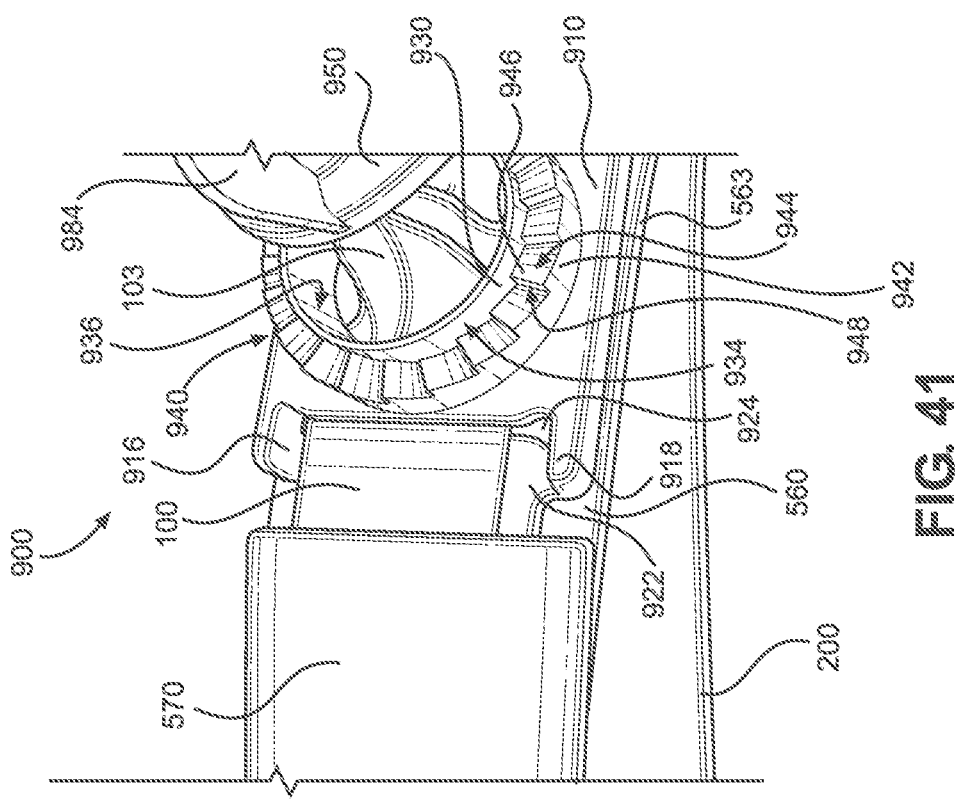

FIG. 41 is an downward perspective view of a detail portion of the twisting assembly 900 shown from the end of the square loop 330 (not shown in FIG. 41), wherein the twisting part 950 is separated or pulled away from the base part 910 such that the interior and upper side of the base part 910 is partially visible.

Figure 42:
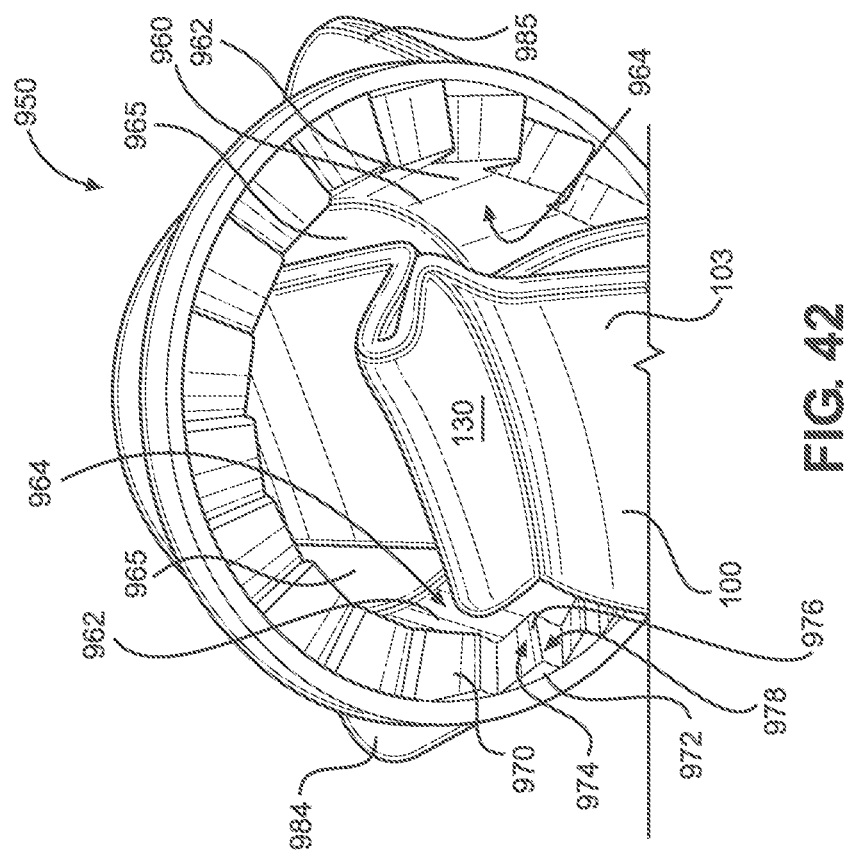

FIG. 42 is an upward oblique perspective view of a detail portion of the twisting part 950, wherein the twisting part 950 is pulled away from the base part 910 (not shown in FIG. 32) to further illustrate the stop 130 of the twisting strap 100.

Figure 43:
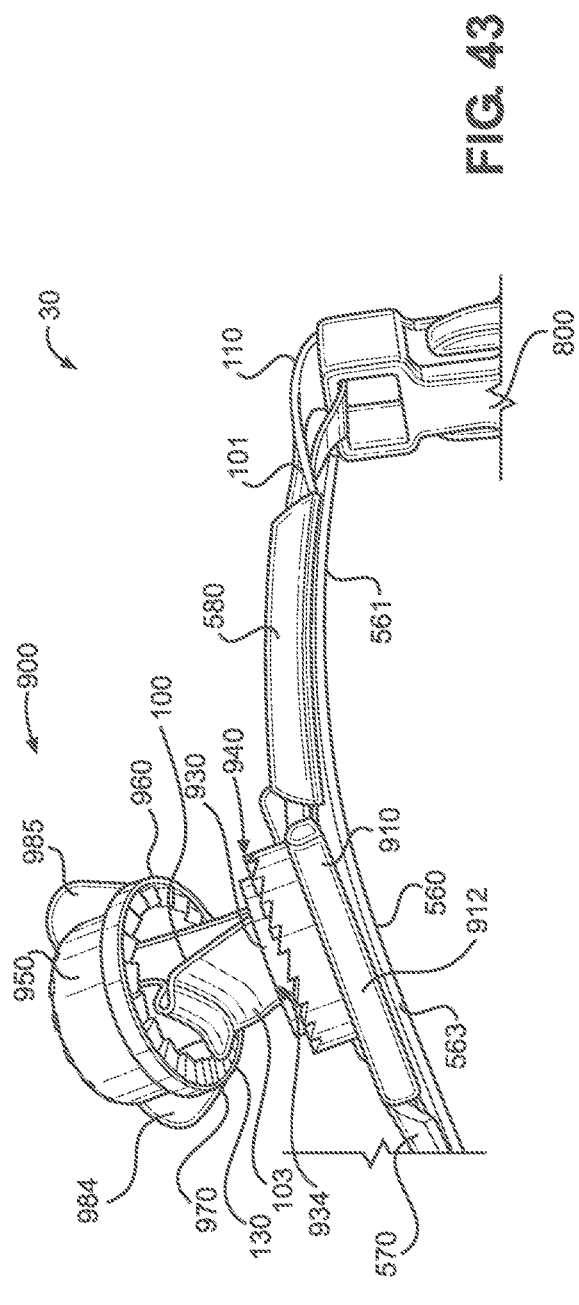

FIG. 43 is a left side obliquely upward perspective view of a portion of the tourniquet 30, wherein the twisting part 950 is separated or pulled away from the base part 910 and showing the connection of the tightening strap 100 to the buckle 800.

Figure 44:
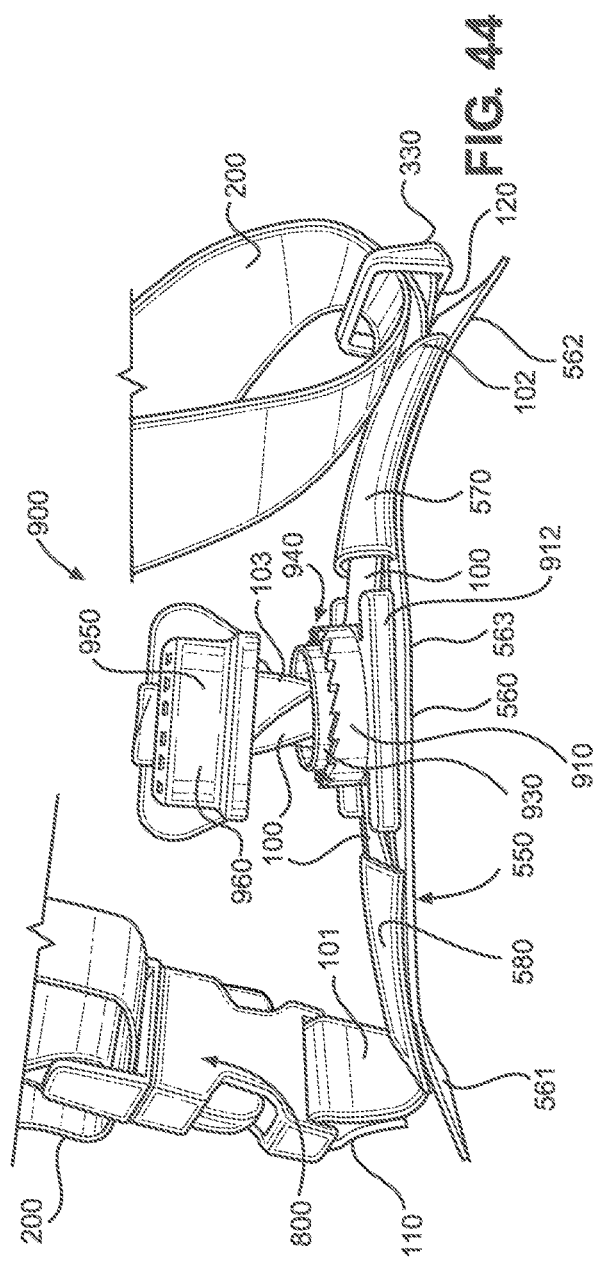

FIG. 44 is a right side perspective view of a portion of the tourniquet 30, wherein the twisting part 950 is separated or pulled away from the base part 910 and showing the attachments of the tightening strap 100 pulled upward to show another view of the attachments to the loop 330 and the buckle 800.

FIG. 45 is an oblique upper side perspective view of a fourth embodiment of a portion of a tourniquet 40 according to the disclosure, wherein the tourniquet 40 is similar to the tourniquet 30 illustrated in FIGS. 33-44 except wherein the tourniquet 40 has a twisting assembly 1000 (instead of the twisting assembly 900), wherein the twisting assembly 1000 includes a base part 1010 attached to the pad assembly 550 and a twisting part 1050 attached to the twisting strap 100.

FIG. 46 is an end view of the twisting assembly 1000 attached to the pad assembly 550.

FIG. 47 is a top plan view of the twisting assembly 1000 attached to the pad assembly 550.

FIG. 48 is an oblique upper side view perspective of the twisting assembly 1000 illustrating how the base part 1010 can be used to lock the twisting part 1050 against untwisting, wherein for clarity of the illustration the twisting strap 100 is not shown.

FIG. 49 is an oblique upper side perspective view of a portion of a fifth embodiment of a tourniquet 50 according to the disclosure, wherein the tourniquet 50 is similar to the tourniquet 30 illustrated in FIGS. 33-44 except wherein the tourniquet 50 has a twisting assembly 1100 (instead of the twisting assembly 900), wherein the twisting assembly 1100 includes a base part 1110 attached to the pad assembly 550 and a twisting part 1150 attached to the twisting strap 100.

FIG. 50 is an end view of the twisting assembly 1100 attached to the pad assembly 550.

FIG. 51 is a top plan view of the twisting assembly 1100 attached to the pad assembly 550.

FIG. 52 is an oblique upper side view perspective of the twisting assembly 1100 illustrating how the base part 1110 can be used to lock the twisting part 1150 against untwisting, wherein for clarity of the illustration the twisting strap 100 is not shown.

Figure 53:
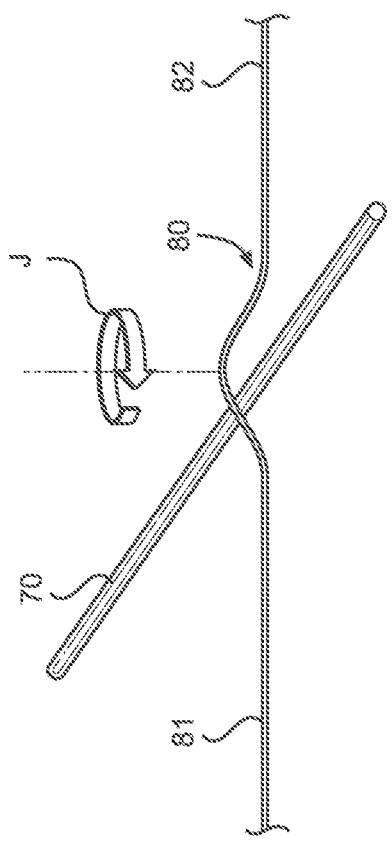

Referring to FIG. 53, in a simple form, an example of a Spanish windlass 70 is a rod or wooden stick. The Spanish windlass 70 (often referred to simply as a "windlass") is positioned adjacent to a rope 80 having ends 81 and 82, as illustrated in FIG. 53, and the windlass 70 is rotated about arrow J, that is, about an axis generally perpendicular to the overall length of the rope 80 between the two rope ends 81 and 82. The rope ends 81 and 82 of the rope 80 can be tied to other objects (not shown in FIG. 45). If desired, the direction of rotation can be the opposite direction of arrow J, as the direction makes no difference to the principle of operation of a Spanish windlass.

Figure 54:
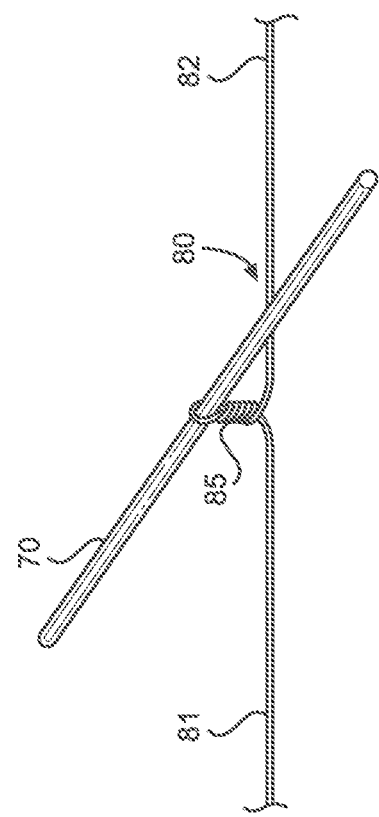

FIG. 54 is an illustration of the Spanish windlass 70 of FIG. 53 wherein the turning of the windlass 70 has twisted the rope 80 to have a twisted portion 85. The twisting of the rope 80 about itself to have the twisted portion 85 shortens the overall length of the rope 80 between the two ends 81 and 82, which shortening can be used to draw and tighten the two ends 81 and 82 of the rope 80 tightly together. The windlass 70 should be held against untwisting of the twisted portion 85 of the rope, which can have substantial potential energy for untwisting. For example, the windlass 70 can be tied down to an end of the rope with a lashing 90. Of course, the Spanish windlass 70 and the rope 80 should be sufficiently strong for the particular purpose of use.

DETAILED DESCRIPTION AND EXAMPLES

A tourniquet 10 according to an embodiment of the disclosure is illustrated in FIGS. 1-3.

FIG. 1 is a right side perspective view of a tourniquet 10 according to an embodiment of the disclosure, wherein the tourniquet 10 is shown in an unbuckled condition. As will hereinafter be described in detail, the tourniquet 10 includes a tightening strap 100 having a first end 101 and a second end 102, a cinch strap 200 having a first end 201 and a second end 202, a strap keeper 240, a first D-ring 300 attached to the second end 102 of the tightening strap 100, a second D-ring 400 attached to the second end 202 of the cinch strap 200, a pad assembly 500 positioned with a portion of the tightening strap 100, a twisting assembly 600 for twisting the tightening strap 100, a holding strap 700 for holding the twisting assembly 600 in a fixed position on the pad assembly 500, and a buckle 800 having a female part 810 connected to the pad assembly 500 and a male part 830, wherein the male part has a strap adjuster 850 operatively connected to the cinch strap 200.

FIG. 2 is a right side perspective of the tourniquet 10 substantially as illustrated in FIG. 1, but wherein the tourniquet 10 is shown in a buckled condition, whereby the tourniquet 10 forms a loop, referred to as tourniquet loop 52, which tourniquet loop 52 can be positioned to encircle a limb as hereinafter described in detail regarding FIGS. 28-31.

Regarding the views of the figures in the drawing, relative position terms such as "side," "upper," "lower," "upward," "downward," "top," "bottom," "central," "over," "under," and similar terms are made with reference to the orientation of the embodiment of the tourniquet 10 as shown in FIG. 1-2 (or what would be similar orientations for the embodiment of the tourniquet 20 illustrated in FIG. 32 or the embodiment of tourniquet 30 illustrated in FIG. 33), unless the specific context otherwise requires.

Regarding the views of the figures in the drawing, as used herein, an "end" can be with reference to an end portion of a strap or other elongated element or it can be with reference to a view of a figure that is toward an end of a strap or other structural element. Such relative position terms are for purposes of convenient and consistent reference to the structural elements in all the different views of the figures and, unless the context otherwise requires, not limiting and are not part of the name of an element, function, or step.

In the embodiment of the tourniquet shown in FIGS. 1-2, except for the twisting assembly 600, the tourniquet 10 can be positioned in a tourniquet loop 52 as illustrated in FIG. 2 to be generally symmetrical about a plane that bisects the length of the pad assembly 500 of the tourniquet 10. Accordingly, the view from the "side" of the tourniquet 10 in FIGS. 1-2 is arbitrarily referred to as from the "right" side, where the buckle female part 810 of the buckle 800 is viewed to the right "side" of the adjacent pad assembly 500 and the twisting assembly 600, unless the specific context otherwise requires. Except for the twisting assembly 600, the tourniquet 10 is substantially symmetrical about a plane vertically bisecting the length of the straps 100 and 200.

As can be readily visualized based on FIGS. 1-2 and as hereinafter described regarding FIGS. 28-31, if the tourniquet 10 is positioned around a limb of a human body (not shown in FIG. 1), the tightening strap 100, the cinch strap 200, the first D-ring 300, and the buckle 800, of the tourniquet 10 would form a tourniquet loop 52. The tourniquet 10 would be positioned along the length of the limb, as hereinafter described and illustrated. The general location of the twisting assembly 600 in the tourniquet loop 52 of the tourniquet 10 will be arbitrarily referred to as the "top" or "upper" portion of the tourniquet 10, although in use it would not necessarily be positioned in an upper side relative to a limb. In the embodiment shown in FIGS. 1-2, the tourniquet 10 is not symmetrical about a plane along or parallel to an axis of loop 52 shown in FIG. 2 that would be formed when the tourniquet is positioned around a limb, as hereinafter described and illustrated in FIGS. 28-31. As can be understood, while the tourniquet 10 can be used with the twisting assembly 600 positioned in any convenient position around a limb, it will often be more convenient to position the twisting assembly 600 to be operated from above relative to the limb of a patient laying face up in a supine position and so that the twisting assembly 600 is preferably not positioned awkwardly and less comfortably underneath the limb when the patient is laying in a supine (face up) position.

Continuing to refer to FIGS. 1-2, the cinch strap 200 is operatively arranged to allow for cinching of the cinch strap 200, and, thereby, the tourniquet loop 52 around a limb, as hereinafter described and illustrated in FIGS. 28-31. As illustrated in FIGS. 1-2, a first end 201 of the cinch strap 200 is connected to a one-way strap adjuster of the male part 850 of the buckle 800, a middle portion 203 of the cinch strap 200 is threaded through the D-ring 300 and back through the one-way strap adjuster of the male part 850, where the one-way strap adjuster 860 is illustrated in more detail in FIGS. 24-25. Accordingly, the cinch strap 200 is operatively arranged to form a cinch loop 54.

As will hereinafter be described in detail, the tourniquet loop 52 of the tourniquet 10 is adapted to be buckled around a portion of a limb, such as the thigh of a leg as shown in FIGS. 28-31, cinched by pulling on the second end 202 of the cinch strap 200, and then the loop 52 is tightened with the twisting assembly 600 for the tightening strap 100. When desired, the buckle 800 can be used to release and open the tourniquet loop 52 of the tourniquet 10, whereby the tourniquet 10 can be removed from around the limb. As can be understood from FIGS. 1-2 and with reference to FIGS. 28-31, the arrangement of the cinch strap 200 is operative to cinch the tourniquet loop 52 formed by the tourniquet 10 around a limb L in a taut position.

As illustrated in FIGS. 1-2, the cinch strap 200 preferably includes a strap keeper 240. A purpose of the strap keeper 240 is to help minimize any possible confusion for the positioning of the tourniquet 10 around a limb L regarding the tourniquet loop 52 and the cinch loop 54, a strap keeper 240 can be used to hold the cinch loop 54 relatively closed, whereby the forming of the tourniquet loop 52 is clearer to a person applying the tourniquet 10 to a limb L. The temporary strap keeper 240 can be, for example, a breakable plastic keeper or a breakable elastic band or could simply slide along the strap as the cinch strap 200 is being cinched, wherein the temporary strap keeper 240 can be easily broken free from the cinch strap 200 during the intended use of applying the tourniquet 10 to a limb L as illustrated in FIGS. 28-31.

FIG. 3 is an exploded right side view diagram of the general arrangement of parts in the tourniquet 10 illustrated in FIGS. 1 and 2 (but not to the scale of FIGS. 1 and 2), except in a linear position and wherein the holding strap 700 is in an open, unfolded position (as will hereinafter be described in detail).

The tightening strap 100 can have any suitable length, width, and thickness for use in the tourniquet 10. In the illustrated embodiment shown in FIGS. 1-3, the tightening strap 100 has a length of about 16 inches (about 41 cm) and a width of about 1.5 inches (about 3.8 cm). The tightening strap 100 is relatively thin. In the illustrated embodiment, the thickness of the tightening strap 100 is about $1/18^{th}$ inch (about 0.3 cm). The tightening strap 100 can be formed of any suitable structural material having sufficient flexibility and strength for its use in the tourniquet 10. Preferably, the tightening strap 100 is substantially non-elastic such that stretching under tension is relatively minor. In an embodiment, the tightening strap 100 is formed of a woven webbing material. The material can be a material of suitable tensile strength and other desirable characteristics for use in a tourniquet. An example of a suitable material for the tightening strap 100 is a webbing material of woven nylon.

The cinch strap 200 can have any suitable length, width, and thickness for use in the tourniquet 10. In the illustrated embodiment shown in FIGS. 1-3 (not to scale in FIG. 3), the cinch strap 200 has a length of about 50 inches (about 127 cm) (including portions doubled over onto itself and a width of about 1.5 inches (about 3.8 cm). The cinch strap 200 is relatively thin. In the illustrated embodiment, the thickness of the cinch strap 200 is about $1/18^{th}$ inch (about 0.3 cm). The cinch strap 200 can be formed of any suitable structural material having sufficient flexibility and strength for its use in the tourniquet 10. In an embodiment, the cinch strap 200 is formed of a woven webbing material. The material can be a material of suitable tensile strength and other desirable characteristics for use in a tourniquet. An example of a suitable material for the cinch strap 200 is a webbing material of woven nylon.

As illustrated in FIGS. 1-3, the D-ring 300 is attached to the second end 102 of the tightening strap 100. In the illustrated embodiment, the D-ring 300 can be attached to the tightening strap 100 by a loop 120 formed on the second end of the tightening strap 100. The loop 120 can be formed, for example, by sewing the second end 102 of the tightening strap 100 back onto itself, as shown. The D-ring 300 has a generally "D" shaped configuration, wherein the loop 120 of the tightening strap 100 is around the leg of the "D" shape. The size of the D-ring 300 is based on the width of tightening strap 100. For example, for a tightening strap 100 having a width of about 1.5 inches (about 3.8 cm), the D-ring 300 is about 1.5 inches (about 3.8 cm). The D-ring 300 can be formed of any suitable structural material having sufficient strength for its use in the tourniquet 10, such as a plastic or metal.

As can be appreciated by a person of skill in the art upon review of this disclosure, in various embodiments, it should be understood that the tightening strap 100 and the cinch strap 200 can be integrally formed as a single strap, such that a D-ring 300 or other suitable connector is not needed between the tightening strap 100 and the cinch strap 200. In such an embodiment, a purpose or function of the tightening strap 100 and the cinch strap 200 would be performed by a tightening strap portion and a cinch strap portion of a single strap. It should also be understood that in various embodiments, more than two straps can be connected together for the purpose or function of the tightening strap 100 and the cinch strap 200.

As illustrated in FIGS. 1-3, the D-ring 400 is attached to the second end 202 of the cinch strap 200. The D-ring 400 can be the same or different from the D-ring 300, but in the illustrated embodiment of the tourniquet 10, the D-ring 400 is the same as D-ring 300, which are both of typical plastic material and shape. In the illustrated embodiment, the D-ring 400 can be attached to the cinch strap 200 by a loop 220 formed at the second end 202 of the cinch strap 200. The loop 220 can be formed, for example, by sewing the second end 202 of the cinch strap 200 back onto itself, as shown. The D-ring 400 has a generally "D" shaped configuration (as in the letter "D"), wherein the loop 220 of the cinch strap 200 is around the leg of the "D" shape. The size of the D-ring 400 is based on the width of cinch strap 200. For example, for a cinch strap 200 having a width of about 1.5 inches (3.8 cm), the D-ring 400 is about 1.5 inches (about 3.8 cm). The D-ring 400 can be formed of any suitable structural material having sufficient strength for its use in the tourniquet 10, such as a plastic or metal.

As illustrated in FIG. 3, the pad assembly 500 has a lower pad 510 and an upper cover 520.

The pad 510 is adapted to be positioned under a portion of the tightening strap 100 and at least partially under the twisting assembly 600. The pad 510 can help cushion the contact of the hard material of the twisting assembly 600 when the tourniquet 10 is applied against the skin of a limb (as illustrated in FIGS. 28-31). In addition, the pad 510 can help prevent pinching of the skin of a limb by the tourniquet 10 when the ends 101 and 102 of the tightening strap 100 are drawn together during the cinching of the cinch strap 200. In addition, the pad 510 can help prevent pinching by the skin by the tightening strap 100 during tightening of the tightening strap 100 with the twisting assembly 600.

The pad 510 has a first end 511, a second end 512, and a middle portion 513 (lengthwise). In the illustrated embodiment, the pad 510 has a length of about 4 inches (about 10 cm) and a width of about 2 inches (about 5 cm) and is relatively thin. The pad 510 is formed of a flexible, relatively soft material compared to a hard plastic of the base part 610 of the twisting assembly 600. In an embodiment, the pad 510 can be formed, for example, of a flexible fabric material and can optionally be formed of a padding material or include separate padding material (not included in the tourniquet embodiment 10 of FIGS. 1-3). An example of a suitable material for the pad 510 is a webbing material of woven nylon.

Preferably, as indicated in the diagram of FIG. 3, thread stitching or other fastening 515 can be used to securely connect the first end 101 of the tightening strap 100 to the first end 511 of the pad 510. The stitching 515 can help hold a middle portion 513 of the pad 510 from slipping along the twisting strap 100 toward the end 102 of the twisting strap 100 and away from being positioned under the twisting assembly 600.

The cover 520 is adapted to be positioned above the pad 510. The cover 520 has a first end 521 and a second end 522. The lengthwise edges (not shown in FIG. 3) of each side of the pad 510 and of the cover 520 can be sewn or otherwise attached together to form a sleeve 525 longitudinally between the pad 510 and the cover 520. The tightening strap 100 can be positioned through the sleeve 525 and can slide through the sleeve 525. The sleeve 525 helps guide the tightening strap 100 to the twisting assembly 600 when the twisting assembly is used to tighten the tightening strap 100 of the tourniquet 10. In the illustrated embodiment, the cover 520 has a length of about 2 inches (about 5 cm) and a width of about 2 inches (about 5 cm) and is relatively thin. In an embodiment, the cover 520 is formed of a flexible material, such as of fabric or nylon. The material of the cover 520 is not required to be for use as a padding. In the embodiment of tourniquet 10, the length between the first end 521 of the cover 520 and the buckle 800 is at least sufficient to accommodate the size of the twisting assembly 600.

As will be appreciated by a person of skill in the art, in various other embodiments, not illustrated in the drawing, the function of guiding or channeling the tightening strap 100 into a twisting assembly 600 can be other structures, either as part of a pad assembly or as part of a twisting assembly or as a separable part.

The twisting assembly 600 (the parts of which are shown separated in the exploded view of FIG. 3) is hereinafter discussed and shown in detail in FIGS. 4-13. The threading of the twisting strap 100 through the twisting assembly is hereinafter discussed and show in in detail in FIGS. 14-16.

Continuing to refer to the embodiment of the tourniquet 10 illustrated in FIG. 3, a holding strap 700 can be used to hold or attach the twisting assembly 600 to the pad 510, as will hereinafter be described and shown in more detail regarding FIGS. 17-21. The holding strap 700 has a length that is about three times the width of the pad 510 and a width of about 2 inches (about 5 cm) in the plane of the diagram of FIG. 3, whereby the length of the holding strap 700 can be folded twice about the width of the lower pad 510 of the pad assembly 500 to hold the twisting assembly 600 with the pad 510. In this embodiment, the width of the holding strap 700 (as illustrated in FIG. 3) is selected to accommodate the twisting assembly 600. In the illustrated embodiment, the thickness of the holding strap 700 is about ⅛ (about 0.3 cm) to about ¼ inch (about 0.6 cm). As will hereinafter be described in detail regarding FIGS. 17-21, in the embodiment of the tourniquet 10, the holding strap 700 includes a hook-and-loop fastening system, such as a VELCRO brand strap with a multitude of such small hook-and-loop fasteners, where the hooks 710 are attached on one surface of the strap and loops 720 are attached on the opposite surface. It should be understood, of course, that other additional or alternative means of holding or attaching the twisting assembly 600 to the pad 510 can be used. In various embodiments, an adhesive can be used instead of a hook-and-loop fastener system.

Turning now FIGS. 4-13, the twisting assembly 600 is described in detail. The twisting assembly 600 includes a base part 610 and a twisting part 650.

FIG. 4 is an oblique upper side perspective view of the twisting assembly 600, showing a base part 610 and a twisting part 650.

FIG. 5 is an oblique under side perspective view of the twisting assembly 600, showing the base part 610 and the twisting part 650.

FIG. 6 is an exploded end elevation view of the twisting assembly 600, showing the base part 610 and the twisting part 650.

FIG. 7 is an exploded side elevation view of the twisting assembly 600, showing the base part 610 and the twisting part 650.

FIG. 8 is a bottom plan view of the twisting assembly 600, showing the base part 610 and the twisting part 650.

FIG. 9 is a top plan view of the twisting assembly 600, showing the base part 610 and the twisting part 650.

FIG. 10 is a bottom plan view of the twisting part 650.

FIG. 11 is an oblique under side perspective view of the twisting part 650.

FIG. 12 is an oblique upper side perspective view of the base part 610.

FIG. 13 is an oblique under side perspective view of the twisting assembly 600, illustrating the base part 610 and the twisting part 650 in a fully engaged condition.

Referring to FIGS. 4-9 and 12-13, the base part 610 includes a lower saddle portion 620, an upper socket portion 630, and a plurality of lower teeth 640 at a lower end of the socket portion 630 adjacent the lower saddle portion 620.

The saddle portion 620 of the base part 610 has a generally horizontal bottom wall 622 with an opening 623. In this embodiment of the base part 610, the bottom wall 622 is substantially square having an overall length and width of about 1.5 inches (about 3.8 cm). A right side wall 624 and left side wall 625 are each downwardly extending from the bottom wall 622. The right side wall 624 and left side wall 625 are of a relatively short height adapted to provide for the horizontal slots 626 and 627. In the illustrated embodiment, the right side wall 624 and left side wall 625 each have a height of about 0.4 inch (about 1 cm).

A right side elongated horizontal slot 626 is formed in the right side wall 624 and a left side elongated horizontal slot 627 is formed in left side wall 625. The width and the height of the horizontal slots 626 and 627 are adapted to accommodate passing of the width and thickness of the holding strap 700 (not shown in FIGS. 4-13) through the slots, as will hereinafter be described in detail. As will additionally be hereinafter described in detail, the saddle portion 620 is adapted to straddle portions of the tightening strap 100 and to straddle a portion of the pad 510 (not shown in FIGS. 4-13). When the base part 610 is strapped with the holding strap 700 to the pad 510, the base part 610 is held substantially together with the pad 510 and held relative to the orientation of the pad 510, whereby the base part 610 is substantially held against twisting relative to the pad 510.

An upper socket portion 630 (female) has a cylindrical wall 632 defining an inner cylindrical surface 634 and defining an interior cylindrical opening 636 through the upper socket portion 630. In the illustrated embodiment, the socket portion 630 is integrally formed with the lower saddle portion 620 of the base part 610. The height of the socket portion 630 is about 1 inch (2.5 cm).

At a lower portion of the cylindrical wall 632 of the socket portion 630 adjacent the bottom wall 622 of the saddle portion 620 are a plurality of circumferentially disposed, upwardly facing teeth 640. As illustrated, for example in FIG. 12, each tooth 642 of the plurality of lower teeth 640 has a leading, upwardly sloped surface 644 (clockwise looking downward toward the saddle portion), a peak 646, and a trailing vertical surface 648. The operation of the plurality of lower teeth 640 will hereinafter be described in detail.

Referring to FIGS. 4-11 and 13, the twisting part 650 includes a lower hub portion 660, a plurality of upper teeth 670 at the lower end of the hub portion 660, and a windlass portion 680 at an upper end of the hub portion 660. It should be understood that if suitable to be grasped by hand to provide sufficient leverage, the body structure of the hub portion 660 can function as a windlass portion of a twisting assembly.

The hub portion 660 (male) has a cylindrical wall 662 defining an outer cylindrical surface 664 and defining a cylindrical opening 665 through the hub portion 660. In this embodiment, the height of the hub portion 660 is about 1 inch (2.5 cm).

At a lower portion of the cylindrical wall 662 of the hub portion 660 are a plurality of circumferentially disposed, downwardly facing teeth 670. In the illustrated embodiment, the upper teeth 670 are integrally formed at the lower portion of the cylindrical wall 662. As illustrated, for example in FIG. 5, each tooth 672 of the plurality of teeth 670 has a leading, downwardly sloped surface 674 (counter-clockwise looking upward toward the saddle portion), a peak 676, and a trailing vertical surface 678. The operation of the plurality of upper teeth 670 will hereinafter be described in detail.

At an upper portion of the hub portion 660 is a windlass portion 680, which can function as a windlass for the tightening strap 100 (not shown in FIGS. 4-13) as hereinafter described in detail. In the illustrated embodiment, the windlass portion 680 is integrally formed with the hub portion 660.

The windlass portion 680 includes an elongated horizontal bar portion 682 between the slots 692 and 694 in the upper wall portion 690.

In the illustrated embodiment, the windlass portion 680 additionally includes first and second vertically (for example, downwardly) extending portions 684 and 685 at the ends of the elongated bar portion 682. The vertically extending portion 684 has opposite facing surfaces 684A and 684B, where each of the surfaces 684A and 684B is in a plane adjacent to and substantially parallel to a central axis of the hub portion 660. Similarly, the vertically extending portion 685 has opposite facing surfaces 685A and 685B, where each of the surfaces 685A and 685B is in a plane adjacent to and substantially parallel to a central axis of the hub portion 660. As can be appreciated, the diagonally opposed surfaces 684A and 685B or diagonally opposed surfaces 684b and 685a are conveniently positioned and shaped for engagement with the thumb and fingers of a person's hand (not shown in the figures) to turn the twisting part 650 about the hub portion 660 when the hub portion 660 of the twisting part 650 is positioned into the socket portion 630 of the base part 610. It should be understood that if suitable to be grasped by hand to provide sufficient leverage, the body structure of the hub portion 660 can function as a windlass portion of a twisting assembly without need for extending portions 684 and 685.

In the illustrated embodiment of the twisting assembly 600, as visible in the views of FIGS. 4 and 7-11, the twisting part 650 includes a top wall 690. In addition, the upper portion of the hub portion 660 includes twisting strap slots 692 and 694, where the twisting strap slots are through the top wall 690 adjacent to and on either side of the central horizontal bar portion 682 of the windlass portion 680.

As shown in FIGS. 6-9, the hub portion 660 of the twisting part 650 has an exterior cylindrical wall surface 664 having a smaller outer diameter than the inner diameter of the interior cylindrical wall surface 634 of the socket portion 630 of the base part 610. When the hub portion 660 of the twisting part 650 is positioned in the socket portion 630 of the base part 610, a clearance 699 is provided between the exterior cylindrical wall surface 664 of the hub portion 660 and the inner cylindrical wall surface 634 of the socket portion 630, whereby the twisting part 650 can rotate freely with the hub portion 660 of the twisting part 650 in the socket portion 630 of the base part 610. In addition, the hub portion 660 of the twisting part 650 can move freely vertically into or out of the socket portion 630 of the base part 610.

As can be appreciated, the hub portion 660 and the socket portion 630 cooperate as an alignment system to help axially align the plurality of teeth 670 of the twisting part 650 with the plurality of teeth 640 of the base part 610.

In addition, as can be appreciated from FIGS. 4-14 regarding the details of the twisting assembly 600, the plurality of teeth 670 of the twisting part 650 are adapted to correspond and engage with the plurality of teeth 640 of the base part 610. The plurality of teeth 670 of the twisting part 650 can be fully engaged with the plurality of teeth 640 of the base part 610. The plurality of teeth 670 and the plurality of teeth 640 can cooperate as a ratcheting system. The engagement of the plurality of teeth 640 of the base part and the plurality of teeth 670 of the twisting part can be likened to the meshing engagement of gear teeth of a gear mechanism, although the base part 610 and the twisting part 650 do not necessarily function as a gear mechanism.

With the respective pluralities of teeth 640 and 670 of the ratcheting system in a fully engaged position, when the twisting part 650 is attempted to be turned by hand using the windlass portion 680 in a clockwise direction (looking downward as in the view of FIGS. 4 and 6-7), the leading sloped surfaces 674 of the upper teeth 670 engaging with the corresponding leading sloped surfaces 644 of the lower teeth 640 tend to cooperate to redirect some of the rotational force upward with the clockwise rotational movement to separate the system of teeth and allow the twisting part 650 to turn about the hub portion 660 in the socket portion 630 of the base part 610. In this manner, the upper teeth 670 can be rotated to slide relatively easily clockwise over the lower teeth 640, allowing the twisting part 650 to be turned about the hub portion 660 positioned in the socket portion 630 of the base part 610 relatively easily relative to the base part 610.

However, with the respective pluralities of teeth 640 and 670 of the ratcheting system in a fully engaged position, when the twisting part 650 is attempted to be turned by hand using the windlass portion 680 in a counter-clockwise direction (looking downward as in the view of FIGS. 4 and 6-7), the trailing vertical surfaces 678 of the upper teeth 670 engaging with the corresponding trailing vertical surfaces 648 of the lower teeth tend to block turning of the twisting part without redirecting any of the turning force upward and without tending to separate the ratcheting system of teeth. In this manner, the twisting part 650 cannot be turned counter-clockwise relative to the base part 610.

It can be understood, of course, that the allowing of a clockwise direction of rotation relatively easily and counter-clockwise direction of blocking rotation by the teeth of the ratcheting system is a matter of design preference. As can be appreciated, the twisting assembly 600 could be designed and made function clockwise or counter-clockwise, as desired.

Turning now to FIGS. 14-15, the threading of the twisting strap 100 through the twisting assembly 600 is illustrated in detail.

FIG. 14 is an exploded left side perspective view showing the threading of a portion of the tightening strap 100 through the base part 610 and the twisting part 650 of the twisting assembly 600, wherein the base part 610 is shown attached to the pad 510 with the holding strap 700 for holding the base part 610 of the twisting assembly 600 onto the pad 510 and preventing the base part 610 from twisting relative to the pad 510.

FIG. 15 is a left side perspective view similar to FIG. 14, but not exploded.

As illustrated in FIG. 14, a portion of the twisting strap 100 is shown threaded in (from the right, but would be to from the left if viewed from the "right" side perspective of FIGS. 1-3) between the downwardly extending right and left side walls 624 and 625 of the saddle portion 620, up through the interior cylindrical opening 636 of the socket portion 630, continuing up through the interior opening 665 (not visible in FIG. 14) of the hub portion 650, up and out through the slot 694 adjacent the elongated bar portion 682 of the windlass portion 680, over and around the elongated bar portion 682 of the windlass portion 680, down through the slot 692 (not visible in FIG. 14) of the hub portion 650, back down through the interior opening 665 (not visible in FIG. 14) of the hub portion 650, continuing back down through the interior cylindrical opening 636 of the socket portion 630, and then out again between the downwardly extending right and left side walls 624 and 625 of the saddle portion 620 (to the left, but would be to the right if viewed from the right side perspective of FIGS. 1-3). Thus, a portion of the twisting strap 100 can be threaded through the twisting assembly 600.

As illustrated in FIG. 15, when the twisting strap 100 is pulled taut to shorten the portion of the twisting strap 100 positioned through the twisting assembly 600, the twisting part 650 of the twisting assembly is pulled downward into the base part 610. In addition, as can be appreciated, when the twisting part 650 is turned, the twisting strap 100 will be twisted together within the twisting assembly 600, pulling the twisting strap 100 from either side into the twisting assembly 600, whereby the effective length of the twisting strap 100 outside of the twisting assembly 600 is shortened. This action of twisting of the twisting strap 100 by turning the twisting part 650 of the twisting assembly 600 can be used to effectively shorten and, thereby, to tighten the twisting strap 100 of the tourniquet loop 52 (not shown in FIGS. 14-15) as is hereinafter described in detail regarding FIGS. 28-31.

As can be understood from the description of the structure and operation of the twisting assembly regarding FIGS. 4-14, when the twisting strap 100 is relatively taut as illustrated in FIG. 15, the twisting part 650 is pulled by the twisting strap 100 into the base part 610, such that the plurality of teeth 670 of the twisting part 650 are engaged with the plurality of teeth 640 of the base part 610. Accordingly, the windlass portion 680 of the twisting part 650 can be used to relatively easily turn the twisting part 650 in a clockwise direction in the socket portion 630 of the base part 610, which will further continue to twist the twisting strap 100 in the twisting assembly and tighten the tourniquet loop 52 (not shown in FIG. 15). As the twisting strap 100 continues to be twisted in the twisting assembly 600, the twisting strap 100 will tend to pull the twisting part 650 tighter and tighter into engagement with the base part 610. As the tourniquet loop 52 is tightened, the twisted portion of the twisting strap 100 in the twisting assembly 600 will have a tendency to untwist. However, the engaged teeth of the ratcheting system will block the untwisting of the twisting strap 100 in the twisting assembly 600, which will prevent the loosening of the tourniquet loop 52. This can be helpful in case a hand slips during turning of the windlass part 680 of the twisting assembly, keeping the tourniquet in place and so that further tightening can be continued if needed without having had any appreciable loosening of the already tightened position of the tourniquet.

Turning now to FIGS. 16-17, the threading of the holding strap 700 through the base part 610 of the twisting assembly 600 is illustrated in more detail.

FIG. 16 is an exploded left side perspective view similar to FIG. 15 showing the threading of the tightening strap 100 through the base part 610 and the twisting part 650 of the twisting assembly 600, but without the holding strap 700 to better view the left side holding strap slot 627 in the saddle portion 620 of the base part 610.

FIG. 17 is an exploded right-end perspective view similar to FIG. 16 illustrating the holding strap 700 threaded through the slots 626 and 627 (not visible in this figure) of the right side and left side walls 624 and 625 of the saddle portion 620 of the base part 610 of the twisting assembly 600.

Turning now to FIGS. 18-21, the folding of the holding strap 700 around the pad 510 for securing the base part 610 (not shown in FIGS. 18-21) to the pad 510 is illustrated in more detail. The holding strap 700 has a first end 701, a second end 702, and a middle portion 703. In the illustrated embodiment, the holding strap 700 additionally has a hook-and-loop fastening system such as VELCRO brand. The hooks 710 of the hook-and-loop fastening system are on one surface of the holding strap 700 and the loops of the hook-and-loop fastening system are on the other surface of the holding strap 700.

FIG. 18 is an under side perspective view illustrating the holding strap 700 over the pad assembly 500, wherein a first end 701 and a second end 702 of the holding strap 700 are shown in an open, unfolded position, and wherein a middle portion 703 of the holding strap is underneath the pad 510, as in a step in attaching the holding strap 700 to the pad 510.

FIG. 19 is an under side perspective view illustrating the holding strap 700 over the pad assembly 500, similar to FIG. 18 but wherein the first end 701 of the holding strap 700 is shown in a closed, folded portion around a portion of the pad assembly 500 and wherein the second end 702 of the holding strap 700 is shown in an open, unfolded position, as in a further step in attaching the holding strap 700 to the pad 510.

FIG. 20 is an under side perspective view illustrating the holding strap 700 over the pad assembly 500, similar to FIGS. 18 and 19 but wherein the first end 701 of the holding strap 700 is shown in a folded portion around a portion of the pad assembly 500 and wherein the second end 702 of the holding strap 700 is shown in a closed, folded position, as in a further step in attaching the holding strap 700 to the pad 510.

FIG. 21 is a under end perspective view illustrating the holding strap 700 (with hook-and-loop fastener, for example, VELCRO brand) and with both the first end 701 and the second end 702 shown folded under the pad 510, in a position similar to that of FIG. 20.

In various embodiments, an adhesive can be used instead hook-and-loop fasteners.

Turning now to FIGS. 22-25, an example of a suitable clasp for use in the tourniquet 10, that is, the buckle 800, is illustrated in more detail. The buckle 800 is an assembly that includes a female part 810 and a male part 850. As further described, the buckle 800 includes a one-way strap adjuster 860.

FIGS. 22-23 show the attachment of the first end 101 of the twisting strap 100 to the female part 810 in more detail.

FIG. 22 is a right side elevation view of the female part 810 (of buckle 800 not shown as a whole in this figure) attached to the first end 101 of tightening strap 100.

FIG. 23 is a top plan view of the female part 810 (of buckle 800 not shown as a whole in this figure) attached to the first end 101 of tightening strap 100.

As illustrated in FIGS. 22-23, the female part 810 includes a body 820 forming a socket, wherein the body 820 includes a top wall 822, a bottom wall 824, a right side wall 826, and a left side wall 827. A right side opening 828 is formed in the right side wall 826 and a left side opening 829 is formed in the left side wall 827.

A square ring portion 830 is integrally formed with the body 820 of the female part 810. The first end 101 of the tightening strap 100 can be attached to the square ring portion 830, for example by a loop 110 formed and sewn in the first end 101 of the tightening strap 100. The loop 110 can be formed, for example, by sewing the first end 101 of the tightening strap 100 back onto itself, as shown. As described herein regarding FIGS. 1 and 3, the first end 101 of the tightening strap 100 can be sewn or attached to the first end 511 of the pad 510.

FIGS. 24-25 show the detail of the male part 850 and the attachments of the cinch strap 200 to the one-way strap adjuster 860.

FIG. 24 is a under right side perspective view of the male part 850 (of buckle 800 not shown as a whole in this figure). In the illustrated embodiment of the male part 850, the one-way strap adjuster 860 is integrally formed with the male part 850.

FIG. 25 is a bottom perspective view of the male part 850 (of buckle 800 not shown as a whole in this figure) attached to a first end 201 of the cinch strap 200.

As illustrated in FIGS. 24-25, the male part 850 includes a center guide 852, a structural bar 853, a right side arm 854 and a left side arm 855. As understood in the technology related to such buckles, the right side arm 854 has a right side engaging lip 856 for engaging a corresponding structure on the female part 810 (not shown), and the left side arm 855 has a left side engaging lip 857 for engaging a corresponding structure on the female part 810 (not shown). In addition, the right side arm 854 has a right side finger surface 858 and the left side arm 855 has a left side finger surface 859. The right and left side finger surfaces 858 and 859 can be squeezed together by the thumb and index finger of a hand to release the male part 850 of the buckle 800 from the female part 810 of the buckle 800. The right side arm 854 and the left side arm 855 are formed of an appropriately resilient plastic such that the arms 854 and 855 can be pushed inward toward the central guide 852 or squeezed from the sides to temporarily deflect the arms 854 and 855 inward toward the central guide 852 of the male part 850. As understood in the technology related to such buckles, the deflection of the arms 854 and 855 can be used to selectively engage the engaging lips 856 and 857 with the female part 810 or to selectively disengage the engaging lips 856 and 857 from the female part 810 (not shown).

Continuing to refer to FIGS. 24-25, the one-way strap adjuster 860 includes a right side wall 861A and a left side wall 861B. A locking bar 862 is supported between right side wall 861A and the left side wall 861B and between the structural bar 853 and a rear bar 863. The space between the structural bar 853 and the locking bar 862 defines a slot opening 864. The space between the locking bar 862 and the rear bar 863 defines a slot opening 866. As understood in the technology of buckles, the locking bar 862 has an edge adapted for frictionally engaging the webbing material of a strap such as of the cinch strap 200. The edge (not shown in detail) can optionally or preferably have etched, notched, or small teeth for assisting in the frictional or gripping engagement with the webbing material of the cinch strap 200. The edge of the locking bar is oriented to allow the cinch strap to be freely pulled in one direction through the slot opening 866, but the edge of the locking bar 862 is oriented to engage the webbing material and frictionally grip or bite into the webbing material to prevent movement in the opposite direction through the slot opening 866.

As illustrated in FIGS. 24-25, the first end 201 of the cinch strap 200 is shown attached with the loop 210 to the strap attachment ring 840 of the male part 850 of buckle 800. The strap attachment ring 840 defines a slot opening 866 formed by the right side wall 861A and a left side wall 861B, the locking bar 862 and the rear bar 863. The loop 210 can be formed, for example, by sewing the first end 201 of the cinch strap 200 back onto itself, as shown.

The second end 202 of the cinch strap 200 threaded through the one-way strap adjuster 860 such that a middle portion 203 of the cinch strap 200 is through the strap adjuster 860, as shown. The strap adjuster 860 has an edge of a locking bar 862 for frictionally engaging the first end 201 of the cinch strap 200 when the cinch strap 200 and the one-way strap adjuster are cooperatively positioned relative to each other such that edge 862 of the strap adjuster 860 frictionally engages the webbing material of the cinch strap 200. Preferably, the edge 862 is notched or etched to increase the frictional engagement with the webbing material of the cinch strap 200.

Additional details of such buckle devices are known in the field of buckle technology and design, for example, the following U.S. patents which are incorporated by reference in their entirety: U.S. Pat. No. 5,546,642 issued Aug. 20, 1996 having for named inventor Joseph Anscher, entitled "Side-release buckle fastener"; U.S. Pat. No. 5,222,279 issued Jun. 29, 1993 having for named inventors Francis G. Frano and Steven C. Keller, entitled "Buckle having increased holding power when under load"; and U.S. Pat. No. 4,831,694 issued May 23, 1989, having for named inventor Alan Kong, entitled "Buckle having external finger grip."

An example of a structure of a suitable strap adjuster, which can be integrally formed with a clasping device such as in buckle 800, is commercially available from Strapworks in Eugene, Oregon. An example of a structure of a suitable side release one-way adjust buckle, also known as a "single adjust side release buckle," is commercially available from Strapworks in Eugene, Oregon. Similarly, an example of a suitable buckle product is a MOJAVE brand plastic side release buckle, single adjust.

Embodiment of a Tourniquet Having a Buckle Without a One-Way Strap Adjuster

FIG. 26 is a under right side perspective view of a male part 851 (of a buckle 800 not shown as a whole in this figure). In the illustrated embodiment of the male part 851 illustrated in FIG. 26, the male part 851 is similar to the male part 850 illustrated in FIGS. 24-24, except the one-way strap adjuster 860 is not included.

FIG. 27 is a bottom perspective view of the male part 851 (of buckle 800 not shown as a whole in this figure) attached to a first end 201 of the cinch strap 200.

As illustrated in FIGS. 26-27, the male part 851 includes a center guide 852, a structural bar 853, a right side arm 854 and a left side arm 855. As understood in the technology related to such buckles, the right side arm 854 has a right side engaging lip 856 for engaging a corresponding structure on the female part 810 (not shown), and the left side arm 855 has a left side engaging lip 857 for engaging a corresponding structure on the female part 810 (not shown). In addition, the right side arm 854 has a right side finger surface 858 and the left side arm 855 has a left side finger surface 859. The right and left side finger surfaces 858 and 859 can be squeezed together by the thumb and index finger of a hand to release the male part 850 of the buckle 800 from the female part 810 of the buckle 800. The right side arm 854 and the left side arm 855 are formed of an appropriately resilient plastic such that the arms 854 and 855 can be pushed inward toward the central guide 852 or squeezed from the sides to temporarily deflect the arms 854 and 855 inward toward the central guide 852 of the male part 850. As understood in the technology related to such buckles, the deflection of the arms 854 and 855 can be used to selectively engage the engaging lips 856 and 857 with the female part 810 or to selectively disengage the engaging lips 856 and 857 from the female part 810 (not shown).

Continuing to refer to FIGS. 26-27, in this embodiment the male part 851 of the buckle does not includes a one-way strap adjuster.

As illustrated in FIGS. 26-27, the first end 201 of the cinch strap 200 is shown attached with the loop 210 to the strap attachment ring 841 of the male part 851 of a buckle 800. The strap attachment ring 841 defines a slot opening 867 formed by the right side wall 861A and a left side wall 861B, the structural bar 853 and the rear bar 863. The loop 210 can be formed, for example, by sewing the first end 201 of the cinch strap 200 back onto itself, as shown.

In this embodiment, the second end 202 of the cinch strap 200 is threaded through the same attachment ring 841 such that a middle portion 203 of the cinch strap 200 is through the attachment ring 841 of the male part 851 of the buckle, as shown. Even without a locking bar 862 of a strap adjuster, in this embodiment the friction between the webbing portions of the cinch strap 200 can be sufficient for tourniquet applications to maintain the desired tightness around a limb.

Methods of Using a Tourniquet with a Twisting Assembly

Turning now to FIGS. 28-31, an example of the steps of applying and releasing the tourniquet 10 with a limb such as a leg are illustrated.

FIG. 28 is an oblique right side perspective view of the tourniquet 10 in a condition of being positioned and buckled but loose around the thigh of a human leg L. The buckle 800 of the tourniquet 10 is connected by holding or pushing the female part 810 in the direction of arrow A and holding or pushing the male part 850 in the direction of arrow B so that the female part 810 and male part 850 engage together to form a buckled connection with the tourniquet 10 around the limb L.

FIG. 29 is an oblique right side perspective view of the tourniquet 10 in a condition of having been buckled and the second end 202 of the cinch strap 200 being pulled in the direction of arrow C to cinch the tourniquet in a taut condition around the thigh of a human leg L. The direction of pulling arrow C is illustrated as being radially outward from the encircled limb L, however, additional leverage can be obtained by pulling the second end 202 of the cinch strap 200 having the D-ring 400 more or completely tangentially around the limb L in a direction away from the twisting assembly 600 and toward the D-ring 300. As the cinch strap 200 is pulled to make the tourniquet 10 taut around the limb L, friction between the portions of the cinch strap 200 forming the cinch loop 54 (indicated in FIGS. 28 and 30) help keep the tourniquet 10 in a taut condition as illustrated in FIG. 29 so that the tourniquet does not slip loose. In an application such as a tourniquet, the friction of the cinch strap 200 can be sufficient such that a one-way strap adjuster is not needed. The taut condition of tourniquet 10 caused by a cinching with the cinch strap 200 is usually not sufficiently tight, however, to substantially restrict blood flow to the limb L past the position of the tourniquet 10.

FIG. 30 is an oblique right side perspective view of the tourniquet 10 in a condition of being buckled and fully cinched taut around the thigh of a human leg L and further in a process of being tightened by turning of the twisting part 650 of the twisting assembly 600 in the clockwise direction of arrow D. The twisting assembly 600 can be used to tighten the tourniquet 10 until blood flow to the limb L is adequately restricted or stopped.

FIG. 31 is an oblique right side perspective view of the tourniquet 10 in a condition of being unbuckled and released from previously being tightly applied around the thigh of a human leg L. To unbuckle and release the tourniquet 10, the releasing finger surfaces 858 and 859 of the buckle 800 are manually pushed toward each other in the directions of arrow E and arrow F with the thumb and finger of a hand, whereby when the buckle 800 is released, the male part 850 of the buckle 800 is released in the direction of arrow G from the female part 810 of the buckle, thereby releasing the tourniquet 10 from around the limb L.

As can be understood from the description and FIGS. 1-31 of the drawing, the twisting assembly 600 provides a means for controlling the turning of a windlass for tightening of a tourniquet around a limb. As shown in FIG. 30, the windlass portion 680 of the twisting assembly 600 can be turned in one direction of arrow D to twist the tightening strap 100, whereby the tourniquet 10 can be increasingly tightened around a limb L, but as described in detail regarding FIGS. 5-17, the plurality of teeth 670 of the twisting part 650 can engage with the plurality of teeth 640 of the base part 610 to provide a ratchet mechanism against turning in the opposite counter-clockwise direction to the clockwise direction of arrow D shown in FIG. 30, whereby the tourniquet 10 stays in the tightened condition. In addition, if during tightening of the tourniquet 10 with the twisting assembly 600 the hand (not shown) slips during from the twisting part 650 during turning in the direction of arrow D shown in FIG. 30, the upper teeth 640 and lower teeth 670 engage to provide a ratchet mechanism against any substantial loosening of the tourniquet 10. Thus, a twisting assembly such as the twisting assembly 600 provides for incremental tightening of the tourniquet 10. The hand can be repositioned on the twisting part 650 and continue turning the twisting part 650 of the twisting assembly 600, tightening until the tourniquet 10 is sufficiently tight to slow or stop substantial blood flow to the remainder of the limb L extending from the torso of the body (not shown) past the position of the tourniquet 10 on the limb L.

Of course, a tourniquet can be appropriately positioned an any limb for the purpose of occluding blood flow from the torso beyond the position of application of the tourniquet.

The twisting is self-engaging during operation in the sense that the twisting of the twisting strap 100 that is operatively connected to the twisting part 650 of the twisting assembly 600 helps pull the twisting part 650 downward into engagement with the base part 610. As the twisting assembly 600 tightens the twisting strap 100, the tightening of the twisting strap 100, which is threaded into and upward through the interior of the base part 610, up to the twisting part 650, and back downward and out of the interior of the twisting part 650 increasingly pulls the twisting part 650 downward into engagement with base part 610 as the twisting strap 100 is twisted by the turning of the twisting part 650, having an effect of shortening the twisted length of the middle portion 103 of the twisting strap 100 between the twisting part 650 and the base part 610 relative to the untwisted length of the middle portion 103 of the twisting strap 100.

As can be understood, the number of lower and upper teeth 640 and 670 determines the ratcheting radius for the twisting assembly 600. As can be understood, the fewer the number of circumferentially spaced teeth, the larger the ratcheting radius; the greater number of circumferentially spaced teeth, the smaller the ratcheting radius. The ratcheting radius can be less than 180 degrees, preferably less than 120 degrees (which would be for only three teeth), more preferably less than 90 degrees (which would be for only four teeth), more preferably less than 45 degrees (which would be for 8 teeth), and more preferably less than 36 degrees (which would be for 10 teeth), and so on. Preferably, the number of the plurality of lower teeth 640 is about 12-25 and the number of the plurality of the upper teeth 670 is the same for co-operatively engaging the plurality of lower teeth 640.

The plurality of engaging teeth 640 and 670 can provide a distributed load against untwisting of the twisting strap 100. As can be understood, the greater the number of the plurality of teeth 640 and 670 in the twisting assembly 600, the greater the distribution of the load among the teeth.

An advantage of a twisting assembly according to the disclosure, such as the twisting assembly 600, is that the tourniquet with such a twisting assembly can be operated more securely and without problem in case of an accidental slippage of the hand during turning of the windlass. If the hand of a person slips during turning of the twisting part 650 of the twisting assembly, the lower and upper teeth 640 and 670 quickly engage to block untwisting of the tightening strap 100. However, as can be understood from the description in this disclosure, if the teeth 640 and 670 were too many or too small, such teeth might not engage properly to prevent untwisting and undesired loosening of the tourniquet.

The orientations of the several cooperating surfaces on the lower teeth 640 and upper teeth 670 are such that the twisting assembly 600 is operable to twist and tighten the tightening strap 100 when the twisting part 650 is turned in the direction of arrow D as illustrated in FIG. 30. It can be understood, however, that the orientations of the several cooperating surfaces on the lower teeth 640 and upper teeth 670 can be reversed such that the twisting assembly 600 would be operable to twist and tighten the tightening strap 100 if the twisting part 650 were turned in the opposite direction of arrow D. The turning direction of arrow D is believed to be a matter of arbitrary design choice and more likely to be readily understood as the conventional clockwise direction for a tightening or closing, such as of a conventional water tap at a washing sink (not illustrated in the drawing).

If desired to re-position or re-apply the tourniquet 10 for any reason, the tourniquet 10 can be released with the buckle 800 as illustrated in FIG. 31, the twisting strap 100 can be loosened through the twisting assembly 600 by untwisting, and the tourniquet can be staged and re-applied as shown in FIGS. 28-30.

The tourniquet 10 can be made having suitable size modifications to adapt for use on the limb of a child.

A tourniquet, such as tourniquet 10, can be used in veterinary applications, for example, on the upper portion of the hind leg of a dog. This can be useful, for example, in case of a severe injury to a military, paramilitary, police, or search-and-rescue dog, such as a dog trained to detect explosives. The tourniquet 10 can be made having suitable size modifications to adapt for use on a limb of other kinds of animals.

Second Embodiment of a Tourniquet with a Twisting Assembly

Turning now to FIG. 32, a second example embodiment of a tourniquet according to the disclosure is illustrated.

FIG. 32 is an exploded right side view diagram of the general arrangement of parts in a second embodiment of a tourniquet 20 according to the disclosure, similar to the first embodiment illustrated in FIG. 3 with an embodiment of a pad assembly 550 (which is different from the embodiment of the pad assembly 500 in FIGS. 1-25), wherein the tourniquet 20 is shown in a substantially open, unbuckled linear position and wherein the holding strap 700 is in an open, unfolded position.

In this embodiment of the tourniquet 20, the tightening strap 100 additionally includes a stop 130, which helps in the initial positioning of a middle portion 103 of the tightening strap 100 through the twisting assembly 600. The stop 130 can be, for example, sewn as a bump or fold in a middle portion 103 of the tightening strap 100 or can be a separate part, such as a button, sewn or attached to the tightening strap 100. The stop 130 is adapted to be too large to pass through the slot 692 or slot 694 of the twisting part 650 (not shown in detail in this figure), which can be used to prevent too much of the first end 101 of the tightening strap 100 from being positioned on the other side of the twisting part 650. This can be useful during assembly or staging of a tourniquet according to the disclosure, such as the tourniquet 20. As can be understood from the drawing, during twisting of the tightening strap 100 by the twisting assembly 600, the tightening strap does not move lengthwise over the windlass portion 680, but stays in approximately the initial position except for drawing up some of the first end 101 and some of the middle portion 103 of the twisting strap 100 from either side of the twisting assembly 600 toward and into the twisting assembly 600.

The pad assembly 550 of the tourniquet 20 is similar to the pad assembly 550 of the embodiment of tourniquet 30 and will hereinafter be described in detail regarding tourniquet 30.

The operation of the tourniquet 20 is similar to that shown for tourniquet 10 illustrated in FIGS. 28-31.

Third Embodiment of a Tourniquet with a Twisting Assembly

Turning now to FIGS. 33-44, a third example embodiment of a tourniquet according to the disclosure is illustrated.

FIG. 33 is an exploded right side view diagram of the general arrangement of parts in a third embodiment of a tourniquet 30 according to the disclosure, which is generally similar to the second embodiment of the tourniquet 20 illustrated in FIG. 32, wherein the tourniquet 30 is shown in a substantially open, unbuckled linear position and having a square loop 330 instead of a D-ring 300 and having a different embodiment of a twisting assembly 900 instead of twisting assembly 600.

In this embodiment of the tourniquet 30, as illustrated in FIGS. 33,36-40, and 42-43, the tightening strap 100 additionally includes a stop 130, which helps in the initial positioning of a middle portion 103 of the tightening strap 100 through the twisting assembly 900. The stop 130 can be, for example, sewn as a bump or fold in a middle portion 103 of the tightening strap 100 or can be a separate part sewn or attached to the tightening strap 100. The stop 130 is adapted to be too large to pass through the slot 992 or slot 994 of the twisting part 950 as shown in FIG. 35 and FIG. 36, which can be used to prevent too much of the first end 101 of the tightening strap 100 from being positioned on the other side of the twisting part 950. This can be useful during assembly or staging of a tourniquet according to the disclosure, such as the tourniquet 30. As can be understood from the drawing, during twisting of the tightening strap 100 by the twisting assembly 900, the tightening strap 100 does not move lengthwise over the windlass portion 980 of the twisting part 950, but stays in approximately the initial position except for drawing up some of the first end 101 and some of the middle portion 103 of the twisting strap 100 from either side of the twisting assembly 900 toward and into the twisting assembly 900. Although the structure of the twisting assembly 900 is different from the structure of the twisting assembly 600 regarding tourniquet 20, the operation of the stop 130 is similar in the twisting assembly 900.

As mentioned above, tourniquet 30 has a square loop 330 (instead of a D-ring 300 of tourniquets 10 and 20), as illustrated in FIGS. 33, 37, and 44, which allows better sliding connection between the second end 102 of the tightening strap 100 and the first end 201 of the cinch strap 200.

As illustrated in FIG. 33 and FIG. 36, the pad assembly 550 has a lower pad 560. The pad 560 of the pad assembly 550 is adapted to be positioned under a portion of the tightening strap 100 and under a position for the twisting assembly 900. The pad 560 can help cushion the contact of the hard material of the twisting assembly 900 when the tourniquet 30 is applied against the skin of a limb (as illustrated regarding the similar embodiment of tourniquet 10 in FIGS. 28-31). In addition, the pad 560 can help prevent pinching of the skin of a limb by the tourniquet 30 when the ends 101 and 102 of the tightening strap 100 are drawn together during the cinching of cinch strap 200. In addition, the pad 560 can help prevent pinching by the skin by the tightening strap 100 during tightening of the tightening strap 100 with the twisting assembly 900.

The pad 560 is elongated, having a first end 561, a second end 562, and a middle portion 563 (lengthwise). In the illustrated embodiment, the pad 560 has a length of about 6 inches (about 15 cm) and a width of about 2 inches (about 5 cm) and is relatively thin. The pad 560 is formed of a flexible, relatively soft material compared to a hard plastic of the base part 910 of the twisting assembly 900. In an embodiment, the pad 560 can be formed, for example, of a flexible fabric material and can optionally be formed of a padding material or include separate padding material (not included in the tourniquet embodiment 30 of FIGS. 33-44). An example of a suitable material for the pad 560 is a webbing material of woven nylon.

A first cover 580 is adapted to be positioned above first end 561 of the pad 560. The first cover 580 has a first end 581 and a second end 582. The lengthwise edges (not shown in FIG. 33) of each side of the pad 560 and of the first cover 580 can be sewn or otherwise attached together to form a first sleeve 585 longitudinally between the first end 561 of the pad 560 and the first cover 580. The tightening strap 100 can be positioned through the first sleeve 585 and can slide through the first sleeve 585. The sleeve 585 helps guide the tightening strap 100 to the twisting assembly 900 when the twisting assembly is used to tighten the tightening strap 100 of the tourniquet 30. In the illustrated embodiment, the first cover 580 has a length of about 2 inches (about 5 cm) and a width of about 2 inches (about 5 cm) and is relatively thin. In an embodiment, the first cover 580 is formed of a flexible material, such as of fabric or nylon. The material of the first cover 580 is not required to be for use as a padding.

A second cover 570 is adapted to be positioned above second end 562 of the pad 560. The second cover 570 has a first end 571 and a second end 572. The lengthwise edges (not shown in FIG. 33) of each side of the pad 560 and of the second cover 570 can be sewn or otherwise attached together to form a second sleeve 575 longitudinally between the second end 562 of the pad 560 and the second cover 570. The tightening strap 100 can be positioned through the sleeve 575 and can slide through the second sleeve 575. The sleeve 575 helps guide the tightening strap 100 to the twisting assembly 900 when the twisting assembly is used to tighten the tightening strap 100 of the tourniquet 30. In the illustrated embodiment, the second cover 570 has a length of about 2 inches (about 5 cm) and a width of about 2 inches (about 5 cm) and is relatively thin. In an embodiment, the cover 570 is formed of a flexible material, such as of fabric or nylon. The material of the cover 570 is not required to be for use as a padding.

In the embodiment of tourniquet 30, the length between the second end 582 of the first cover 580 and the first end 571 of the second cover 570 is at least sufficient to accommodate the size of the twisting assembly 900.

As will be appreciated by a person of skill in the art, in various other embodiments, not illustrated in the drawing, the function of guiding or channeling the tightening strap 100 into a twisting assembly can be other structures, either as part of a pad assembly or as part of a twisting assembly or as a separable part.

Turning now FIGS. 34-44, the twisting assembly 900 is described in detail. The twisting assembly 900 includes a base part 910 and a twisting part 950.

FIG. 34 is an oblique upper side and end perspective view of the base part 910.

FIG. 35 is a bottom plan view of the twisting part 950.

FIG. 36 is an exploded left side perspective view of a portion of the tourniquet 30 showing an exploded view of the pad assembly 550, an exploded view of the twisting assembly 900 positioned to be attached to the pad 560 of the pad assembly 550, and showing the twisting strap 100 threaded through the sleeves 575 and 585 of the pad assembly 550 and through the twisting assembly 900.

FIG. 37 is a left side perspective view of a portion of the tourniquet 30 showing the pad assembly 550 and twisting assembly 900 operatively connected between the buckle 800 and the square loop 330, wherein the twisting part 950 is separated or pulled away from the base part 910.

FIG. 38 is a left side and obliquely upward perspective view of a detail portion of the twisting assembly 900, wherein the twisting part 950 is separated or pulled away from the base part 910 such that the interior and under side of the twisting part 950 is partially visible.

FIG. 39 is another is a left side and obliquely upward perspective view of a detail portion of the twisting assembly 900, wherein the twisting part 950 is separated or pulled away from the base part 910 such that the interior and under side of the twisting part 950 is partially visible.

FIG. 40 is a left side and downward perspective view of a detail portion of the twisting assembly 900, wherein the twisting part 950 is separated or pulled away from the base part 910 such that the interior and upper side of the base part 910 is partially visible.

FIG. 41 is an downward perspective view of a detail portion of the twisting assembly 900 shown from the end of the square loop 330 (not shown in FIG. 41), wherein the twisting part 950 is separated or pulled away from the base part 910 such that the interior and upper side of the base part 910 is partially visible.

FIG. 42 is an upward oblique perspective view of a detail portion of the twisting part 950, wherein the twisting part 950 is pulled away from the base part 910 (not shown in FIG. 32) to further illustrate the stop 130 of the twisting strap 100.

FIG. 43 is a left side obliquely upward perspective view of a portion of the tourniquet 30, wherein the twisting part 950 is separated or pulled away from the base part 910 and showing the connection of the tightening strap 100 to the buckle 800.

FIG. 44 is a right side perspective view of a portion of the tourniquet 30, wherein the twisting part 950 is separated or pulled away from the base part 910 and showing the attachments of the tightening strap 100 pulled upward to show another view of the attachments to the loop 330 and the buckle 800.

Referring more particularly to FIG. 34 and FIG. 36, the base part 910 includes a lower saddle portion 912, an upward male portion 930, and a plurality of lower teeth 940 at a lower end of the male portion 930 adjacent the saddle portion 912.

The saddle portion 912 of the base part 910 has a generally horizontal bottom wall 914 with an opening 915 through the middle area of the bottom wall 914. In this embodiment of the base part 910, the bottom wall 914 is substantially square having an overall length and width of about 1.5 inches (about 3.8 cm). A right side wall 916 and left side wall 918 are each downwardly extending from the bottom wall 914. The right side wall 916 and left side wall 918 are of a relatively short height adapted to straddle a portion of the tightening strap 100. In the illustrated embodiment, the right side wall 916 and left side wall 618 each have a height of about 0.2 inch (about 0.5 cm).

In this embodiment, the saddle portion 912 includes a first end tab 921 and a second end tab 922. The end tabs 921 and 922 extend substantially horizontally from the ends of the saddle portion 912.

The first end tab 921 is attached at a corner to an end of the right side wall 916 by a right connecting portion 921A and attached at another corner to an end of the left side wall 918 by a left connecting portion 921B. A first end slot 923 is defined between the first end tab 921, the bottom wall 914, and the connecting portions 921A and 921B as shown in FIG. 34 and FIG. 36. The first end slot 923 is adapted to allow the tightening strap 100 to be threaded through the slot 923. In addition, a plurality of first end tab holes 921C are formed in the first end tab 921. As shown in FIG. 36, the first end tab holes 921C can be used to sew a thread 928 between the first end tab 921 and the pad 560, thereby attaching the first end tab 921 of the base part 910 to the pad 560.

Symmetrically, the second end tab 922 is attached at a corner to an end of the right side wall 916 by a connecting portion (not visible in FIG. 34) and attached at another corner to an end of the left side wall 918 by a connecting portion (not visible in FIG. 34). A second end slot 924 as indicated in FIG. 41 is defined between the second end tab 922, the bottom wall 914, and the connecting portions (not visible in the view of FIG. 36). The second end slot 924 is adapted to allow the tightening strap 100 to be threaded through the second end slot 924. In addition, a plurality of second end tab holes 922C are formed in the first end tab 922. As shown in FIG. 36, the second end tab holes 922C can be used to sew a thread 929 between the second end tab 922 and the pad 560, thereby attaching the second end tab 922 of the base part 910 to the pad 560.

Referring particularly to FIG. 34, the base part 910 includes a male portion 930. The male portion 930 has a cylindrical wall 932 defining an exterior cylindrical wall surface 934, defining an interior cylindrical wall surface 936, and an opening 1037 through the male portion 930 including through the opening 915 of the saddle portion 930. In this embodiment, the height of the male portion 930 is about 0.5 inch (1.2 cm).

At a lower portion of the exterior wall surface 934 of the cylindrical wall 932 of the male portion 930 are a plurality of circumferentially disposed, upwardly facing, lower teeth 940. In the illustrated embodiment, the lower teeth 940 are integrally formed at the lower portion of the cylindrical wall 932 and at the bottom wall 914 of the saddle portion 912. As illustrated, for example in FIG. 34 and FIG. 40, each lower tooth 942 of the plurality of lower teeth 940 has a leading, upwardly sloped surface 944 (clockwise looking upward toward the saddle portion), a peak 946, and a trailing vertical surface 948. The operation of the plurality of upwardly facing, lower teeth 940 can be understood from the figures and will hereinafter be described in detail.

Referring particularly to FIG. 35, the twisting part 950 includes a female portion 960, a plurality of upper teeth 970 at the lower end of the female portion 960, and a windlass portion 980 at an upper end of the female portion 960. It should be understood that if suitable to be grasped by hand to provide sufficient leverage, the body structure of the female portion 960 can function as a windlass portion of a twisting assembly.

The female portion 950 has a cylindrical wall 962 defining an interior cylindrical surface 964 and defining an interior opening 965 through the female portion 960 of the twisting assembly 900. In this embodiment, the height of the female portion 960 is about 0.5 inch (1.2 cm).

At a lower portion of the cylindrical wall 962 of the female portion 960 are a plurality of circumferentially disposed, downwardly facing, upper teeth 970. In the illustrated embodiment, the upper teeth 970 are integrally formed at the lower portion of the cylindrical wall 962. As illustrated in FIG. 42, each tooth 972 of the plurality of upper teeth 970 has a leading, downwardly sloped surface 974 (counter-clockwise looking upward), a peak 976, and a trailing vertical surface 978. The operation of the plurality of upper teeth 970 can be understood from the figures and will hereinafter be described in detail.

At an upper portion of the female portion 960 of the twisting part 950 is a windlass portion 980, which can function as a windlass for the tightening strap 100 as hereinafter described in detail. In the illustrated embodiment, the windlass portion 980 is integrally formed with the upper wall portion 990 of the twisting part 950.

The windlass portion 980 includes an elongated horizontal bar portion 982 in the upper wall portion 990 between the slots 992 and 994.

In the illustrated embodiment, the windlass portion 980 additionally includes first and second vertically (for example, downwardly) extending portions 984 and 985 at the ends of the elongated bar portion 982. The vertically extending portion 984 has opposite facing surfaces 984A and 984B, where each of the surfaces 984A and 984B is in a plane adjacent to and substantially parallel to a central axis of the female portion 960. Similarly, the vertically extending portion 985 has opposite facing surfaces 985A and 985B, where each of the surfaces 985A and 985B is in a plane adjacent to and substantially parallel to a central axis of the female portion 960. As can be appreciated, the diagonally opposed surfaces 984A and 985B or diagonally opposed surfaces 984B and 985A are conveniently positioned and shaped for engagement with the thumb and fingers of a person's hand (not shown in the figures) to turn the twisting part 950 about the male portion 930 when the female portion 960 of the twisting part 950 is positioned over and onto the male portion 930 of the base part 910. It should be understood that if suitable to be grasped by hand to provide sufficient leverage, the body structure of the female portion 960 can function as a windlass portion of a twisting assembly without need for extending portions 984 and 985.

In the illustrated embodiment of the twisting assembly 900, as visible in the view of FIG. 35, the twisting part 950 includes a top wall 990. In addition, the upper portion of the female portion 960 includes twisting strap slots 992 and 994, where the twisting strap slots are through the top wall 990 adjacent to and on either side of the central horizontal bar portion 982 of the windlass portion 980.

As shown in FIGS. 35 and 42, the female portion 960 of the twisting part 950 has an interior cylindrical wall surface 964 having a slightly larger diameter than the outer diameter of the cylindrical wall surface 934 of the male portion 930 of the base part 910. When the female portion 960 of the twisting part 950 is positioned over and onto the male portion 930 of the base part 910, a clearance is provided between the interior cylindrical wall surface 964 of the female portion 660 and the exterior cylindrical wall surface 934 of the male portion 930, whereby the twisting part 950 can rotate freely with the female portion 960 of the twisting part 950 around the male portion 930 of the base part 910. In addition, the female portion 960 of the twisting part 950 can move freely or float vertically onto or away from the male portion 930 of the base part 910.

As can be appreciated, the female portion 960 and the male portion 930 cooperate as an alignment system to help axially align the plurality of teeth 970 of the twisting part 950 with the plurality of teeth 940 of the base part 910.

In the embodiment of the twisting assembly 900, as a matter of preferred design choice, the female portion 960 and the male portion 930 have a smaller overall height than the socket portion 630 and hub portion 660 of the twisting assembly 600. Thus, the twisting assembly 900 can be more compact than the twisting assembly 600. In various other contemplated embodiments, a twisting assembly does not necessarily require any alignment system.

In addition, as can be appreciated from FIGS. 34-44 regarding the details of the twisting assembly 900, the plurality of upper teeth 970 of the twisting part 950 are adapted to correspond and engage with the plurality of lower teeth 940 of the base part 910. The plurality of upper teeth 970 of the twisting part 950 can be fully engaged with the plurality of lower teeth 940 of the base part 910. The plurality of teeth 970 and the plurality of teeth 940 can cooperate as a ratcheting system for the twisting of the windlass portion 980.

With the respective pluralities of teeth 940 and 970 of the ratcheting system in a fully engaged position, when the twisting part 950 is attempted to be turned by hand using the legs 984 and 985 associated with the windlass portion 980 in a clockwise direction (looking downward as in the view of FIG. 33), the leading sloped surfaces 974 of the upper teeth 970 engaging with the corresponding leading sloped surfaces 944 of the lower teeth 940 tend to cooperate to redirect some of the rotational force upward with the clockwise rotational movement to separate the ratcheting system of teeth and allow the twisting part 950 to turn about the male portion 930 of the base part 910. In this manner, the upper teeth 970 can be rotated to slide relatively easily clockwise over the lower teeth 940, allowing the twisting part 950 to be turned about the male portion 930 of the base part 910 relatively easily relative to the base part 910.

However, with the respective pluralities of teeth 940 and 970 of the ratcheting system in a fully engaged position, when the twisting part 950 is attempted to be turned by hand using the windlass portion 980 in a counter-clockwise direction (looking downward as in the view of FIG. 33), the trailing vertical surfaces 978 of the upper teeth 970 engaging with the corresponding trailing vertical surfaces 948 of the lower teeth 940 tend to block turning of the twisting part 950 without redirecting any of the turning force upward and without tending to separate the ratcheting system of teeth. In this manner, the twisting part 950 cannot be turned counter-clockwise relative to the base part 910.

It can be understood, of course, that the allowing of a clockwise direction of rotation relatively easily and counter-clockwise direction of blocking rotation by the teeth of the ratcheting system is a matter of design preference. As can be appreciated, the twisting assembly 900 could be designed and made with cooperating teeth that function clockwise or counter-clockwise, as desired.

The threading of the twisting strap 100 through the twisting assembly 900 is similar to that regarding the twisting assembly 600 for the embodiment of tourniquet 10.

The operation of the tourniquet 30 is generally similar to that shown for tourniquet 10 and as illustrated in FIGS. 28-31.

Fourth Embodiment of a Tourniquet with a Twisting Assembly

Turning now to FIGS. 45-48, a fourth example embodiment of a tourniquet according to the disclosure is illustrated.

FIG. 45 is an oblique upper side perspective view of a fourth embodiment of a portion of a tourniquet 40 according to the disclosure, wherein the tourniquet 40 is similar to the tourniquet 30 illustrated in FIGS. 33-44 except wherein the tourniquet 40 has a third embodiment of a twisting assembly 1000 (instead of the second embodiment of a twisting assembly 900), wherein the twisting assembly 1000 includes a base part 1010 attached to the pad assembly 500 and a twisting part 1050 attached to the twisting strap 100.

FIG. 46 is an end view of the twisting assembly 1000 attached to the pad assembly 550.

FIG. 47 is a top plan view of the twisting assembly 1000 attached to the pad assembly 550.

FIG. 48 is an oblique upper side view perspective of the twisting assembly 1000 illustrating how the base part 1010 can be used to lock the twisting part 1050 against untwisting, wherein for clarity of the illustration the twisting strap 100 is not shown.

The tourniquet 40 includes the same basic elements is similar to the tourniquet 30 illustrated in FIGS. 33-44 except wherein the tourniquet 40 has a twisting assembly 1000 instead of the twisting assembly 900 of the tourniquet 30. To illustrate the different twisting assembly 1000, on the portion of the tourniquet 40 having the twisting assembly 1000 is illustrated in detail in FIGS. 45-48. A twisting strap 100 is illustrated in FIGS. 45-47 threaded through the twisting assembly 1000 and the twisting assembly 1000 is shown attached to a pad assembly 550. The twisting strap 100 (not completely shown in FIGS. 45-47) and the pad assembly 550 (not completely shown in FIGS. 45-48) and the other elements of the tourniquet 40 are the same as for the tourniquet 30, the details of which are described in regarding the illustrations of FIGS. 33-44 regarding tourniquet 30.

In addition, the twisting strap 100 preferably has a stop 130 the same as in the tourniquet 30 and having a similar purpose, but a stop 130 is not illustrated in FIGS. 45-48.

As illustrated in FIGS. 45-48, the twisting assembly 1000 of tourniquet 40 is described in detail.

The twisting assembly 1000 includes a base part 1010 and a twisting part 1050.

The base part 1010 includes a lower saddle portion 1012, an upper portion 1030, and a plurality of teeth 1040 on the upper portion 1030.

The saddle portion 1012 of the base part 1010 is generally similar to the saddle portion 912 of the base part 910 of the tourniquet 30. The saddle portion 1012 of the base part 1010 has a generally horizontal bottom wall 1014 with an opening 1015 through the middle area of the bottom wall 1014. In this embodiment of the base part 1010, the bottom wall 1014 is substantially square having an overall length and width of about 1.5 inches (about 3.8 cm). A right side wall 1016 and left side wall 1018 are each downwardly extending from the bottom wall 1014. The right side wall 1016 and left side wall 1018 are of a relatively short height adapted to straddle a portion of the tightening strap 100. In the illustrated embodiment, the right side wall 1016 and left side wall 1018 each have a height of about 0.2 inch (about 0.5 cm).

In this embodiment, the saddle portion 1012 includes a first end tab 1021 and a second end tab 1022. The end tabs 1021 and 1022 extend substantially horizontally from the ends of the saddle portion 1012.

The first end tab 1021 is attached at a corner to an end of the right side wall 1016 by a connecting portion 1021A and attached at another corner to an end of the left side wall 1018 by a connecting portion 1021B. A first end slot 1023 is defined between the first end tab 1021, the bottom wall 1014, and the connecting portions 1021A and 1021B as shown in FIG. 45 and FIG. 47 and FIG. 48. The first end slot 1023 is adapted to allow the tightening strap 100 to be threaded through the slot 1023. In addition, a plurality of first end tab holes 1021C are formed in the first end tab 1021. Similar to as shown in FIG. 36 regarding the base part 900, the first end tab holes 1021C can be used to sew a first thread 1028 between the first end tab 1021 and the pad 560, thereby attaching the first end tab 1021 of the base part 1010 to the pad 560.

Symmetrically, the second end tab 1022 is attached at a corner to an end of the right side wall 1016 by a connecting portion 1022A and attached at another corner to an end of the left side wall 1018 by a connecting portion 1022B. A second end slot 1024 as indicated in Figure (not clearly visible in the figures) is defined between the first end tab 1022, the bottom wall 1014, and the connecting portions (not clearly visible in the figures). The second end slot 1024 is adapted to allow the tightening strap 100 to be threaded through the slot 1024. In addition, a plurality of second end tab holes 1022C are formed in the first end tab 1022. Similar to as shown in FIG. 36 regarding the base part 900, the second end tab holes 1022C can be used to sew a second thread 1029 between the second end tab 1022 and the pad 560, thereby attaching the second end tab 1022 of the base part 1010 to the pad 560.

Continuing to refer to FIGS. 45-48, the base part 1010 includes an upper portion 1030. The upper portion 1030 has a cylindrical wall 1032 defining an exterior cylindrical wall surface 1034, defining an interior cylindrical wall surface 1036, and an opening 1037 through the upper portion 1030 and connecting through to the opening 1015 in the saddle portion 1010. In this embodiment, the height of the upper portion 1030 is about 0.5 inch (1.2 cm) to about 1 inch (2.5 cm)

Formed or positioned on the upper end of the cylindrical wall 1032 of the upper portion 1030 are a plurality of circumferentially disposed, upwardly facing, teeth 1040. In the illustrated embodiment, the teeth 1040 are integrally formed at the upper portion of the cylindrical wall 1032.

As illustrated, for example in FIG. 45 and FIG. 48, each tooth 1042 of the plurality of teeth 1040 has a leading, upwardly sloped surface 1044 (counter-clockwise looking downward toward the saddle portion 1010), a leading vertical surface of the tooth 1045 between the leading sloped surface 1044 of the tooth 1042 to the peak surface 1046 of the tooth 1042, a peak horizontal surface 1046, trailing vertical surface 1047 of the tooth 1042 between the peak surface 1046 of the tooth and the trailing curved surface 1048, and a trailing curved surface 1048. The operation of the plurality of upwardly facing teeth 1040 can be understood from the FIGS. 45-48 and will hereinafter be described in detail.

The twisting part 1050 includes at least a windlass portion 1080. The windlass portion 1080 includes an elongated bar portion 1082 that can be oriented generally horizontally. The windlass portion 1080 has a curved surface 1083 of the elongated central bar portion selected or adapted for interacting and engaging with the teeth 1040 of the base part 1010. The windlass portion 1080 provides a handle for twisting of the twisting part 1050 of the twisting assembly 1000, which can be manually operated by a person's hand.

In addition, the twisting part 1050 includes a tightening strap slot 1092, where the twisting strap slot is through a middle portion of the elongated bar portion 1082 of the windlass portion 1080. The threading of the twisting strap 100 through the twisting assembly 1000 is similar to that regarding the twisting assembly 900 for the embodiment of tourniquet 30, except through the slot 1092 of twisting part 1050 instead of the slots 992 and 994 of the twisting part 900.

The elongated bar portion 1082 of the windlass portion 1080 is adapted to correspond and engage with diametrically opposite pairs of the plurality of teeth 1040 of the base part 1010. The elongated bar portion 1082 of the windlass portion 1080 can be fully engaged with two of the plurality of teeth 1040 of the base part 1010, as illustrated in FIG. 48. Windlass portion 1080 and the plurality of teeth 1040 can cooperate as a ratcheting system for the twisting of the twisting part 1050.

As illustrated in FIG. 48, with the elongated bar portion 1082 of the windlass portion 1080 of the twisting part 1050 in a fully engaged position with two diametrically opposite teeth of the plurality of teeth 1040 of the base part 1010, when the twisting part 1050 is attempted to be turned by hand using the windlass portion 1080 in a counter-clockwise direction (looking downward as in the view of FIG. 48), the curved surface 1083 of the elongated windlass engaging with the corresponding leading sloped surfaces 1044 of the two of the teeth 1040 tend to cooperate to redirect some of the rotational force upward with the counter-clockwise rotational movement to separate the ratcheting system between the windlass portion 1080 and the teeth 1040 and allow the twisting part 1050 to move upward and then turn about the upper portion 1030 of the base part 1010, allowing the surface 1083 of the windlass portion to slide or glide over the peak surface 1046 of each of the teeth 1040 as the twisting part is turned.

However, as illustrated in FIG. 48, the height of the leading vertical surface 1045 can provide an additional need to pull the twisting part 1050 upward before the windlass portion 1080 of the twisting part 1050 can be rotated more freely about the upper portion 1030 of the base part 1010. The height of the leading vertical surface 1045 on the teeth 1040 is a matter of design choice.

In this manner, the twisting part 1050 with the windlass portion 1080 can be rotated to slide relatively easily clockwise and successively over the peak surface 1046 of each of the teeth 1040, allowing the twisting part 1050 to be turned about the upper portion 1030 of the base part 1010 relatively easily relative to the base part 1010.

When the manual turning of the twisting part 1050 stops for any reason, such as by being let go, intentionally or by slipping or losing of manual grip, the tightening strap 100 (not shown in FIG. 48), especially with any prior twisting of the tightening strap 100 and tightening of the tourniquet around a limb, tends to draw and pull the twisting part 1050 downward such that the windlass portion 1080 is brought into a full engagement with two of the diametrically opposite of the teeth 1040 of the base part 1010.

However, with the elongated bar portion 1082 of the windlass portion 1080 of the twisting part 1050 in a fully engaged position with two diametrically opposite teeth of the plurality of teeth 1040 of the base part 1010, when the twisting part 1050 is attempted to be turned by hand in a clockwise direction (looking downward as in the view of FIG. 48), the curved surface 1083 of the windlass portion 1080 engaging with the corresponding trailing vertical surface 1048 of a tooth 1042 tends to block turning of the twisting part 1050 without redirecting any of the turning force upward and without tending to separate the ratcheting system of teeth. In this manner, the twisting part 1050 cannot be turned clockwise relative to the base part 1010. This prevents undesired untwisting of the tightening strap 100, unless the twisting assembly 1050 is manually grasped and forcefully pulled upward away from the teeth 1040 of the base part 1010, which becomes increasingly difficult as the twisting strap 100 is twisted and the tourniquet 40 is tightened around a limb L, as similarly illustrated for the tourniquet 10 in FIGS. 28-31. In addition, the teeth 1040 prevent the increasing strain of twisting of the tightening strap 100 from tending to untwist the twisting part of the twisting assembly and prevent undesired untwisting of the tightening strap 100 and, thereby, prevent undesired loosening of the tourniquet 40.

It can be understood, of course, that the allowing of a counter-clockwise direction of rotation relatively easily and clockwise direction of blocking rotation by the teeth 1040 of the ratcheting system between the base part 1010 and the twisting part 1050 of the twisting assembly 1000 is a matter of design preference. As can be appreciated, the twisting assembly 1000 could be designed and made with teeth that function to allow tightening of the tightening strap 100 in a clockwise twisting direction rather than a counter-clockwise twisting direction, as a matter of design and direction of operation preference. In contrast to the illustrated embodiment of FIGS. 45-48, a clockwise tightening operation would be more preferred as being a conventional clockwise tightening direction for turning of a handle, such as the handle of a conventional water tap or a conventional doorknob for a door.

As can be appreciated from the drawing, the operation of the tourniquet 40 is generally similar to that shown for tourniquet 10 and as illustrated in FIGS. 28-31, making allowances for the different structure of the twisting assembly 1000.

Fifth Embodiment of a Tourniquet with a Twisting Assembly

Turning now to FIGS. 49-51, a fifth example embodiment of a tourniquet according to the disclosure is illustrated.

FIG. 49 is an oblique upper side perspective view of a portion of a fifth embodiment of a tourniquet 50 according to the disclosure, wherein the tourniquet 50 is similar to the tourniquet 30 illustrated in FIGS. 33-44 except wherein the tourniquet 50 has a twisting assembly 1100 (instead of the twisting assembly 900), wherein the twisting assembly 1100 includes a base part 1110 attached to the pad assembly 550 and a twisting part 1150 attached to the twisting strap 100.

FIG. 50 is an end view of the twisting assembly 1100 attached to the pad assembly 550.

FIG. 51 is a top plan view of the twisting assembly 1100 attached to the pad assembly 550.

FIG. 52 is an oblique upper side view perspective of the twisting assembly 1100 illustrating how the base part 1110 can be used to lock the twisting part 1150 against untwisting, wherein for clarity of the illustration the twisting strap 100 is not shown.

In general, the twisting assembly 1100 is similar to the twisting assembly 1000 except for the shape and profile of the teeth.

The tourniquet 50 includes the same basic elements is similar to the tourniquet 30 illustrated in FIGS. 33-44 except wherein the tourniquet 50 has a twisting assembly 1100 instead of the twisting assembly 900 of the tourniquet 30. To illustrate the different twisting assembly 1100, on the portion of the tourniquet 50 having the twisting assembly 1100 is illustrated in detail in FIGS. 49-52. A twisting strap 100 is illustrated in FIGS. 49-51 threaded through the twisting assembly 1100 and the twisting assembly 1100 is shown attached to a pad assembly 550. The twisting strap 100 (not completely shown in FIGS. 49-51) and the pad assembly 550 (not completely shown in FIGS. 49-51) and the other elements of the tourniquet 50 are the same as for the tourniquet 30, the details of which are described in regarding the illustrations of FIGS. 33-44 regarding tourniquet 30.

In addition, the twisting strap 100 preferably has a stop 130 the same as in the tourniquet 30 and having a similar purpose, but a stop 130 is not illustrated in FIGS. 47-50.

As illustrated in FIGS. 49-52, the twisting assembly 1100 of tourniquet 50 is described in detail.

The twisting assembly 1100 includes a base part 1110 and a twisting part 1150.

The base part 1110 includes a lower saddle portion 1112, an upper portion 1130, and a plurality of teeth 1140 on the upper portion 1130.

The saddle portion 1112 of the base part 1110 is generally similar to the saddle portion 912 of the base part 910 of the tourniquet 30. The saddle portion 1112 of the base part 1110 has a generally horizontal bottom wall 1114 with an opening 1115 through the middle area of the bottom wall 1114. In this embodiment of the base part 1110, the bottom wall 1114 is substantially square having an overall length and width of about 1.5 inches (about 3.8 cm). A right side wall 1116 and left side wall 1118 are each downwardly extending from the bottom wall 1114. The right side wall 1116 and left side wall 1118 are of a relatively short height adapted to straddle a portion of the tightening strap 100. In the illustrated embodiment, the right side wall 1116 and left side wall 1118 each have a height of about 0.2 inch (about 0.5 cm).

In this embodiment, the saddle portion 1112 includes a first end tab 1121 and a second end tab 1122. The end tabs 1121 and 1122 extend substantially horizontally from the ends of the saddle portion 1112.

The first end tab 1121 is attached at a corner to an end of the right side wall 1116 by a connecting portion 1121A and attached at another corner to an end of the left side wall 1118 by a connecting portion 1121B. A first end slot 1123 is defined between the first end tab 1121, the bottom wall 1114, and the connecting portions 1121A and 1121B as shown in FIG. 49 and FIG. 51 and FIG. 52. The first end slot 1123 is adapted to allow the tightening strap 100 to be threaded through the slot 1123. In addition, a plurality of first end tab holes 1121C are formed in the first end tab 1121. Similar to as shown in FIG. 36 regarding the base part 900, the first end tab holes 1121C can be used to sew a first thread 1128 between the first end tab 1121 and the pad 560, thereby attaching the first end tab 1121 of the base part 1110 to the pad 560.

Symmetrically, the second end tab 1122 is attached at a corner to an end of the right side wall 1116 by a connecting portion 1122A and attached at another corner to an end of the left side wall 1118 by a connecting portion 1122B. A second end slot 1124 (not clearly visible in the figures) is defined between the first end tab 1122, the bottom wall 1114, and the connecting portions (not clearly visible in the figures). The second end slot 1124 is adapted to allow the tightening strap 100 to be threaded through the slot 1124. In addition, a plurality of second end tab holes 1122C are formed in the first end tab 1122. Similar to as shown in FIG. 36 regarding the base part 900, the second end tab holes 1122C can be used to sew a second thread 1129 between the second end tab 1122 and the pad 560, thereby attaching the second end tab 1122 of the base part 1110 to the pad 560.

Continuing to refer to FIGS. 49-52, the base part 1110 includes an upper portion 1130. The upper portion 1130 has a cylindrical wall 1132 defining an exterior cylindrical wall surface 1134, defining an interior cylindrical wall surface 1136, and an opening 1137 through the upper portion 1130 and connecting through to the opening 1115 in the saddle portion 1110. In this embodiment, the height of the upper portion 1130 is about 0.5 inch (1.2 cm) to about 1 inch (2.5 cm)

Formed or positioned on the upper end of the cylindrical wall 1132 of the upper portion 1130 are a plurality of circumferentially disposed, upwardly facing, teeth 1140. In the illustrated embodiment, the teeth 1140 are integrally formed at the upper portion of the cylindrical wall 1132.

As illustrated, for example in FIG. 49 and FIG. 52, each tooth 1142 of the plurality of teeth 1140 has a leading, upwardly sloped surface 1144 (counter-clockwise looking downward toward the saddle portion 1110), a peak surface 1146, and a trailing curved surface 1148. According, each of the teeth 1140 has a generally wave-like or wave-shaped profile. (The embodiment of the twisting assembly 1100 does not have vertical surfaces corresponding to the vertical surfaces 1045 and 1047 of the twisting assembly 1000.) The operation of the plurality of upwardly facing teeth 1140 can be understood from the FIGS. 49-52 and will hereinafter be described in detail.

The twisting part 1150 includes at least a windlass portion 1180. The windlass portion 1180 includes an elongated bar portion 1182 that can be oriented generally horizontally. The windlass portion 1180 has a curved surface 1183 of the elongated central bar portion selected or adapted for interacting and engaging with the teeth 1140 of the base part 1110. The windlass portion 1180 provides a handle for twisting of the twisting part 1150 of the twisting assembly 1100, which can be manually operated by a person's hand.

In addition, the twisting part 1150 includes a tightening strap slot 1192, where the twisting strap slot is through a middle portion of the elongated bar portion 1182 of the windlass portion 1180. The threading of the twisting strap 100 through the twisting assembly 1100 is similar to that regarding the twisting assembly 900 for the embodiment of tourniquet 30, except through the slot 1192 of twisting part 1150 instead of the slots 992 and 994 of the twisting part 900.

The elongated bar portion 1182 of the windlass portion 1180 is adapted to correspond and engage with diametrically opposite pairs of the plurality of teeth 1140 of the base part 1110. The elongated bar portion 1182 of the windlass portion 1180 can be fully engaged with two of the plurality of teeth 1140 of the base part 1110, as illustrated in FIG. 52. Windlass portion 1180 and the plurality of teeth 1140 can cooperate as a ratcheting system for the twisting of the twisting part 1150.

As illustrated in FIG. 52, with the elongated bar portion 1182 of the windlass portion 1180 of the twisting part 1150 in a fully engaged position with two diametrically opposite teeth of the plurality of teeth 1140 of the base part 1110, when the twisting part 1150 is attempted to be turned by hand using the windlass portion 1180 in a counter-clockwise direction (looking downward as in the view of FIG. 52), the curved surface 1183 of the elongated windlass engaging with the corresponding leading sloped surfaces 1144 of the two of the teeth 1140 tend to cooperate to redirect some of the rotational force upward with the counter-clockwise rotational movement to separate the ratcheting system between the windlass portion 1180 and the teeth 1140 and allow the twisting part 1150 to move upward and then turn about the upper portion 1130 of the base part 1110, allowing the surface 1183 of the windlass portion to slide or glide over the peak surface 1146 of each of the teeth 1140 as the twisting part is turned.

In this manner, the twisting part 1150 with the windlass portion 1180 can be rotated to slide relatively easily clockwise and successively over the peak surface 1146 of each of the teeth 1140, allowing the twisting part 1150 to be turned about the upper portion 1130 of the base part 1110 relatively easily relative to the base part 1110.

When the manual turning of the twisting part 1150 stops for any reason, such as by being let go, intentionally or by slipping or losing of manual grip, the tightening strap 100 (not shown in FIG. 52), especially with any prior twisting of the tightening strap 100 and tightening of the tourniquet around a limb, tends to draw and pull the twisting part 1150 downward such that the windlass portion 1180 is brought into a full engagement with two of the diametrically opposite of the teeth 1140 of the base part 1110.

However, with the elongated bar portion 1182 of the windlass portion 1180 of the twisting part 1150 in a fully engaged position with two diametrically opposite teeth of the plurality of teeth 1140 of the base part 1110, when the twisting part 1150 is attempted to be turned by hand in a clockwise direction (looking downward as in the view of FIG. 52), the curved surface 1183 of the windlass portion 1180 engaging with the corresponding trailing vertical surface 1148 of a tooth 1142 tends to block turning of the twisting part 1150 without redirecting any of the turning force upward and without tending to separate the ratcheting system of teeth. In this manner, the twisting part 1150 cannot be turned clockwise relative to the base part 1110. This prevents undesired untwisting of the tightening strap 100, unless the twisting assembly 1150 is manually grasped and forcefully pulled upward away from the teeth 1140 of the base part 1110, which becomes increasingly difficult as the twisting strap 100 is twisted and the tourniquet 50 is tightened around a limb L, as similarly illustrated for the tourniquet 10 in FIGS. 28-31. In addition, the teeth 1140 prevent the increasing strain of twisting of the tightening strap 100 from tending to untwist the twisting part of the twisting assembly and prevent undesired untwisting of the tightening strap 100 and, thereby, prevent undesired loosening of the tourniquet 50.

It can be understood, of course, that the allowing of a counter-clockwise direction of rotation relatively easily and clockwise direction of blocking rotation by the teeth 1140 of the ratcheting system between the base part 1110 and the twisting part 1150 of the twisting assembly 1100 is a matter of design preference. As can be appreciated, the twisting assembly 1100 could be designed and made with teeth that function to allow tightening of the tightening strap 100 in a clockwise twisting direction rather than a counter-clockwise twisting direction, as a matter of design and direction of operation preference. In contrast to the illustrated embodiment of FIGS. 49-52, a clockwise tightening operation would be more preferred as being a conventional clockwise tightening direction for turning of a handle, such as the handle of a conventional water tap or a conventional doorknob for a door.

As can be appreciated from the drawing, the operation of the tourniquet 50 is generally similar to that shown for tourniquet 10 and as illustrated in FIGS. 28-31, making allowances for the different structure of the twisting assembly 1100.

Principle of Spanish Windlass

FIGS. 53-54 (prior art) illustrate the operating principle of a Spanish windlass for twisting of a rope, wherein the twisting can be used for tightening the rope between two objects or for drawing the two objects closer together.

Referring to FIG. 53 (prior art), in simplest form, an example of a Spanish windlass 70 is a rod or wooden stick. The Spanish windlass 70 (for example, a wooden stick) is positioned adjacent to a rope 80 having ends 81 and 82, as illustrated, and rotating the Spanish windlass 70 about arrow J about an axis generally perpendicular to the length of the rope 80 between ends 81 and 82. The ends 81 and 82 of the rope 80 can be tied to other objects (not shown in FIG. 53). If desired, the direction of rotation of the windlass 70 can be the opposite direction of arrow J, as the direction makes no difference to the principle of operation of a Spanish windlass.

FIG. 54 (prior art) is an illustration of the Spanish windlass 70 of FIG. 53 wherein the rope 80 has been twisted to form twisted portion 85 by turning of the Spanish windlass 70. The twisting of the rope 80 about itself by the turning of the Spanish windlass 70 shortens the overall length of the rope 80, which shortening can be used to draw and tighten the two ends 81 and 82 of the rope 80 between any other objects. Of course, the Spanish windlass 70 and the rope 72 should be sufficiently strong for the particular purpose of use.

TABLE OF REFERENCE NUMBERS

For convenient reference, a listing of the reference numbers and elements described in one or more of the figures of the drawing is provided in Table 1.

TABLE 1

Reference Listing

| Embodiment | Reference | Element |
|---|---|---|
| First Embodiment: FIGS. 1-25 | 10 | a first embodiment of a tourniquet according to the disclosure |
| | 52 | tourniquet loop formed by tightening strap 100 and cinch strap 200 |
| | 54 | cinch strap loop formed by cinch strap 200 |
| | 100 | first strap (also referred to as a "tightening" strap or "twisting" strap for convenient reference and to distinguish from the "cinch" strap 200) |
| | 101 | first end (lengthwise) of tightening strap 100 (adjacent to buckle 800) |
| | 102 | second end (lengthwise) of tightening strap 100 (adjacent to D-ring 300) |
| | 103 | middle portion (lengthwise) of tightening strap 100 |
| | 110 | loop sewn or otherwise formed at first end 101 of tightening strap 100 for connecting first end 101 to buckle 800 |
| | 120 | loop sewn or otherwise formed at second end 102 of tightening strap 100 for connecting second end 102 to D-ring 300 |
| | 200 | second strap (also referred to as a "cinch" strap for convenient reference and to distinguish from the "tourniquet" strap 100) |
| | 201 | first end (lengthwise) of cinch strap 200 |
| | 202 | second end (lengthwise) of cinch strap 200 |
| | 203 | middle portion (lengthwise) of cinch strap 200 |
| | 210 | loop sewn or otherwise formed at first end 201 of cinch strap 200 for connecting first end 201 to buckle 800 |
| | 220 | loop sewn or otherwise formed at second end 202 of cinch strap 200 for connecting second end 202 to D-ring 400 |
| | 240 | keeper, for example, a plastic keeper or an elastic band to help keep cinch strap loop closed relative to tourniquet loop 52, preferably the keeper being weak and breakable |
| | 300 | D-Ring for connecting second end 102 of tightening strap 100 and middle portion 203 of cinch strap 200 |
| | 400 | D-ring at second end 202 (free end) of cinch strap 200 |
| | 500 | first embodiment of a pad assembly |
| | 510 | Pad |
| | 511 | first end (lengthwise) of pad 510 |
| | 512 | second end (lengthwise) of pad 510 |
| | 513 | middle portion (lengthwise) of pad 510 |
| | 515 | stitching or other fastening of end 101 of tightening strap 100 to first end 511 of pad 510 |
| | 520 | cover on second end 512 of pad 510 |
| | 521 | first end (lengthwise) of cover 520 |
| | 522 | second end (lengthwise) of cover 520 |
| | 525 | sleeve formed by pad 510 and cover 520, through which a middle portion 103 of the tightening strap 100 can be threaded |
| | 600 | a first embodiment of a twisting assembly |
| | 610 | base part of twisting assembly 600 |
| | 620 | saddle portion of base part 610 for connecting to holding strap 700 |
| | 622 | bottom wall of saddle portion 620 |
| | 623 | opening in bottom wall 622 of saddle portion 620 |
| | 624 | right side wall of saddle portion 620 |
| | 625 | left side wall of saddle portion 620 |
| | 626 | right side holding strap slot in right side wall 624 |
| | 627 | left side holding strap slot in left side wall 625 |
| | 630 | socket portion (female) of base part 610, which can function as a lower axial alignment portion for the hub portion (male) of the twisting part 660 |
| | 632 | cylindrical wall of socket portion 630 |
| | 634 | cylindrical inner wall surface of cylindrical wall 632 |
| | 636 | interior cylindrical opening through socket portion 630 |
| | 640 | plurality of lower teeth on interior of cylindrical wall 632 of socket portion 630 |
| | 642 | a tooth of the plurality of lower teeth 640 |
| | 644 | leading sloped surface of the tooth 642 of the base part 610 allowing for sliding of a corresponding leading sloped surface 675 of an upper tooth 672 of the twisting part 650 clockwise (looking downward) and adapted for clockwise turning (for tightening of the tightening strap 100) |
| | 646 | peak of the tooth 642 |
| | 648 | trailing vertical surface of tooth 642 (looking downward) adapted for stopping of counter-clockwise turning (for stopping of loosening of the tightening strap 100) |
| | 650 | twisting part of twisting assembly 600 |

TABLE 1-continued

Reference Listing

| Embodiment | Reference | Element |
|---|---|---|
| | 660 | hub portion (male) of twisting part 650, which can function as an upper axial alignment portion for the twisting part 650 in the socket portion (female) of the base part 610 |
| | 662 | cylindrical wall of hub portion 660 |
| | 664 | exterior wall surface of hub portion 660 for sliding and turning inside the interior cylindrical wall surface 634 of socket portion 630 of base part 610 |
| | 665 | interior opening through hub portion 660 |
| | 670 | plurality of upper teeth on bottom of cylindrical wall 662 of hub portion |
| | 672 | a tooth of the plurality of upper teeth 670 |
| | 674 | leading sloped surface of the tooth 672 of twisting part 650 allowing for sliding of the sloped surface of the twisting part 650 clockwise (looking downward) over the corresponding sloped surface 644 of a tooth 642 |
| | 676 | peak of the tooth 672 |
| | 678 | trailing vertical surface of the tooth 672 of the twisting part 650 adapted for stopping of counter-clockwise turning of the twisting part 650against the corresponding trailing vertical surface 648 of a corresponding tooth 642 of the base part 610 |
| | 680 | windlass portion of twisting part 650 |
| | 682 | elongated central bar portion (horizontal) of windlass portion 680 |
| | 684 | first leg (vertical, for example, downwardly extending) of windlass portion 680 |
| | 685 | second leg (vertical, for example, downwardly extending) of windlass portion 680 |
| | 684A | first surface on first leg 684 |
| | 684B | second surface on first leg 684 opposite to first surface 684A |
| | 685A | first surface on second leg 685 |
| | 685B | second surface on second leg 685 opposite to first surface 685A |
| | 690 | upper wall portion of twisting part 650 |
| | 692 | first tightening strap slot through upper wall portion 690 |
| | 694 | second tightening strap slot through upper wall portion 690 |
| | 699 | clearance between interior cylindrical wall surface 634 of socket portion 630 and exterior cylindrical wall surface 664 of hub portion 660 |
| | 700 | third strap (also referred to as a "holding" strap for convenient reference) for the base part 610 of twisting assembly 600 to hold the base part 610 against twisting of the base part 610 relative to the pad 510 and, thereby, to hold the base part 610 against twisting relative to the tourniquet loop 52 formed by the tourniquet 10 when positioned around a limb |
| | 701 | first end (lengthwise) of holding strap 700 |
| | 702 | second end (lengthwise) of holding strap 700 |
| | 703 | middle portion (lengthwise) of holding strap 700 |
| | 710 | hooks (of a hook-and-loop fastening system such as VELCRO brand) on holding strap 700 |
| | 720 | loops (of a hook-and-loop fastening system such as VELCRO brand) on holding strap 700 |
| | 800 | side-release buckle (also known as a side-squeeze buckle), wherein the buckle includes a one-way strap adjuster portion 860 |
| | 810 | female part of buckle 800, wherein the female part can be attached to the first end 101 of the tightening strap 100 |
| | 820 | body forming a socket portion of female part 810 of buckle 800 |
| | 822 | top wall of body 820 |
| | 824 | bottom wall of body 820 |
| | 826 | right side wall of body 820 |
| | 827 | left side wall of body 820 |
| | 828 | right side opening right side wall 826 of body 820 |
| | 829 | left side opening left side wall 828 of body 820 |
| | 830 | integrally formed square ring for attaching tightening strap 100, which is attached to the pad 510 |
| | 850 | male part of buckle 800, wherein the male part can be attached to the first end 201 of cinch strap 200 |
| | 852 | center guide of male part 850 |
| | 853 | structural bar |
| | 854 | right side arm with releasing finger surface 858 operable by a thumb or finger as the thumb and finger are squeezed together |
| | 855 | left side arm with releasing finger surface 859 operable by a thumb or finger as the thumb and finger are squeezed together |
| | 856 | right side engaging lip (on right side arm 854) for engaging a corresponding structure on female part of buckle |
| | 857 | left side engaging lip (on left side arm 856) for engaging a corresponding structure on female part of buckle |
| | 858 | right side releasing finger surface of right side arm 854 |
| | 859 | left side releasing finger surface of left side arm 856 |

TABLE 1-continued

Reference Listing

| Embodiment | Reference | Element |
|---|---|---|
| | 860 | one-way strap adjuster integrally formed with male part 850 of buckle 800 |
| | 861A | side wall |
| | 861B | side wall |
| | 862 | locking bar (having a toothed, notched, or etched edge) of one-way strap adjuster 860 for helping to engage a webbing material of the cinch strap 200 |
| | 863 | rear bar |
| | 864 | slot opening for threading and attaching first end 201 of cinch strap 200 |
| | 866 | slot opening for threading through a middle portion 203 of cinch strap 200 |
| Embodiment of a Male Part of a Buckle of tourniquet 10 without a Strap Adjuster: FIGS. 26-27 | 851 | male part of buckle 800, wherein the male part can be attached to the first end 201 of cinch strap 200 |
| | 852 | center guide of male part 850 |
| | 853 | structural bar |
| | 854 | right side arm with releasing finger surface 858 operable by a thumb or finger as the thumb and finger are squeezed together |
| | 855 | left side arm with releasing finger surface 859 operable by a thumb or finger as the thumb and finger are squeezed together |
| | 856 | right side engaging lip (on right side arm 854) for engaging a corresponding structure on female part of buckle |
| | 857 | left side engaging lip (on left side arm 856) for engaging a corresponding structure on female part of buckle |
| | 858 | right side releasing finger surface of right side arm 854 |
| | 859 | left side releasing finger surface of left side arm 856 |
| | 867 | slot opening |
| Method FIGS. 28-31 | A, B, C, D, E, F, and G | various direction arrows indicating operation of tourniquet 10 |
| | L | limb, for example, thigh of leg of a human |
| Second Embodiment: FIG. 32 | 20 | a second embodiment of a tourniquet according to the disclosure |
| | 130 | stop attached to or formed in tightening strap 100, for example, by stitching to form a folded portion in the tightening strap for forming the stop |
| | 550 | a second embodiment of a pad assembly |
| | 560 | pad of pad assembly 550 |
| | 561 | first end (lengthwise) of pad 560 |
| | 562 | second end (lengthwise) of pad 560 |
| | 563 | middle portion (lengthwise) of pad 560 |
| | 570 | second cover on second end 562 of pad 560 |
| | 571 | first end (lengthwise) of cover 570 |
| | 572 | second end (lengthwise) of cover 570 |
| | 575 | second sleeve formed by second end 561 of pad 560 and cover 570 |
| | 580 | first cover on first end 561 of pad 560 |
| | 581 | first end (lengthwise) of cover 580 |
| | 582 | second end (lengthwise) of cover 580 |
| | 585 | first sleeve (formed by first end 561 pad and cover 580) |
| Third Embodiment: FIGS. 33-44 | 30 | a third embodiment of a tourniquet according to the disclosure |
| | 330 | loop (an alternative example to a D-ring) for connecting tightening strap 100 and cinch strap 200 |
| | 900 | a second embodiment of a twisting assembly |
| | 910 | base part of twisting assembly 900 |
| | 912 | saddle portion (of base part 910) for connecting to holding strap |
| | 914 | bottom wall of saddle portion 912 |
| | 915 | opening in bottom wall of saddle portion 912 |
| | 916 | right side wall of saddle portion 912 |
| | 918 | left side wall of saddle portion 912 |
| | 921 | first end tab of saddle portion 912 |
| | 922 | second end tab of saddle portion 912 |
| | 921A | right connecting portion for first end tab 921 to the right side wall 916 of saddle portion 912 (right connecting portion 922A for second end tab 922 is similar, but not visible in FIG. 36) |
| | 921B | left connecting portion for first end tab 921 to the left side wall 918 of saddle portion 912 (left connecting portion 922B for second end tab 922 is similar, but not visible in FIG. 36) |
| | 921C | first end tab holes (for thread) in first end tab 921 |
| | 922C | second end tab holes (for thread) in second end tab 922 |
| | 923 | first end slot in saddle portion 912 for tightening strap 100 |
| | 924 | second end slot in saddle portion 912 for tightening strap 100 |
| | 928 | thread for attaching first end tab holes 921C to pad 560 |
| | 929 | thread for attaching second end tab holes 922C to pad 560 |

TABLE 1-continued

Reference Listing

| Embodiment | Reference | Element |
|---|---|---|
| | 930 | male portion of base part 910 of twisting assembly 900 (a lower axial alignment portion) |
| | 932 | cylindrical wall of male portion 930 |
| | 934 | exterior (cylindrical) wall surface of male portion 930 |
| | 936 | interior (cylindrical) wall surface of male portion 930 |
| | 937 | interior (cylindrical) opening through male portion 930 |
| | 940 | plurality of lower teeth (on exterior of cylindrical wall 932 of male portion 930) |
| | 942 | a tooth of the plurality of lower teeth 940 |
| | 944 | leading sloped surface of the tooth 942 of the base part allowing for sliding of the corresponding leading sloped surface of a tooth of the twisting part clockwise (looking downward) adapted for clockwise tightening |
| | 946 | peak of the tooth 942 |
| | 948 | trailing vertical surface of tooth 942 (looking downward) adapted for stopping counter-clockwise loosening |
| | 950 | twisting part of twisting assembly 900 |
| | 960 | female portion (a upper axial alignment portion) |
| | 962 | cylindrical wall of female portion 960 of twisting part 950 |
| | 964 | interior wall surface of cylindrical wall 962 for sliding and turning outside exterior cylindrical wall 934 of male portion 930 of base part 910 |
| | 965 | interior opening (through female portion 960) |
| | 970 | plurality of upper teeth (on bottom of cylindrical wall 962 of female portion 960) |
| | 972 | a tooth of the plurality of upper teeth 970 |
| | 974 | leading sloped surface of the tooth 972 of twisting part 950 allowing for sliding of the sloped surface of the twisting part 950 clockwise (looking downward) over the corresponding sloped surface 944 of the tooth 942 |
| | 976 | peak of the tooth 972 |
| | 978 | trailing vertical surface of the tooth 972 of the twisting part 950 adapted for stopping counter-clockwise loosening against the corresponding trailing vertical surface 948 of a corresponding tooth 942 of the base part 910 |
| | 980 | windlass portion of twisting part 950 |
| | 982 | elongated central bar portion (horizontal) of windlass portion 980 |
| | 984 | first leg (vertical, for example, downwardly extending) of windlass portion 980 |
| | 985 | second leg (vertical, for example, downwardly extending) of windlass portion 980 |
| | 984A | first surface on first leg 984 |
| | 984B | second surface on first leg 984 (opposite to first surface 684A) |
| | 985A | first surface on second leg 985 |
| | 985B | second surface on second leg 985 (opposite to first surface 685A) |
| | 990 | upper wall portion of twisting part 950 |
| | 992 | first tightening strap slot through upper wall portion 990 |
| | 994 | second tightening strap slot through upper wall portion 990 |
| Fourth Embodiment: FIGS. 45-48 | 40 | a fourth embodiment of a tourniquet according to the disclosure |
| | 1000 | a third embodiment of a twisting assembly |
| | 1010 | base part of twisting assembly 1000 |
| | 1012 | saddle portion (of base part 1010) for connecting to holding strap |
| | 1014 | bottom wall of saddle portion 1012 |
| | 1015 | opening in bottom wall of saddle portion 1012 |
| | 1016 | right side wall of saddle portion 1012 |
| | 1018 | left side wall of saddle portion 1012 |
| | 1021 | first end tab of saddle portion 1012 |
| | 1022 | second end tab of saddle portion 1012 |
| | 1021A | right connecting portion for first end tab 1021 to the right side wall 1016 of saddle portion 1012 (not clearly visible in FIGS. 45-48, but similar to right connecting portion 921A of base part 910 shown in FIG. 34) |
| | 1021B | left connecting portion for first end tab 1021 to the left side wall 1018 of saddle portion 1012 (not clearly visible in FIGS. 45-48, but similar to left connecting portion 921B of base part 910 shown in FIG. 34) |
| | 1021C | first end tab holes (for thread) in first end tab 1021 |
| | 1022A | right connecting portion for first end tab 1022 to the right side wall 1016 of saddle portion 1012 (not clearly visible in FIGS. 43-47, but similar to right connecting portion 921A of base part 910 shown in FIG. 34) |
| | 1022B | left connecting portion for first end tab 1021 to the left side wall 1018 of saddle portion 1012 (not clearly visible in FIGS. 43-47, but similar to left connecting portion 921B of base part 910 shown in FIG. 34) |

TABLE 1-continued

Reference Listing

| Embodiment | Reference | Element |
|---|---|---|
| | 1022C | second end tab holes (for thread) in second end tab 1022 |
| | 1023 | first end slot in saddle portion 1012 for tightening strap 100 |
| | 1024 | second end slot (similar to first end slot 1023 but not visible in FIGS. 45-48) in saddle portion 1012 for tightening strap 100 |
| | 1028 | thread for attaching first end tab holes 1021C to pad 560 |
| | 1029 | thread for attaching second end tab holes 1022C to pad 560 |
| | 1030 | upper portion of base part 1010 of twisting assembly 1000 |
| | 1032 | cylindrical wall of upper portion 1030 |
| | 1034 | exterior (cylindrical) wall surface of upper portion 1030 |
| | 1036 | interior (cylindrical) wall surface of upper portion 1030 |
| | 1037 | interior (cylindrical) opening through upper portion 1030 |
| | 1040 | plurality of teeth circumferentially located on cylindrical wall 1032 of upper portion 1030 |
| | 1042 | a tooth of the plurality of teeth 1040 |
| | 1044 | leading sloped surface of the tooth 1042 allowing for sliding of the windlass portion 1080 of the twisting part 1050 counter-clockwise (looking downward) adapted for counter-clockwise tightening |
| | 1045 | leading vertical surface of the tooth 1042 between the leading sloped surface 1044 of the tooth 1042 to the peak surface 1046 of the tooth 1042 |
| | 1046 | peak surface of the tooth 1042 |
| | 1047 | trailing vertical surface of the tooth 1042 between the peak surface 1046 of the tooth and the trailing curved surface 1048 |
| | 1048 | trailing curved surface of the tooth 1042 (looking downward), wherein the trailing curved surface forms a notch under the peak surface 1046 of the tooth 1042 adapted for engaging and stopping clockwise turning of the windlass portion 1080 of the twisting part 1050 when the windlass portion is positioned adjacent the trailing curved surface |
| | 1050 | twisting part of twisting assembly 1000 |
| | 1080 | windlass portion of twisting part 1050 |
| | 1082 | elongated bar portion (horizontal) of windlass portion 1080 |
| | 1083 | curved surface of elongated central bar portion 1082 of windlass portion 1080 |
| | 1092 | slot through windlass portion 1080 for operatively connecting (threading) of tightening strap 100 |
| | H | direction arrow for operation of tourniquet 40 in counter-clockwise direction |
| Fifth Embodiment: FIGS. 49-52 | 50 | a fifth embodiment of a tourniquet according to the disclosure |
| | 1100 | a fourth embodiment of a twisting assembly |
| | 1110 | base part of twisting assembly 1100 |
| | 1112 | saddle portion (of base part 1110) for connecting to holding strap |
| | 1114 | bottom wall of saddle portion 1112 |
| | 1115 | opening in bottom wall of saddle portion 1112 |
| | 1116 | right side wall of saddle portion 1112 |
| | 1118 | left side wall of saddle portion 1112 |
| | 1121 | first end tab of saddle portion 1112 |
| | 1122 | second end tab of saddle portion 1112 |
| | 1121A | right connecting portion for first end tab 1121 to the right side wall 1116 of saddle portion 1112 (not clearly visible in FIGS. 49-52, but similar to right connecting portion 921A of base part 910 shown in FIG. 34) |
| | 1121B | left connecting portion for first end tab 1121 to the left side wall 1118 of saddle portion 1112 (not clearly visible in FIGS. 49-52, but similar to left connecting portion 921B of base part 910 shown in FIG. 34) |
| | 1121C | first end tab holes (for thread) in first end tab 1121 |
| | 1122A | right connecting portion for first end tab 1122 to the right side wall 1116 of saddle portion 1112 (not clearly visible in FIGS. 49-52, but similar to right connecting portion 921A of base part 910 shown in FIG. 34) |
| | 1122B | left connecting portion for first end tab 1121 to the left side wall 1118 of saddle portion 1112 (not clearly visible in FIGS. 49-52, but similar to left connecting portion 921B of base part 910 shown in FIG. 34) |
| | 1122C | second end tab holes (for thread) in second end tab 1122 |
| | 1123 | first end slot in saddle portion 1112 for tightening strap 100 |
| | 1124 | second end slot in saddle portion 1112 for tightening strap 100 |
| | 1128 | thread for attaching first end tab holes 1121C to pad 560 |
| | 1129 | thread for attaching second end tab holes 1122C to pad 560 |
| | 1130 | upper portion of base part 1110 of twisting assembly 1100 (a lower axial alignment portion) |
| | 1132 | cylindrical wall of upper portion 1130 |
| | 1134 | exterior (cylindrical) wall surface of upper portion 1130 |

TABLE 1-continued

Reference Listing

| Embodiment | Reference | Element |
|---|---|---|
| | 1136 | interior (cylindrical) wall surface of upper portion 1130 |
| | 1140 | plurality of teeth circumferentially located on cylindrical wall 1132 of upper portion 1130 |
| | 1142 | a tooth of the plurality of teeth 1140 |
| | 1144 | leading sloped surface of the tooth 1142 allowing for sliding of the windlass portion 1180 of the twisting part 1150 counter-clockwise (looking downward) adapted for counter-clockwise tightening |
| | 1146 | peak surface of the tooth 1142 |
| | 1148 | trailing curved surface of the tooth 1142 (looking downward), wherein the trailing curved surface forms a notch under the peak surface 1146 of the tooth 1142 adapted for engaging and stopping clockwise turning of the windlass portion 1180 of the twisting part 1150 when the windlass portion is positioned adjacent the trailing curved surface |
| | 1150 | twisting part of twisting assembly 1100 |
| | 1180 | windlass portion of twisting part 1150 |
| | 1182 | elongated bar portion (horizontal) of windlass portion 1180 |
| | 1183 | curved surface of elongated bar portion 1182 of windlass portion 1180 |
| | 1192 | slot through windlass portion 1180 for operatively connecting (threading) of tightening strap 100 |
| | H | direction arrow for operation of tourniquet 50 in counter-clockwise direction |
| Spanish windlass operation: FIGS. 53-54 | 70 | Spanish windlass (or simply, "windlass") |
| | 80 | rope |
| | 81 | first end of rope 80 |
| | 82 | second end of rope 80 |
| | 85 | twisted portion of rope 80 after using Spanish windlass 70 |
| | J | direction arrow of rotating Spanish windlass 70 (shown in a clockwise direction, but counter-clockwise direction would work similarly) |

Interpretation, Definitions, and Usages

Principles of Interpretation

The words, terms, phrases, and other symbols used herein have their plain, ordinary meaning to persons of skill in the art of this disclosure, except to the extent explicitly and clearly defined in this disclosure, on the condition that even if explicitly defined in this disclosure, the specific context of a usage could still require a different or more specific meaning. The definitions provided are intended to help clarify—not confuse or be applied blindly without regard to the relevant context. All possible relevant senses of the multitude of words used in this disclosure may not be accounted for in a specific provided definition. The applicable sense or senses can depend on the specific context of the usage.

Initially, as a general aid to interpretation, the possible definitions of the words, phrases, and other symbols used herein are intended to be interpreted by reference to comprehensive general dictionaries of the English language published before or about the time of the earliest filing of this application for patent. A preferred dictionary is the American Heritage Dictionary of the English Language, 5$^{th}$ Edition (Houghton Mifflin Harcourt, 2019). Where several different general definitions are available, it is intended that the broadest definitions or senses be selected that are consistent with this disclosure and the description of the presently most-preferred embodiments, including without limitation as shown in a figure of any drawing.

After initially consulting such general dictionaries of the English language, it is intended that the words, phrases, or other symbols used herein be further interpreted or the most appropriate general definition or definitions be further selected by consulting technical dictionaries, encyclopedias, treatises, or relevant prior art to which the claimed invention pertains. If necessary to resolve any remaining doubt, utilizing the patent prosecution record may be helpful to select from among the possible interpretations.

Terms or phrases made up of more than one word (for example, compound terms or phrases or names) are sometimes not found in general dictionaries of the English language. Compound terms or names are to be interpreted as a whole, and not by parsing the separate words of the compound term, which might result in absurd and unintended interpretations. For example, in the context of railroad technology, a "coal car" does not mean a car made of coal but is well understood to mean the railroad car is for hauling coal. In general, compound terms are to be interpreted as they would be understood in the art and consistent with the usage in this specification.

Examining relevant general dictionaries, encyclopedias, treatises, prior art, and the patent record will make it possible to ascertain the appropriate meanings that would be attributed to the words and terms of the description and claims by those skilled in the art, and the intended full breadth of the words and terms will be more accurately determined. In addition, the improper importation of unintended limitations from the written description into the claims will be more easily avoided.

If there is any conflict in the usages of a word or term in this disclosure and one or more patent(s) or other documents that are incorporated by reference, the definitions that are consistent with the original material of this disclosure should be adopted in interpreting the original material of this disclosure, and the definitions that are consistent with the document incorporated by reference should be adopted in interpreting the material from that document.

Words of language often have multiple different senses. The selection of the applicable sense is usually understood from the particular context in which the word is used. If a word is specifically defined herein in a particular sense that does not reasonably apply in the context of a particular instance of usage elsewhere in the disclosure or claims, an applicable sense definition should be applied, not an inapplicable definition for a different context of usage. If any explicit definition herein is plainly obnoxious both to every ordinary meaning and to every technical meaning in the art for a usage in a particular context, the explicit definition herein should be disregarded as an obvious and unintended error.

Terms such as "first," "second," "third," etc. (adjective) may be assigned arbitrarily and are merely intended to differentiate between two or more components, parts, or steps that are otherwise similar or corresponding in nature, structure, function, or action. For example, the words "first" and "second" serve no other purpose and are not part of the name or description of the following name or descriptive terms. The mere use of the term "first" does not require there be any "second" similar or corresponding component, part, or step. Similarly, the mere use of the word "second" does not require there be any "first" or "third" similar or corresponding component, part, or step. Further, the mere use of the term "first" does not require the element or step be the very first in any sequence, but merely that it is at least one of the elements or steps. Similarly, the mere use of the terms "first" and "second" does not necessarily require any sequence. Accordingly, the mere use of such terms does not exclude intervening elements or steps between the "first" and "second" elements or steps, etc.

If there is a discrepancy between the written description and one or more figures of the drawing, a person of skill in the art would recognize that the drawing is essentially correct and a person of skill in the art can understand the operation of a tourniquet according to the disclosure from the figures of the drawing.

It should be understood that algebraic variables and other scientific symbols used herein are selected according to convention, or, if no convention, arbitrarily. For example, the algebraic variables "a" and "b" can be selected arbitrarily.

It should be understood that an element, part, component, or ingredient can have more than one characteristic and that it can be characterized or classified in different, independent respects. For example, an element can be characterized as elongated or flexible, in different aspects.

The headings and subheadings used in herein are intended for convenient reference but are not intended to be limiting.

Patent Terminology

A patent "claim" (noun) means either: (a) a statement of the subject matter for which legal protection is sought in an application for patent; or (b) a statement of the subject matter for which legal protection has been granted (that is, legally recognized) in an issued patent. A patent claim is distinguishable from other types of legal claims and distinguishable from non-legal claims, such as factual or medical claims.

"Disclosure" (noun) (of an application for patent) means the specification of the written description with any original claims and any drawings, as of the effective filing date of the subject matter of a claim. The purpose of the disclosure is to disclose, that is, to make known. The applicable national law may provide a more particular definition or requirements for a disclosure of a patent.

An "original claim" (noun phrase) of a patent is a claim that is filed at the time of filing an application. An original claim is also part of the original disclosure. For the purposes of disclosure, an original claim can be treated as disclosure; however, for the purposes of examination of patentability and interpretation of full scope of an issued patent, any claim should be interpreted as broadly as literally stated except for any obvious error or except as may be interpreted under the doctrine of equivalents. For the purposes of disclosure, all variations, combinations, and permutations in which one or more limitations, elements, clauses, and descriptive terms from one or more of the original claims is introduced into another original claim are part of the disclosure. For example, any original claim that is dependent on another original claim can be amended to include one or more limitations found in any other original claim that is dependent on the same original base claim.

"Invention" (noun) means: (1) the act or process of inventing; or (2) a new and useful article, manufacture, composition, machine, device, method, or process, or any new and useful improvement thereof.

"Patent" (noun) means: (1) a grant made by a government that confers upon the creator (or assignee) of an invention the right to exclude others from making, using, offering to sell, selling, or importing that invention within the territory of the government for a limited period of time; (b) letters patent; or (c) an invention protected by such a patent. The applicable national law may provide more particular requirements. The applicable national law may provide a more particular identification of the patent rights.

"Specification" (noun) means a written description of the ideas in an application or patent. The applicable national law may provide a more particular definition or requirements for a specification.

In a claim, the conjunction "and" (in the sense of a listing or grouping) is open to additional elements or steps, unless the context otherwise requires.

In a claim, only the specific use of the phrase "means for" or "step for"—without the recital of structure, material, or acts in support thereof—is intended to invoke the interpretation or construction under 35 USC § 112(f). For example, the terms "twisting assembly" or "tightening strap" are for the purposes of describe or naming an assembly or element and not intended to invoke such a construction, whereas "means for twisting" or "means for cinching" are intended to invoke the interpretation under 35 USC § 112(f).

Transitional Terminology

The words "comprising," "containing," "including," "having," "characterized by," and all grammatical variations thereof are intended to have an open, non-limiting meaning as to any unstated limitations.

In a claim, the transitional term "comprising," is inclusive or open-ended and does not exclude additional, un-recited elements or method steps. "Comprising" in claim language means the specified elements are essential, but other elements can be added and still form a construct within the scope of the claim. For example, a composition comprising an ingredient does not exclude it from having additional ingredients, an apparatus comprising a part does not exclude it from having additional parts, and a method having a step does not exclude it having additional steps.

In a claim, the transitional phrase "consisting essentially of" and all grammatical variations thereof are intended to limit the scope of a claim to the specified materials or steps and those that do not materially affect the basic and novel characteristic(s) of the claimed invention. A "consisting essentially of" claim occupies a middle ground between fully open claims using a "comprising" format and closed claims that are written in a "consisting of" format.

In a claim, the transitional phrase "consisting of" excludes any element, step, or ingredient not specified in the claim. For example, "consisting of" is defined as closing the claim to the inclusion of materials other than those recited except for impurities ordinarily associated therewith. For another example, a claim for a bone repair kit "consisting of" certain chemicals in a claim was infringed by a bone repair kit including a spatula in addition to the claimed chemicals because the presence of the spatula was unrelated to the subject matter of the claimed invention.

The phrase "selected from the group consisting of" (which is a kind of "Markush" grouping) means a list of alternative species within a grouping, even if the list includes the word "and." For example, "selected from the group consisting of: a, b, and c" means any one or more of "a, b, and c".

For the purposes of disclosure, however, such transitional phrases additionally subsume and include a disclosure of any more limited meanings. For example, a disclosure using the word "comprising" or like open-ended terms herein is intended to support a claim using any of the transitional terms "comprising," "consisting essentially of," or "consisting of." Similarly, a disclosure using the phrase "consisting essentially of" is intended to support a claim using the narrower phrase "consisting of."

Other Grammar

"Phrase" (noun) means a sequence of two or more words that have meaning, especially when forming part of a sentence. "Noun phrase" (noun) means a phrase formed by a noun and all its modifiers and determiners; broadly any syntactic element (such as a clause, clitic, pronoun, or zero element) with a noun's function (such as the subject of a verb or the object of a verb or preposition), for example, the phrase "coal car" for which the head is the noun "car." A noun phrase can be replaced by a single pronoun without rendering the sentence grammatically unacceptable.

The indefinite articles "a" or "an" mean at least one of the noun or noun phrase that the article introduces.

"Or" (conjunction) means: (1) (a) indicating an alternative, usually only before the last term of a series: hot or cold; this, that, or the other; (b) indicating the second of two alternatives, the first being preceded by either or whether; or (2) indicating a synonymous or equivalent expression.

For the purposes of disclosure, conjunctions "or" (in the sense of an alternative) and "and" (in the sense of a listing or grouping) can be interpreted first as open and non-limiting to other or additional possibilities, and, interpreted second, as closed and limiting.

For the purposes of disclosure, where elements are presented as groups or lists, for example, in "Markush group" format, each and every possible subgrouping of the grouped or listed elements is also disclosed as if set forth in separate lists. For example, where a disclosed group of three elements is disclosed, any subgrouping of one or two of the three elements is disclosed. For the purposes of disclosure, in various embodiments exactly one member of a group is present in, employed in or otherwise relevant to a given product or process. In various embodiments one, more than one, or all of a group's members are present in, employed in, or otherwise relevant to a given product or process.

The phrase "one or more" of something means an alternative grouping of the something.

In a "positive" (inclusionary) statement of a patent claim, an alternative grouping is met if any one or more of the statements of the grouping are met. For example, example, "feeling tight or cutting" means either one or both of these feelings.

In a "negative" (exclusionary) statement of a patent claim, however, an alternative grouping is met only if all the statements of the grouping are met. For example, "not feeling tight or cutting" means not tight and not feeling cutting.

Numbers, Numerical Limits, Numerical Ranges, and Percentages, and Pluralities

"About" or "approximately" (adverbs) regarding a number or measurement means within 10% of the number or measurement.

Each numerical value should be read once as modified by the term "about" (unless already expressly so modified), and then read again as not so modified, unless otherwise indicated in context.

"Significant figures" (noun phrase) are digits of a number that carry meaning contributing to its measurement resolution. This includes all digits except any leading zeros, trailing zeros when they are merely placeholders to indicate the scale of the number, spurious digits introduced, for example, by calculations carried out to greater precision than that of the original data, and any digits of measurements reported to a greater precision than the measuring equipment supports.

Where a numerical limit of degree or measurement is disclosed, any number and any limit falling within the expressly stated limit is also intended to be specifically disclosed. For example, every expressly stated limit (in the form of "less than a" or "at most a" or "greater than b" or "at least b" or any similar expressions, where "a" and "b" represent numerical values of degree or measurement) is to be understood to set forth every number encompassed by the expressly stated numerical limit. For example, "less than 10" is understood to additionally disclose "less than 9.97," "less than 7.2," "less than 0.001," "zero," and, if physically possible in the context, negative numbers, such as "minus 29.3."

Where a numerical range of degree or measurement with a lower limit and an upper limit is disclosed, any number and any range falling within the expressly stated numerical range is also intended to be specifically disclosed. Furthermore, unless otherwise indicated or otherwise evident from the context and understanding of one of ordinary skill in the art, values that are expressed as ranges can assume any specific value or sub-range within the stated range, to the hundredth of the unit of the range, unless the context clearly dictates otherwise. For example, every expressly stated numerical range of values (in the form "a to b," or "about a to about b," or "about a to b," or "approximately a to b," or any similar expressions, where "a" and "b" represent numerical values of degree or measurement) is to be understood to set forth every number and range encompassed in the expressly stated numerical range. For example, an expressly stated disclosure of "in the range of 10 to 20" is understood to additionally disclose, for example, "10," and "10 to 10.01," and "11.3," and "14 to 16.95," and "16.4 to 18.6," and "17.43 to 19.7," and "20."

Where a numerical limit is disclosed as a percentage of degree or measurement as a portion of a whole, it is based on the percentage range of 0% (zero or none of the whole) to 100% (all of the whole). For example, every expressly stated numerical limit of a percentage (in the form of "less than a %" or "at most a %" or "greater than b %" or "at least b %" or any similar expressions, where "a" and "b" represent numerical values of the percentage) is to be understood to set forth every number encompassed by the expressly stated limit from 0 (zero) to "a" or from "b" to 100, as indicated by the percentage context, except, however, that the lower limit of none or the upper limit of 100% can be otherwise limited by other requirements of the claim. For example, in a composition comprising "at least 10% by weight of a first ingredient," "at least 20% by weight of a second ingredient," and "less than 30% by weight of a third ingredient," it should be understood the first ingredient can be in the range of 10-80% by weight, the second ingredient can be in the range of 20-90% by weight, and the third ingredient can be in the range of 0-30% by weight.

Where a numerical limit is disclosed as a percentage of degree or measurement as a relation to another degree or measurement, it is to be understood as not limited to 0% or to 100%. For example, a container can have a height that is "at least 200% of its width" or an ingredient can be present in a concentration that is "greater than 120% of the concentration of" another ingredient.

Where numerical limits, ranges, or percentages are disclosed, the endpoint numbers are included. For example, "less than 10%" means and includes 10% or any amount less than 10% and means and includes 0% (none), except in cases where the endpoint would overlap with the endpoint of another numerical limit, range, or percentage, in which case the endpoint of "less than x %" means any percentage at least one hundredth of the unit less than the endpoint. For example, if one range is "10 to 30%" and another is "less than 10%," to avoid overlapping endpoints, then in this case the "less than 10%" means 9.99% or less.

Where a numerical limit of degree or measurement is disclosed with respect to a plurality or grouping of disclosed entities, the numerical limit of degree or measurement is also intended to be specifically disclosed regarding each entity of the plurality or grouping of disclosed entities collectively and independently. For example, if a numerical limit of "less than 10% of alcohols" is disclosed, it includes independent disclosure of "less than 10% of any alcohol," "less than 10% of methanol," "less than 10% of ethanol," "less than 10% of propanol," and less "than 10% of all alcohols." For another example, "less than 10% of alcohols" includes independent disclosure of "less than 10% of methanol," "less than 5% of methanol," "less than 4% of ethanol," "less than 1% of ethanol," "less than 6.5% of propanol," "less than 9% of menthol," and "0% (none) of sorbitol."

General Terminology

"Acceptable" (adjective) means adequate to satisfy a need, requirement, or standard, as in at least sufficient.

"Alternative" (adjective) means allowing for a choice between two or more things from which the choice can be made.

"Apparatus" (noun) means an integrated group of materials or devices for a particular purpose.

"Apply" (verb) means to bring into contact with something; put on.

"Article" (noun) means: (1) an individual thing or element of a class; a particular object or item: an article of clothing; articles of food; or (2) in grammar, (a) the part of speech used to indicate nouns and to specify their application; or (b) any of the words belonging to this part of speech.

"Assembly" (noun) means: (1) (a) the act of assembling; or (b) the state of being assembled; or (2) the putting together of manufactured parts to make a completed product, such as a machine or electronic circuit; or (3) a set of parts so assembled.

"Attach" (transitive verb) means to fasten, secure, or join, directly or indirectly.

"Avoid" (verb) means to refrain from using or doing something.

"Capable" (adjective) means having capacity or ability.

"Capacity" (noun) means the ability or extent of an ability, for example to receive, hold, dissolve, or absorb something or means the maximum amount that can be contained, held, dissolved, or absorbed, depending on the context.

"Condition" (noun) means: (1) a mode or state of being; or in logic (2) a proposition on which another proposition depends; the antecedent of a conditional proposition.

"Connect" (verb) means to join or fasten together, directly or indirectly.

"Control" (noun) means a comparison for checking or verifying the results of a test or scientific experiment or means a mechanism or other input that controls the operation of a machine, computer device, or process.

"Control" (verb) means to adjust to a requirement.

"Combine" (verb) means to bring into a state of unity, to make united, as in to combine ingredients of a recipe.

"Combination" (noun) means the state or result of things being united.

"Component" (noun) means a constituent element or part, as of a system or composition.

"Composition" (noun) means the makeup of a substance or means the result or product of combining or mixing, depending on the context. In the context of this disclosure, "a composition" refers to a composition according to one of the various embodiments of the disclosure. Of course, a "composition" does not include a container or vessel for mixing, containing, storing, or delivering the composition. In addition, a "composition" does not include any applicator, such as an absorbent solid material (for example, a patch or swab), for applying the composition.

"Device" (noun) means an object or instrumentality for a particular purpose.

"Drawing" (noun) means: (1) the act or an instance of drawing; or (2) (a) the art of representing objects or forms on a surface chiefly by means of lines; (b) a work produced by this art. In a patent, a "drawing" may comprise one or more figures.

"Element" (noun) means a fundamental, essential, or irreducible constituent of a composite entity. In chemistry and physics, an element is a substance composed of atoms having an identical number of protons in each nucleus. Elements cannot be reduced to simpler substances by normal chemical means. See the periodic table of the elements.

"Embodiment" (noun) means a concrete or embodied form of an abstract concept.

"Especially" (adverb) means to an extent or degree deserving of special emphasis; particularly, but not necessarily so limited.

"Essential" (adjective) means constituting or being part of the fundamental nature or essence of something.

"Essentially" (adverb) means constituting or being part of the fundamental nature or essence of something.

"Figure" (noun) means: (1) a pictorial representation; (2) a diagram or illustration; or (3) in mathematics, one of the digits specified as making up a number.

"General" (noun) means: (1) affecting or characteristic of the majority of those involved; or (2) involving only the main feature or features rather than precise or particular details.

"Improvement" (noun) means: (1) (a) the act or process of improving; or (b) the state of being improved; or (2) a change or addition that improves.

"Machine" (noun) means: (1) (a) a device consisting of fixed and moving parts that modifies mechanical energy and transmits it in a more useful form; (2) a system or device for doing work, together with its power source and auxiliary equipment; or (3) a system or device, such as a computer, that performs or assists in the performance of a human task.

"Manufacture" (noun) means: (1) the act, craft, or process of manufacturing products, especially on a large scale; or (2) a product that is manufactured.

"Mechanism" (noun) means: (1) (a) a machine or mechanical appliance; (b) the arrangement of connected parts in a machine; (2) an instrument or a process, physical or mental, by which something is done or comes into being; or (3) the sequence of steps in a chemical reaction.

"Method" (noun) means a manner or way of doing something, especially a structured or systematic way of accomplishing something.

"Minimize" (verb) means to reduce to a smaller or the smallest possible amount, extent, size, or degree as can be practical in the relevant context.

"Motion" (noun) means: (1) the act or process of changing place or position; or (2) (a) a mechanical device or piece of machinery that moves or causes motion; a mechanism; or (b) the movement or action of such a device.

"Move" (int. verb) means: (1) (a) to change in position from one point to another; (b) to change posture or position; stir; or (c) to start off; depart; or (2) To be put in motion or to turn according to a prescribed motion, as in of a machine or machinery.

"Move" (tr. verb) means: (1) (a) to change the place or position of (something); or (b) to cause to go from one place to another; or (2) (a) to change the course of; or (b) to cause to progress or advance; or (3) to cause to function (as of a machine).

"Operative" (adjective) means: (1) functioning effectively; or (2) engaged in or concerned with physical, mechanical, electrical, or other activity.

"Part" (noun) means: (1) a component that can be separated from or attached to an apparatus, device, or system; a detachable piece; or (2) something less than the whole of a man-made creation, such as of a device or apparatus.

"Portion" (noun) means something determined in relation to something that includes it.

"Process" (noun) means: (1) a series of actions, changes, or functions bringing about a result; (2) a series of operations performed in the making or treatment of a product, for example, a manufacturing process; or (3) a process, art, or method, and includes a new use of a known process, machine, manufacture, composition of matter, or material.

"Provide" (verb) means to furnish, supply, make available, or prepare. It can include making available to oneself. It does not require, but can include two individuals or actors, that is, it can include, but does not require a provider and a recipient.

"Select" (verb) means to choose from two or more alternatives.

"Significant" (adjective) means relatively large in importance, value, degree, amount, or extent in the relevant context. "Insignificant" means the opposite.

"Step" (noun) means one of a series of actions, processes, or measures taken to achieve a goal or purpose.

"Substantial" (adjective) and "substantially" (adverb) mean considerable in importance, value, degree, amount, or extent in the relevant context. "Substantial" is more, as a matter of degree, than "significant."

"System" (noun) means a group of interacting, interrelated, or interdependent elements forming a complex whole.

"Unit" (noun) means an individual, group, structure, or other entity regarded as an elementary structural or functional constituent of a whole, for example, a mechanical part or module; in another sense can mean an entire apparatus or the equipment that performs a specific function.

"Use" (verb) means to put into service; to make work or employ something for a particular purpose or for its inherent or natural purpose.

"User" (noun) means a person or entity who makes use of a thing or who uses or employs something.

"Usage" (noun) means the act of using, including usage data such as start time, end time, duration, type of activity, and intensity.

"Various" (adjective) means of diverse kinds purposefully arranged or grouped but lacking any uniformity.

"In various embodiments" (phrase) means one or more of various embodiments have the step, element, or attribute, but not all necessarily have it. Any of the various embodiments can be combined with any other of the various embodiments insofar as can be practical and non-contradictory to each other.

Regarding a Figure of the Drawing

"Diagram" (adjective) regarding a figure of drawing means a sketch, drawing, or outline, usually in simplified form, to demonstrate or explain how something works or to clarify the relationship between the parts of a whole.

"Elevation" (adjective) regarding a figure of drawing means a representation of a three-dimensional object from a vertical side, front, or rear of the structure that does not show depth perspective on a two-dimensional surface.

"Exploded" (adjective) regarding a figure of drawing means showing the parts of something separated but in positions that show their correct relation to one another.

"Oblique" (adjective) regarding a figure of drawing means showing having a slanting or sloping direction, course, or position; inclined.

"Perspective" (adjective) regarding a figure of drawing means a representation of a three-dimensional object that shows depth relationships on a two-dimensional surface.

"Plan" (adjective) regarding a figure of drawing means a representation of a three-dimensional object from a horizontal top or bottom of the structure that does not show depth perspective on a two-dimensional surface.

Relative Location or Orientation

"Adjacent" (adjective) means nearest in space or position or means immediately adjoining without intervening space.

"Edge" (noun) means the boundary of a surface. It is often, but not necessarily, a line determining the limits of an area.

"Elongated" (adjective) means having more length than width; slender.

"End" (noun) means: (1) an extremity or extremity portion of something that has length: the end of the pier; or (2) the outside or extreme edge or physical limit; a boundary: the end of town.

"Horizontal" (adjective) or "horizontally" (adverb) means parallel to or in the plane of the horizon (on earth) or to a base line (as of a view in a figure of drawing).

"Inner" (adjective) means located inward (or within or closer to a center or inside of a body).

"Longitudinal" (adjective) or "longitudinally" (adverb) means running lengthwise.

"Lengthwise" (adverb or adjective) means of, along, or in reference to the direction of the length; longitudinally.

"Outer" (adjective) means located outward (outside of or away from a center or inside of a body).

"Surface" (noun) means the extended two-dimensional outer boundary of a three-dimensional object.

"Vertical" (adjective) or "vertically" (adverb) means at right angles to the plane of the horizon [on earth] or to a base line [as of a view in a figure of drawing].

Tourniquet Terminology

"Adhesive" (noun) means a substance or material that unites, bonds, or holds surfaces together. Examples of adhesives include glue, pressure-sensitive adhesive, adhesive temporarily covered with a removable, protective strip, double-sided tape, water-resistant adhesive.

"Adhere" (verb) means to stick or hold together and resist separation.

"Adjust" (verb) means to move or change something so as to be in a more effective arrangement or desired condition.

"Axis" (noun) means a straight line about which a body or geometric object rotates or can be conceived to rotate.

"Band" (noun) means a thin strip of flexible or relatively flexible material used to encircle and bind one object or to hold a number of objects together, such as a metal band around the bale of cotton or such as a rubber band.

"Base" (noun) means: (1) the lowest or bottom part; or (2) a supporting part or layer.

"Base" (adjective) means: (1) forming or serving as a base; or (2) situated at or near the base or bottom.

"Body" (noun) means the main or central part of something.

"Buckle" (noun) means a clasp for fastening two ends, as of straps or a belt, in which a device attached to one of the ends is fitted or coupled to the other.

"Buckle" (verb transitive) means to fasten with a buckle or to become fastened with a buckle.

"Buckled" (verb intr.) mean to become fastened with a buckle. "Unbuckled" means to become unfastened with a buckle.

"Cinch" (verb) means: (a) to secure by means of a cinch; (b) to encircle or wrap tightly; or (c) to tighten an encircling cord, band, strap, or belt.

"Cinch" (noun) means an encircling cord, band, strap, or belt.

"Clasp" (verb) means to fasten with or as if with a clasp.

"Clasp" (noun) means a fastening, such as a hook or buckle, used to hold two or more objects or parts together.

"Click" (int. verb) means to produce a click or series of clicks.

"Click" (tr. verb) means to cause to click, as by striking together

"Click" (noun) means: (1) a brief, sharp sound: the click of a door latch; (2) a mechanical device, such as a pawl, that snaps into position.

"Clutch" (noun) means: (a) any of various devices for engaging and disengaging two working parts of a shaft or of a shaft and a driving mechanism; or (b) an apparatus, such as a lever or pedal, that activates one of these devices.

"Cog" (noun) means: (1) one of a series of teeth, as on the rim of a wheel or gear, for which engagement transmits successive motive force to a corresponding wheel or gear; or (2) a cogwheel.

"Container" (noun) means any object that can be used to hold things.

"Cotton" (noun) means the silky fibers from cotton plants.

"Cover" (noun) means something that covers or is laid, placed, or spread over or upon something else.

"Directions" (noun) means a message (oral or written) describing how something is to be done.

"D-ring" (noun) means a ring shaped like the letter D, often used with a strap or in a lashing.

"Disposable" (adjective) regarding an article means disposable in a municipal landfill according to current disposability standards.

"Elastic" (adjective) means easily resuming original size or shape after being deformed, as in the elastic characteristic of a rubber band.

"Emergency" (noun) means: (1) a serious situation or occurrence that happens unexpectedly and demands immediate action; or (2) a condition of urgent need for action or assistance, as in a state of emergency.

"Emergency" (adjective) means for use during emergencies, as in a sudden major bodily injury.

"Engage" (tr. verb) means: (a) to cause the components of (a part of a machine) to touch or mesh so as to transmit motion or force: engaged the gears; or (b) to put (a part of a machine) into operation: engaged the mower blades; or (intr. verb) means to become meshed or interlocked: the gears or teeth engaged.

"Engagement" (noun) means: (a) the action of engaging or the state of being engaged; or (b) the condition of being in working position, for example, the engagement of gears or teeth.

"Fastener" (noun) means a device, such as a clip, pin, or clasp, that attaches something firmly to something else.

"Feed" (verb) means: (a) to move steadily, as into a machine for processing; or (b) to be channeled.

"Female" (adjective) means designed to receive or fit around a complementary male part, as a slot or receptacle, for example, the female end of an electrical extension cord.

"Finger" (noun) means: (1) one of the five digits of the hand, especially one other than the thumb; or (2) something that resembles one of the digits of the hand.

"Fix" (verb) means: (a) to place securely; make stable or firm; (b) to secure to another; attach.

"Flexible" (adjective) means capable of being easily flexed or bent by hand. More particularly, as used herein, "flexible" means able to be flexed or bent at least a 90-degree angle in at least one orientation without creasing or breaking. If unspecified, flexible can mean able to be flexed or bent at least 90-degree angle in any orientation. "Flexible" can include the characteristic elastic but does not necessarily mean or require having the characteristic of being elastic.

"Float" (verb) means: (1) (a) to remain suspended within or on the surface of a fluid without sinking; or (b) to be suspended in or move through space as if supported by a liquid; or (2) to move easily or lightly.

"Fold" (verb) means to bend or lay so that one part covers the other.

"Free" (adverb) or "freely" (adverb) means in a free manner; without binding, fastening, or restraint.

"Free" (adjective) means not bound, fastened, or attached.

"Friction" (noun) means the resistance encountered when one body is moved in contact with another.

"Gear" (noun) means a toothed machine part, such as a wheel or cylinder, that meshes with another toothed part to transmit motion or to change speed or direction.

"Glide" (verb) means to move in a smooth, effortless manner.

"Groove" (noun) means a long or elongated narrow furrow or channel.

"Hand" (noun) means the terminal part of the human arm located below the forearm, used for grasping and holding and consisting of the wrist, palm, four fingers, and an opposable thumb.

"Handheld" (adjective) means small and light enough to be held and used by holding with one hand.

"Handle" (noun) means a part that is designed to be held or operated by hand.

"Hard" (adjective) means lacking in softness, relatively or comparatively.

"Hold" (verb) means: (1) to keep from falling or moving; to support; or (2) to carry or support; or (3) to have or hold in one's hands or grip or means to retain in place or position.

"Hub" (noun) means the center part of a circular or rotating part, such as of a wheel, fan, or propeller.

"Increment" (noun) means: (1) the process of increasing in number, size, quantity, or extent; (2) something added or gained; (3) a small or slight, often barely perceptible augmentation; or (4) one of a series of regular additions or contributions.

"Index finger" (noun phrase) means the finger next to the thumb; also known as the first finger or the forefinger.

"Indicia" (noun) means distinctive marks, such as diagrams or text.

"Insert" (verb) means to introduce into or move into.

"Insert" (noun) means something inserted or intended for insertion, as a picture or chart into written material or as information inserted into the packaging regarding a product.

"Internal" (adjective) means: (1) of, relating to, or located within the limits or surface; inner; or (2) located, acting, or effective within the body.

"Keeper" (noun) means a device or fitting that catches or holds a moving part.

"Leading" (adjective) means having a position in the lead.

"Leg" (noun) means: (1) one of the limbs or appendages that an animal uses for locomotion or support; (2) a supporting part resembling a leg in shape or function; or (3) one of the branches of a forked or jointed object.

"Lock" (verb) means: (1) to fix in place so that movement or escape is impossible; to hold fast; to become rigid or immobile; or (2) to clasp or link firmly.

"Lock" (noun) means an interlocking or entanglement of elements or parts.

"Loop" (noun) means: (1) (a) a length of line, thread, ribbon, or other thin material that is curved or doubled over making an opening; (b) the opening formed by such a doubled line, thread, ribbon, or other thin material; or (2) something having a shape, order, or path of motion that is circular or curved over on itself.

"Male" (noun) means designating an object designed for insertion into another part or a socket, for example, an electrical plug.

"Mesh" (adjective) means: (1) (a) the engagement of teeth; or (b) the state of being so engaged, for example, the teeth in mesh.

"Mesh" (verb) means to cause teeth to become engaged; to become engaged or interlocked.

"Package" (noun) means a one or more things wrapped, boxed, or otherwise contained or held together.

"Pad" (noun) means mass of padding, usually but not necessarily thin and flat, such as of a block of a soft, of a protective, or of an absorbent material. A "pad" can be for protecting the skin from a hard item.

"Permanent" (adjective) means continuing or enduring without marked change in status or condition or place, especially within a relevant time.

"Place" (verb) means to move or put into a certain place or abstract location.

"Plastic" (adjective) regarding the substance of a material is a generic name for certain synthetic or semisynthetic materials that can be molded or extruded into objects or films or filaments or used for making, for example, a coating. Plastic materials that can be used for a sheet material include various polymeric materials such as nylon, acrylic, polystyrene, polycarbonate, polyester, and polyvinyl (sometimes referred to simply as vinyl).

"Polymeric" (adjective) means of, relating to, or consisting of a polymer or means of or relating to chemical polymerization.

"Ratchet" (noun) means: (1) a mechanism consisting of a pawl that engages the sloping teeth of a wheel or bar, permitting motion in one direction only; or (2) the pawl, wheel, or bar of such a mechanism; or (3) the toothed rack or wheel forming part of such a mechanism.

"Ratchet" (verb) to cause to increase or decrease by increments; to increase or decrease by increments.

"Release" (verb) means to set free from physical restraint or binding; to let go.

"Remove" (verb) means to remove something, as by lifting, pushing, taking off, taking out, etc.

"Resilient" (adjective) means capable of returning to an original shape or position, as after having been compressed.

"Ring" (noun) means: (1) a circular object, form, line, or arrangement; (2) a circular band used for carrying, holding, or containing something.

"Rotate" (int. verb) means: (1) to turn around on an axis or center. See Synonyms at turn; or (2) to proceed in sequence; take turns or alternate; or (tr. verb) means: (1) to cause to turn on an axis or center; or (2) to cause to alternate or proceed in sequence.

"Saddle" (noun) means: (a) a leather seat for a rider, secured on an animal's back by a girth; (b) similar tack used for attaching a pack to an animal; (c) the padded part of a driving harness fitting over a horse's back; or (d) something generally shaped like a saddle.

"Sheet" (noun) means a flat article that is thin relative to its length and width.

"Slant" (noun) means: (a) a line, plane, course, or direction that is other than perpendicular or horizontal; a slope; or (b) a sloping thing or piece of ground.

"Sleeve" (noun) means: (1) a part of a garment that covers all or part of an arm; (2) an object having an opening (like a sleeve) into which another object fits or slides into; or (3) a case into which an object or device fits.

"Slide" (verb) means: (a) to move over a surface while maintaining smooth continuous contact; or (b) to pass smoothly and quietly; to glide.

"Slip" (verb) means to move smoothly and easily.

"Slot" (noun) means a narrow opening; a groove or slit. For example, a slot for coins or a mail slot.

"Socket" (noun) means an opening or a cavity into which an inserted part is designed to fit, such as a socket to receive a (male) electrical plug or a socket to receive the outside diameter of an end of a tube or pipe.

"Soft" (adjective) means lacking in hardness, relatively or comparatively.

"Spin" (int. verb) means to rotate rapidly; whirl; or (tr. verb) means to cause to rotate swiftly.

"Spring" (int. verb) means to move suddenly, especially because of being resilient or moved by a spring; or (tr. verb) means to release from a checked or inoperative position.

"Stage" (verb) means to arrange and carry out.

"Stop" (noun) means: (1) the act of stopping or the condition of being stopped; or (2) a structure or device or means that obstructs, blocks, or plugs up; or (3) a part in a mechanism that stops or regulates movement.

"Strap" (verb) means to fasten or secure with a strap or other elongated flexible material.

"Strap" (noun) means: (1)(a) a long narrow strip of pliant material such as leather or of fabric; or (b) such a strip equipped with a buckle or similar fastener for binding or securing objects.

"Structural" (adjective) means affecting or involved in structure or construction.

"Surface" (noun) means the extended two-dimensional outer boundary of a three-dimensional object.

"Tab" (noun) means a projection, flap, or short strip attached to an object to facilitate opening, handling, or identification.

"Taut" (adjective) means pulled or drawn tight; not slack.

"Tautness" (noun) means the state or degree of being taut.

"Temporary" (adjective) means not permanent.

"Tensioner" (noun) means a structure or device for adjusting, controlling, or regulating tautness.

"Tensile strength" (adjective phrase) regarding paper or other sheet material is a measure of its resistance to breaking by elongation.

"Thick" (adjective) means of relatively larger extent from one surface to the opposite or in cross-section of a body or structure, especially in comparison to a length and width, but still less than the length and the width, usually in the smallest solid dimension.

"Thin" (adjective) means of relatively small extent from one surface to the opposite or in cross-section of a body or structure, especially in comparison to a length and a width, usually in the smallest solid dimension.

"Thumb" (noun) the short thick digit of the human hand, next to the index finger and opposable to each of the other four digits.

"Tight" (adjective) means: (1) fixed or fastened firmly in place; (2) stretched or drawn out fully; (3) fitting close or too close to the skin; or (4) experiencing a feeling of constriction.

"Tight" (adverb) means: (1) firmly or securely; or (2) snugly or with constriction.

"Tighten" (verb) means to make or become tight or tighter.

"Tooth" (noun) means: (1) one of a set of hard, bonelike structures in the mouths of vertebrates, usually attached to the jaw or rooted in sockets and used for biting or chewing food or as a means of attack or defense; or (2) a projecting part resembling a tooth in shape or function, as on a comb, gear, or saw.

"Tooth" (verb) means: (1) to furnish a tool with teeth; or (2) to make a jagged edge on.

"Tourniquet" (noun) means an encircling strap or apparatus used to control bleeding by temporarily slowing or stopping the flow of blood through a portion of the body. Most commonly, a tourniquet is used to slow or stop the flow of blood through a limb. More recently, tourniquets have been adapted for use as "junctional tourniquets," that is, to be positioned around a portion of the body such as the torso to apply pressure to slow or stop the flow of blood through a wound. In contrast, a pneumatic tourniquet is an air-powered device including a pressure-regulating unit, connecting tubing, and an inflatable cuff. The cuff of a pneumatic tourniquet is intended to be wrapped around a patient's limb and inflated to reduce or totally occlude circulation during surgery. As used herein, a "tourniquet" means a nonpneumatic type of tourniquet, unless the specific context otherwise requires.

"Trailing" (adjective) means having a position following behind.

"Turn" (tr. verb) means: (1)(a) to cause to move around an axis or center; cause to rotate or revolve; (1)(b) to cause to move around in order to achieve a result, such as opening, closing, tightening, or loosening; or (2) to fold, bend, or twist (something); or (int. verb) means to move around an axis or center; rotate or revolve.

"Twist" (verb) means: (1) (a) to wind together (for example, two or more threads) so as to produce a single strand; (b) to form in this manner; (2) to wind or coil about something; (3) to interlock or interlace; (4) to cause to rotate or turn in another direction; (5) to impart a spiral or coiling shape to, as by turning the ends in opposite directions; (6) to open or close or loosen or tighten by turning; or (7) to alter the normal aspect of, or to contort.

"Webbing" (noun) means a strong, narrow, closely woven fabric used especially for seat belts and harnesses or in upholstery.

"Windlass" (noun) means a bar or rod or other body for providing leverage for the twisting of a strap or cable around itself, in the general nature of the operation of a "Spanish windlass." A "Spanish windlass" means a suitable bar, rod, or stick used as a device for twisting and tightening a rope or cable, or strap. The operating principle of a Spanish windlass is illustrated in FIGS. 53-54.

"Wrap" (verb) means to wrap or coil around something else.

Medical Terminology

"Animal" (noun) means an animal organism other than a human.

"Administer" (verb) means applying, implanting, absorbing, ingesting, injecting, inhaling, or otherwise introducing to the body of an animal.

"Bacteria" (noun) means single-celled or non-cellular spherical or spiral or rod-shaped microorganisms lacking chlorophyll that reproduce by fission; important as pathogens and for biochemical properties; taxonomy is difficult; often considered plants.

"Bleeding out" (verb phrase), also known as "exsanguination," is a condition characterized by a fatal loss of blood.

"Body" (noun) in pharmacology means the entire material or physical structure of an organism, especially of a human or animal.

"Efficacy" (adjective) means power or capacity to produce a desired effect; effectiveness.

"Efficacious" (adjective) means producing or capable of producing a desired effect.

"FDA" (proper name) is an abbreviation for the U.S. Food and Drug Administration.

"Feel" or "feeling" (verb) means to perceive by touch or by sensation of the skin.

"Feel" or "feeling" (noun) means a perception by touch or by sensation of the skin. Unless otherwise stated, "feel" or "feeling" of a composition means within a few seconds of touching and moving the composition between bare fingers (including thumb).

"Human" (noun) means a member of the primate genus *Homo*, especially a member of the species *Homo sapiens*, distinguished from other apes by a large brain and the capacity of reason and speech.

"Irritate" (verb) means to make sore or inflamed.

"Limb" (noun) means one of the jointed appendages of an animal, such as an arm, leg, wing, or flipper, used for locomotion or grasping.

"Mammal" (noun) means any of various warm-blooded vertebrate animals of the class Mammalia, including humans, characterized by a covering of hair on the skin and, in the female, milk-producing mammary glands for nourishing the young.

"Medical" (adjective) means relating to the study or practice of medicine.

"Medicine" (noun) means the science and art of diagnosing and treating disease or injury and maintaining health or the branch of this science encompassing treatment by drugs, diet, exercise, and other non-surgical means.

"Microbe" or "Microorganism" (noun) means any organism of microscopic size.

"Normal" (adjective) means functioning or occurring in a natural way; lacking observable abnormalities or deficiencies. "Abnormal" (adjective) means not normal.

"Occlude" (verb) means: (1) to cause to become closed; obstruct, as in occlude an artery; or (2) to prevent the passage of, as in occlude the flow of blood.

"Patch" (noun) means a dressing or covering applied to protect a wound or sore or means a transdermal patch, depending on the context.

"Patient" (noun) means a human or an animal that receives medical attention, care, or treatment.

"Pathogen" (noun) means any disease-producing agent (especially a virus or bacterium or other microorganism).

"Skin" (noun) means the membranous tissue forming the external covering or integument of a human or an animal and consisting in vertebrates of the epidermis and dermis.

"Shelf life" (noun phrase) means the length of time a product can be stored without becoming unsuitable for use.

"Stable" (verb) means resistant to change of position or condition, and in chemistry means not easily or rapidly decomposed or otherwise modified chemically.

"Stability" (noun) means the state or quality of being stable, especially, resistance to change, displacement, or deterioration.

"Stabilize" (verb) means to make more stable, for example, to increase to stability of something.

"Treat" (verb) in medicine means to give medical aid to counteract, for example, a disease or other medical condition. As used herein, the terms "treatment," "treat," and "treating" can refer to any one or more of reversing, alleviating, delaying the onset of, or inhibiting the progress of a "pathological condition" (for example, a disease, disorder, or condition, or one or more signs or symptoms thereof) described herein. In some embodiments, treatment can be administered after one or more signs or symptoms have developed or have been observed.

"Topical" (verb) in medicine means relating to, applied to, or affecting a localized area of the body, especially of the skin, for example, a topical anesthetic.

"Veterinary" (adjective) means related to or connected with the medical or surgical treatment of animals.

Physical Conditions, Properties, and Phases

"Absence" (noun) means the state of being absent or only present at a concentration below the sensitivity of a test.

"Amount" (noun) means a number or a quantity (as of a measurement, such as of a mass, weight, or concentration).

"Liquid" (noun) means, depending on the context: (1) a substance that is liquid (adjective) at room temperature and pressure; (2) the state in which a substance exhibits a characteristic readiness to flow with little or no tendency to disperse and relatively high incompressibility (and not boiling, precipitating, or crystalizing); or (3) a substance in the fluid state of matter having no fixed shape but a fixed volume.

"Liquid" (adjective) regarding a substance means existing as or having characteristics of a liquid; especially tending to flow as a liquid.

"Material" (noun) means the tangible substance that goes into the makeup of a physical object, which can be constituted of one or more phases.

"Phase" (noun) means a substance having a chemical composition and physical state that is distinguishable from an adjacent phase of a substance having a different chemical composition or a different physical state.

"Pressure" (noun) in physics means force applied uniformly over a surface, measured as force per unit area.

"Room temperature" (noun phrase) means standard laboratory temperature.

"Solid" (noun) means the physical state of matter distinguished from liquid and gaseous by having a definite shape and volume. Unless otherwise stated, the state of a substance is determined under standard laboratory conditions.

"Solid" (adjective) regarding a substance means existing as or having characteristics of a solid; of definite shape and volume; not liquid or gaseous.

"Standard Laboratory Conditions" (noun phrase) means at a temperature of 77° F. (25° C.), at a pressure of 1 (one) atmosphere (101.325 kPa or 760 mmHg), without applied shear (mixing force), and ambient relative humidity in the range of 40-60%.

"Standard laboratory pressure" or "standard pressure" or "normal pressure" (noun phrase) means 1 (one) atmosphere (101,325 Pascal).

"Standard laboratory temperature" or "normal temperature" (noun phrase) means at a temperature of 77° F. (25° C.).

"State" (noun) means a condition or mode of being, as with regard to circumstances. In chemistry and physics, it means the condition of a physical system with regard to phase, form, composition, or structure. The common physical states of matter include solid, liquid, and gas. Distinctions among these physical states are based on differences in intermolecular attractions. Solid is the state in which intermolecular attractions keep the molecules in fixed spatial relationships. Liquid is the state in which intermolecular attractions keep molecules in proximity (low tendency to disperse), but do not keep the molecules in fixed relationships. Gas is that state in which the molecules are comparatively separated, and intermolecular attractions have relatively little effect on their respective motions (high tendency to disperse). The physical state of a substance depends on temperature and pressure. If not other otherwise specifically stated, the physical state or phase or condition of a substance (or mixture of substances) and other physical properties are determined under Standard Laboratory Conditions.

"Substance" (noun) means that which has mass and occupies space, i.e., matter; or a material of a particular kind or constitution.

"Weight" (noun) means a measure of the heaviness of an object, and more particularly, the force with which a body is attracted to Earth or another celestial body, equal to the product of the object's mass and the acceleration of gravity. In the context of earth's gravitational constant, the weight of an object can be loosely equated to the mass of the object. For example, 2.2 pounds weight is equivalent to 1 kg mass, and grams or kilograms can be referred to as weights.

CONCLUSION

Therefore, the present disclosure is well adapted to attain the purposes and advantages mentioned as well as those that are inherent therein.

The various disclosed embodiments are illustrative only, as the present disclosure can be modified and practiced in different but equivalent manners apparent to those skilled in the art having the benefit of the teachings herein. It is, therefore, evident that the particular illustrative embodiments disclosed above can be altered or modified and all such variations are considered within the scope of the present disclosure.

The various elements or steps according to the disclosed elements or steps can be combined advantageously or practiced together in various combinations or subcombinations of elements or sequences of steps to increase the efficiency and benefits that can be obtained from the disclosure.

It should be understood that one or more of the above and various embodiments can be combined with one or more of the other various embodiments, unless explicitly stated otherwise.

The illustrative disclosure can be practiced in the absence of any element or step that is not specifically disclosed or claimed.

Any particular embodiment of the disclosure that falls within the prior art can be explicitly excluded from any one or more of the claims. Because such embodiments are deemed to be known to one of ordinary skill in the art, they can be excluded even if the exclusion is not set forth explicitly herein.

Any particular embodiment of the disclosure can be explicitly excluded from a particular patent claim, for any reason, whether or not related to the existence of prior art. Where elements are presented as lists, for example, in Markush group format, each subgroup of the elements is also disclosed, and any element or elements can be removed from the claimed group.

Those of ordinary skill in the art will recognize or be able to ascertain using no more than routine experimentation many equivalents to the specific embodiments of this disclosure. Those of ordinary skill in the art will appreciate that various changes and modifications to this description can be made without departing from the spirit or scope of the disclosure.

Furthermore, no limitations are intended to the details of composition, design, construction, or steps of the disclosure, other than as set forth in a specific claim.

What is claimed is:

1. A twisting assembly, the twisting assembly comprising:
   (A) a base part,
      (1) wherein the base part comprises a plurality of teeth arranged in a circle; and
      (2) wherein the base part has an opening through the circle of the plurality of teeth of the base part; and
   (B) a twisting part:
      (1) wherein the twisting part is adapted to be operatively connected to a portion of an elongated flexible material when the portion of the elongated flexible material is positioned through the opening through the circle of the plurality of teeth of the base part;
      (2) wherein the twisting part comprises a windlass portion;
      (3) wherein the twisting part is adapted to allow movement of the twisting part away from close engagement with the teeth of the base part to allow rotation of the twisting part in one rotational direction relative to the base part; and
      (4) wherein the twisting part is adapted to allow movement of the twisting part into close engagement with the teeth of the base part to prevent rotation of the twisting part in the opposite rotational direction relative to the base part.

2. The twisting assembly according to claim 1, wherein the opening through the circle of the plurality of teeth of the base part is from below and adapted such that the elongated flexible material can be threaded from below and upwardly through the opening through the circle of the plurality of teeth of the base part.

3. The twisting assembly according to claim 1, wherein the base part is adapted to allow the portion of the elongated flexible material to be threaded:
   (a) into and upward through an interior portion of the base part up to the twisting part; and
   (b) from the twisting part downward and out of the interior portion of the base part.

4. The twisting assembly according to claim 1, wherein the base part has a cylindrical portion axially aligned with the circle of teeth arranged in a circle of the base part; and wherein the opening through the circle of the plurality of teeth of the base part is at least partially formed by the cylindrical portion of the base part.

5. The twisting assembly according to claim 1, comprising a hub portion and a socket portion adapted for rotationally aligning the twisting part relative to the base part.

6. The twisting assembly according to claim 1, wherein the twisting part comprises a plurality of teeth arranged in a circle, the teeth of the twisting part being adapted to move out of close engagement with the teeth of the base part to allow rotating in one rotational direction but when in close engagement with the teeth of the base part prevents rotation in the opposite rotational direction.

7. The twisting assembly according to claim 6, wherein the twisting part has a cylindrical portion axially aligned with the circle of teeth arranged in a circle of the twisting part.

8. The twisting assembly according to claim 1, wherein the plurality of teeth of the base part is at least 5 teeth and less than 40 teeth.

9. The twisting assembly according to claim 1, wherein the twisting assembly does not have any pawl.

10. The twisting assembly according to claim 1, wherein the twisting part comprises at least one slot in or adjacent to the windlass portion for operatively engaging the portion of the elongated flexible material with the twisting part.

11. The twisting assembly according to claim 1, wherein the portion of the elongated flexible material comprises a stop attached to or formed in the portion of the elongated flexible material, and wherein the twisting part is adapted to cooperate with the stop to prevent movement of the portion of the elongated flexible material through the twisting part.

12. The twisting assembly according to claim 1, whereby when the portion of the elongated flexible material is operatively connected to the twisting part and when the twisting part is rotated in the one rotational direction, the portion of the elongated flexible material is twisted about itself, thus having an effect of shortening the overall length of the elongated flexible material and pulling the twisting part downward into engagement with base part.

13. The twisting assembly according to claim 1, wherein the twisting assembly and the elongated flexible material are adapted for being positioned such that the elongated flexible material is held taut, either around an object or between two anchor points.

14. The twisting assembly according to claim 13, wherein when the elongated flexible material is positioned and held taut, the base part is operatively held against twisting relative to a length of the elongated flexible material.

15. The twisting assembly according to claim 1, wherein the twisting assembly comprises the elongated flexible material.

16. The twisting assembly according to claim 15, wherein the elongated flexible material is adapted for being positioned and held taut, either around an object or between two anchor points.

17. The twisting assembly according to claim 15, wherein the elongated flexible material is substantially non-elastic.

18. The twisting assembly according to claim 15, wherein the elongated flexible material comprises a strap.

19. A twisting assembly, the twisting assembly comprising:
(A) a base part,
(1) wherein the base part comprises a plurality of teeth arranged in a circle;
(2) wherein the plurality of teeth of the base part is at least 3 teeth; and
(3) wherein the base part has an opening through the circle of the plurality of teeth of the base part; and
(B) a twisting part:
(1) wherein the twisting part is adapted to be operatively connected to a portion of an elongated flexible material when the portion of the elongated flexible material is positioned through the opening through the circle of the plurality of teeth of the base part;
(2) wherein the twisting part comprises a windlass portion;
(3) wherein the twisting part is adapted to allow movement of the twisting part away from close engagement with the teeth of the base part to allow rotation of the twisting part in one rotational direction relative to the base part; and
(4) wherein the twisting part is adapted to allow movement of the twisting part into close engagement with the teeth of the base part to prevent rotation of the twisting part in the opposite rotational direction relative to the base part; and
wherein the base part is adapted to allow the portion of the elongated flexible material to be threaded:
(a) into and upward through an interior portion of the base part up to the twisting part; and
(b) from the twisting part downward and out of the interior portion of the base part;
whereby when the portion of the elongated flexible material is operatively connected to the twisting part and when the twisting part is rotated in the one rotational direction, the portion of the elongated flexible material is twisted about itself, thus having an effect of shortening the overall length of the elongated flexible material and pulling the twisting part downward into engagement with base part.

20. The twisting assembly according to claim 19, wherein the twisting part comprises a plurality of teeth arranged in a circle, the teeth of the twisting part being adapted to move out of close engagement with the teeth of the base part to allow rotating in one rotational direction but when in close engagement with the teeth of the base part prevents rotation in the opposite rotational direction.

21. The twisting assembly according to claim 19, wherein the twisting assembly comprises a cooperating system of teeth that allow the turning of the windlass portion in one rotational direction to twist and tighten the elongated flexible material but wherein the cooperating system of teeth prevent the turning of the windlass portion in the opposite rotational direction to avoid untwisting of the elongated flexible material, whereby the elongated flexible material can be incrementally tightened.

22. The twisting assembly according to claim 19, wherein the twisting assembly comprises the elongated flexible material.

23. The twisting assembly according to claim 22, wherein the elongated flexible material is adapted for being positioned and held taut, either around an object or between two anchor points.

24. The twisting assembly according to claim 22, wherein the elongated flexible material is substantially non-elastic.

25. The twisting assembly according to claim 22, wherein the elongated flexible material comprises a strap.

* * * * *